United States Patent
Jäger et al.

(10) Patent No.: US 11,958,871 B2
(45) Date of Patent: Apr. 16, 2024

(54) INHIBITORS OF BACTERIAL GLUTAMINYL CYCLASES FOR USE IN THE TREATMENT OF PERIODONTAL AND RELATED DISEASES

(71) Applicant: FRAUNHOFER-GESELLSCHAFT ZUR FÖRDERUNG DER ANGEWANDTEN FORSCHUNG E.V., Munich (DE)

(72) Inventors: Christian Jäger, Halle (DE); Linda Liebe, Halle (DE); Daniel Ramsbeck, Halle (DE); Miriam Linnert, Halle (DE); Stefanie Geissler, Halle (DE); Anke Piechotta, Halle (DE); Diane Meitzner, Wolfen (DE); Holger Cynis, Halle (DE); Mirko Buchholz, Halle (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 891 days.

(21) Appl. No.: 16/971,618

(22) PCT Filed: Feb. 22, 2019

(86) PCT No.: PCT/EP2019/054476
§ 371 (c)(1),
(2) Date: Aug. 20, 2020

(87) PCT Pub. No.: WO2019/162458
PCT Pub. Date: Aug. 29, 2019

(65) Prior Publication Data
US 2020/0392174 A1 Dec. 17, 2020

(30) Foreign Application Priority Data
Feb. 23, 2018 (EP) .................................. 18158343

(51) Int. Cl.
C07F 15/02 (2006.01)
A61P 31/04 (2006.01)
C07D 471/04 (2006.01)

(52) U.S. Cl.
CPC ............ *C07F 15/025* (2013.01); *A61P 31/04* (2018.01); *C07D 471/04* (2013.01)

(58) Field of Classification Search
CPC ......... C07F 15/025; A61P 31/04; C07D 47/04
See application file for complete search history.

(56) References Cited

U.S. PATENT DOCUMENTS

| 4,977,144 A | 12/1990 | Fujimoto et al. |
| 2002/0165241 A1 | 11/2002 | Claiborne et al. |
| 2007/0202586 A1 | 8/2007 | Wang et al. |
| 2009/0318428 A1 | 12/2009 | Honold et al. |
| 2019/0367511 A1 | 12/2019 | Potempa et al. |

FOREIGN PATENT DOCUMENTS

| CN | 102186475 A | 9/2011 |
| CN | 102695546 A | 9/2012 |
| CN | 102791704 A | 11/2012 |
| CN | 105263927 A | 1/2016 |
| EA | 018104 B1 | 5/2013 |
| WO | 02/068409 A1 | 9/2002 |
| WO | WO 2007017143 | * 2/2007 |
| WO | 2008/028617 A1 | 3/2008 |
| WO | 2016/171755 A1 | 10/2016 |
| WO | WO 2018011138 | * 6/2018 |
| WO | 2019/162458 A1 | 8/2019 |

OTHER PUBLICATIONS

Buchholz, "Targeting Bacterial Glutaminyl Cyclases in Peridontitis—Rational Approaches for the Generation of Selective, Locally Acting Antibiotics; Fighting Against Systemic Diseases," Fraunhofer-Okinawa Institute of Science and Technology (OIST) Workshop, Okinawa, Japan, Apr. 8-10, 2015, 39 pages.

Buchholz, "Targeting Bacterial Glutaminyl Cyclases in Peridontitis—Rational Approaches for the Generation of Selective, Locally Acting Antibiotics," Joint meeting in honour of Prof. Jan Potempa and Annual TRIGGER Conference, Krakow, Poland, May 15-17, 2015, 30 pages.

European Commission, "Final Report Summary—TRIGGER (King of hearts, joints and lungs; periodontal pathogens as etiologic factor in RA, CVD and COPD and their impact on treatment strategies)," Project ID: 306029, Aug. 16, 2017, 15 pages, URL=https://cordis.europa.eu/result/rcn/202357_en.html.

Huang et al., "Crystal Structure and Functional Analysis of the Glutaminyl Cyclase from *Xanthomonas campestris*," *J. Mol. Biol.* 401:374-388, 2010.

Wintjens et al., "Crystal Structure of Papaya Glutaminyl Cyclase, an Archetype for Plant and Bacterial Glutaminyl Cyclases," *J. Mol. Biol.* 357:457-470, 2006.

Zerhouni et al., "Purification and characterization of papaya glutamine cyclotransferase, a plant enzyme highly resistant to chemical, acid and thermal denaturation," *Biochimica et Biophysica Acta* 1387:275-290, 1998.

(Continued)

*Primary Examiner* — Shirley V Gembeh
(74) *Attorney, Agent, or Firm* — Seed IP Law Group LLP

(57) ABSTRACT

The present invention relates to novel compounds which are particularly useful as inhibitors of bacterial glutaminyl cyclases (bacQC); pharmaceutical compositions comprising such compounds; compounds and/or pharmaceutical compositions for use in methods for treatment, in particular for use in the treatment of periodontitis and related conditions; as well as to crystals comprising bacterial glutaminyl cyclases, methods for identifying candidate compounds which may associate with the binding pocket of a bacQC and/or are bacQC inhibitors.

14 Claims, 12 Drawing Sheets

Specification includes a Sequence Listing.

(56) References Cited

OTHER PUBLICATIONS

Hajishengallis, "Immuno-microbial pathogenesis of periodontitis: Keystones, pathobionts, and the host response," *Trends Immunol.* 35(1): 3-11, Jan. 2014.
Hajishengallis et al., "The Keystone Pathogen Hypothesis," *Nat Rev Microbiol.* 10(10): 717-725, Oct. 2012.
Socransky et al., "Microbial complexes in subgingival plaque," *Journal of Clinical Periodontology 25*: 134-144, 1998.

* cited by examiner (A)
```
PgQC  ----MKRLITTGAAFLLAATLSACNGNNTSETQGDRTEQAETVQADLFSADSAYTFVQRQ
hQC   MAGGRHRRVVGTLHLLLLVAALPWASRGVSPSASAWPEEKNYHQPAILNSSALRQIAEGT
         :* :.    :**  .:  .  ....* :  .  .*: :  *. ::.:.:   :.:

PgQC  VN----------FGPRIPGTAPHRACGDWLVATLRSFGAAVQEQTAEIKAHDGTMLPMR
hQC   SISEMWQNDLQPLLIERYPGSPGSYAARQHIMQRIQRLQADWVLEIDTFLSQTPYGYRSF
       :   * **:.     *. :  ::   :   *        :    :    :::

PgQC  -NIIASYRPEATGRMLLMAHWDTRPVCDQDANPAMHTETFDGADDGGSGVGVLLEIARYL
hQC   SNIISTLNPTAKRHLVLACHYDSKYFSHWNN------RVFVGATDSAVPCAMMLELARAL
       ***::  .*  *.  :::*  .*:*::  ...  :      ..* **  *..  .::**:** *

PgQC  GQQKD---------LGMGIDIVFFDTEDYGSYGDDESWCLGSQYWSR----NPHVAGYK-
hQC   DKKLLSLKTVSDSKPDLSLQLIFFDGEEAFLHWSPQDSLYGSRHLAAKMASTPHPPGARG
       .::       .:.::::*** *:        :  .:.   **::  :        .** .*  :

PgQC  ------AEAGILLDMVGAKGATFY--------WEYFSKSYAPGLISAVWQTAAALGYGNY
hQC   TSQLHGMDLLVLLDLIGAPNPTFPNFFPNSARWFERLQAIEHELHELGLLKDHSLEGRYF
             :  :***::** ..**           *       ::     *  .     . :*    :

PgQC  FIQADGGALTDDHVPVIKNLGIPCIDIINYSSKNEHGFGDHWHTQRDNMQIIDKNVLDAV
hQC   QNYSYGGVIQDDHIPFLR-RGVPVLHLIPSP------FPEVWHTMDDNEENLDESTIDNL
       : **.: ***:*.::    *:*  ::.:*    .        *  ; *** ** : :*:..:* :

PgQC  GETVIRYLDEQVKAASH
hQC   NKILQVFVLEYLHL---
       .: :   :: *  ::
```

(B)
```
PiQC  MGRQLAARYGTDTGCQTKIKRTTMNGKIKFLCSGMAVLLLAAFAFSCKGKSSNNSTEDGD
PgQC  ---------------------------MKRLITTGAAFLLAATLSACNGNNTS--ETQGD
TfQC  -------------------------MDRMINKYAGVLLGSLILSCCGQKNTTKEETTE
                                 :. :  .  * .**.:   :*  *:... :

PiQC  TVATAK-PVGPTFNPDSAFAYTAAQCDFGPRTMNSSAHDKCEQWIISKFKQYGCEVQTQK
PgQC  RTEQAETVQADLFSADSAYTFVQRQVNFGPRIPGTAPHRACGDWLVATLRSFGAAVQEQT
TfQC  PADTDKRIEAPTFNADSAYAYIERQVAFGPRVPNTEAHQRCADYLAGELDRHGAKVYVQE
       .   :   .  *. *** :::   *  ****  :   *   * ::: . :   .*. *  *

PiQC  ADLKAYDGTILKSTNIIARTNPNAQRRILLCAHWDSRPWADNDPDSTNHKKPVMAANDGA
PgQC  AEIKAHDGTMLPMRNIIASYRPEATGRMLLMAHWDTRPVCDQDANPAMHTETFDGADDGG
TfQC  AVLTAYNGEKLKAQNIVGAFQPEKSRRVLLFAHWDSRPYADHDTDEANHRKPIDGADDGG
      *  :..*::*    **  .  .*:  :*:** ****:**  .  .*   :  : .  .*:**.

PiQC  SGVGVMIELARQLQADSTLNVGVDFVCFDAEDWGVPQWETNYQEQSGDSWALGSNYFAKN
PgQC  SGVGVLLEIARYLGQQKDLGMGIDIVFFDTEDYGSYG-----D---DESWCLGSQYWSRN
TfQC  SGVGILLEIARQIQ-AKAPAIGIDIVFFDAEDYGTPEFVDEYK---PDTWCLGSQFWAKN
      ****:::*:**  :    .   :*:*:*** **:*         .     ::*.***::::*

PiQC  LPL-TVRPEFGILLDMVGGEGAQFYKEGISLQYAPDIVDRVWEAAKSAGFEAYFPTTRGG
PgQC  PHVAGYKAEAGILLDMVGAKGATFYWEYFSKSYAPGLISAVWQTAAALGYGNYFIQADGG
TfQC  PHVPNYKAEFGILLDMVGSRGATFYKESTSVQYAARYVEKVWTAARELGYGKYFINAQGG
        :   :  * ********..** **  *  *  .**     .**  ..  * .   **  ; **

PiQC  MVTDDHYPLNKIAAIPTIDIIPHYPDCAQSTFGPTWHTVNDTMEHIDRTTLQAVGQTLIQ
PgQC  ALTDDHVPVIKNLGIPCIDIINY-SSKNEHGFGDHWHTQRDNMQIIDKNVLDAVGETVIR
TfQC  AIVDDHQYVIQGLRTPCLDIINY-DPDTQSGFGPYWHTQNDTMENIDRETLKAVGETILN
      :.***  : :   *  :*** :       : ** ***  .*.*:*:  .* .:*.:*:.

PiQC  VLYSM------
PgQC  YLDEQVKAASH
TfQC  VIYNH------
```

FIG. 1

(C) SEQ ID NO. 1

```
          10         20         30         40         50         60
  MKRLITTGAA FLLAATLSAC NGNNTSETQG DRTEQAETVQ ADLFSADSAY TFVQRQVNFG 70         80         90        100        110        120
  PRIPGTAPHR ACGDWLVATL RSFGAAVQEQ TAEIKAHDGT MLPMRNIIAS YRPEATGRML 130        140        150        160        170        180
  LMAHWDTRPV CDQDANPAMH TETFDGADDG GSGVGVLLEI ARYLGQQKDL GMGIDIVFFD 190        200        210        220        230        240
  TEDYGSYGDD ESWCLGSQYW SRNPHVAGYK AEAGILLDMV GAKGATFYWE YFSKSYAPGL 250        260        270        280        290        300
  ISAVWQTAAA LGYGNYFIQA DGGALTDDHV PVIKNLGIPC IDIINYSSKN EHGFGDHWHT 310        320        330
  QRDNMQIIDK NVLDAVGETV IRYLDEQVKA ASH
```

(D) SEQ ID NO. 2

```
          10         20         30         40         50         60
  MDRMINKYAG VLLGSLILSC CGQKNTTKEE TTEPADTDKR IEAPTFNADS AYAYIERQVA 70         80         90        100        110        120
  FGPRVPNTEA HQRCADYLAG ELDRHGAKVY VQEAVLTAYN GEKLKAQNIV GAFQPEKSRR 130        140        150        160        170        180
  VLLFAHWDSR PYADHDTDEA NHRKPIDGAD DGGSGVGILL EIARQIQAKA PAIGIDIVFF 190        200        210        220        230        240
  DAEDYGTPEF VDEYKPDTWC LGSQFWAKNP HVPNYKAEFG ILLDMVGSRG ATFYKESTSV 250        260        270        280        290        300
  QYAARYVEKV WTAARELGYG KYFINAQGGA IVDDHQYVIQ GLRTPCLDII NYDPDTQSGF 310        320        330
  GPYWHTQNDT MENIDRETLK AVGETILNVI YNH
```

FIG. 1

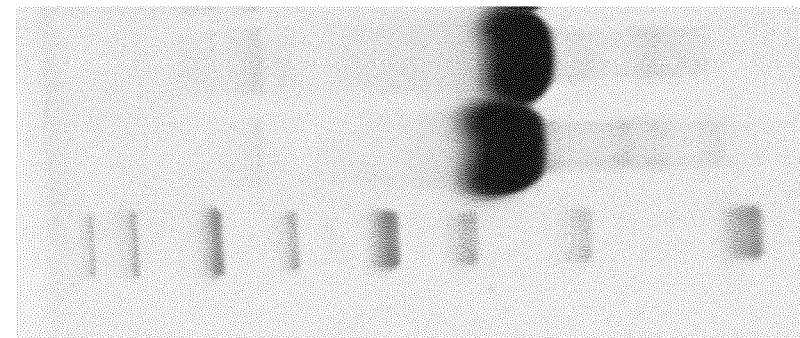
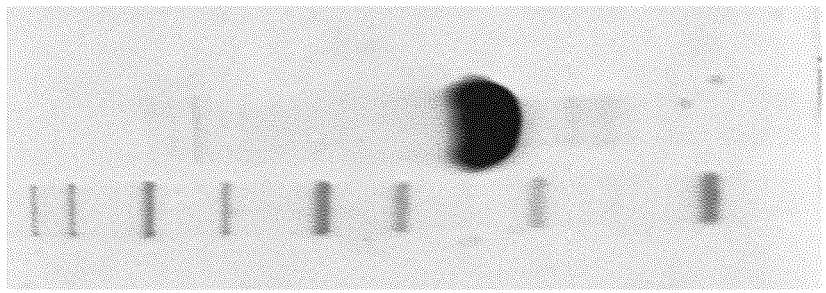
FIG. 2

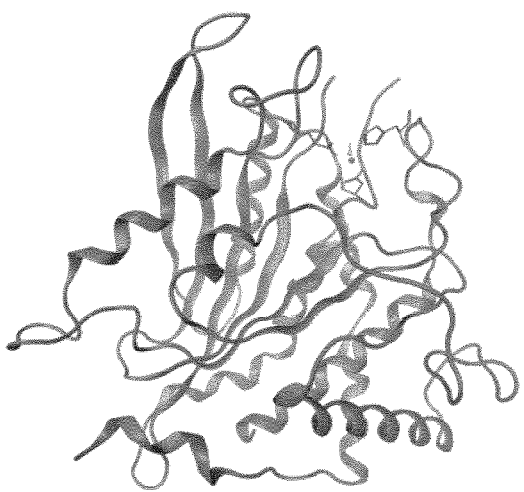
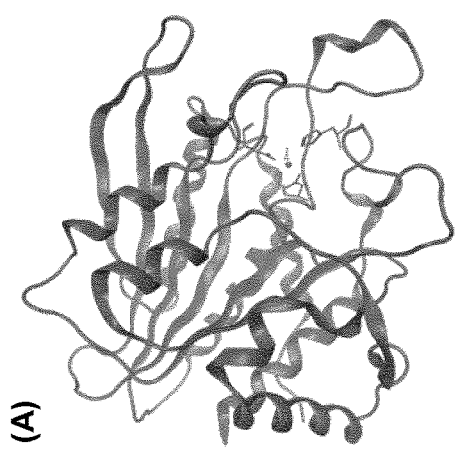
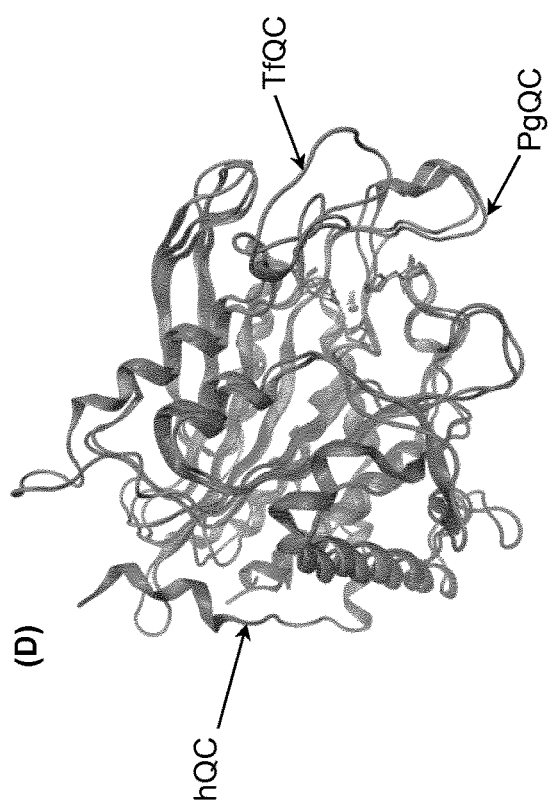
FIG. 6

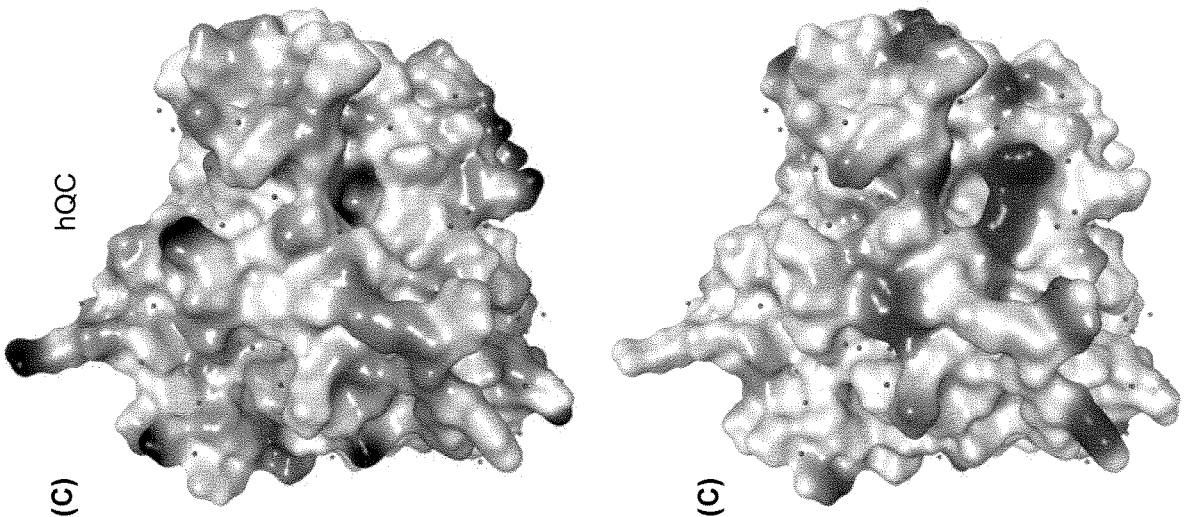
FIG. 8
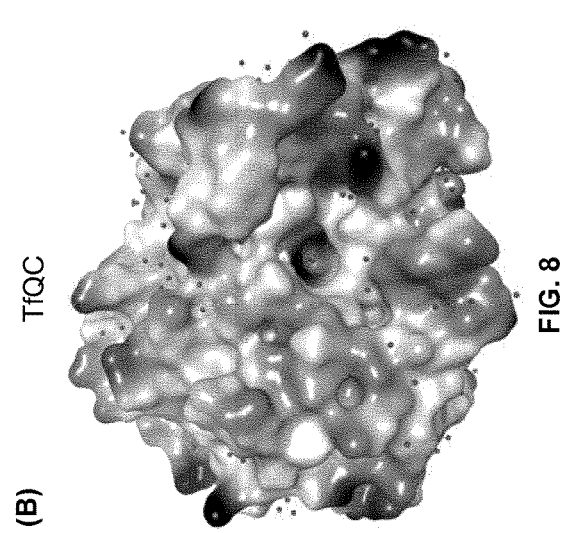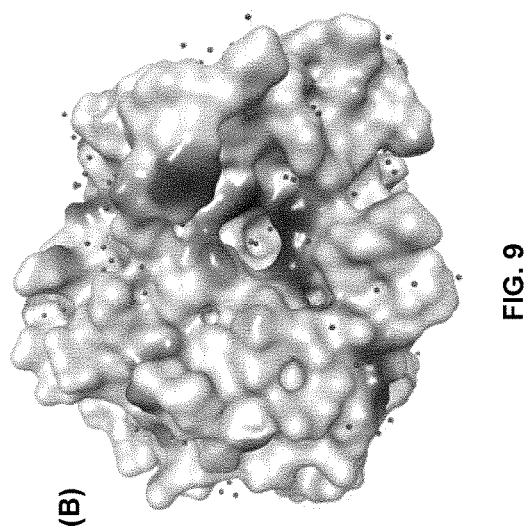
FIG. 9
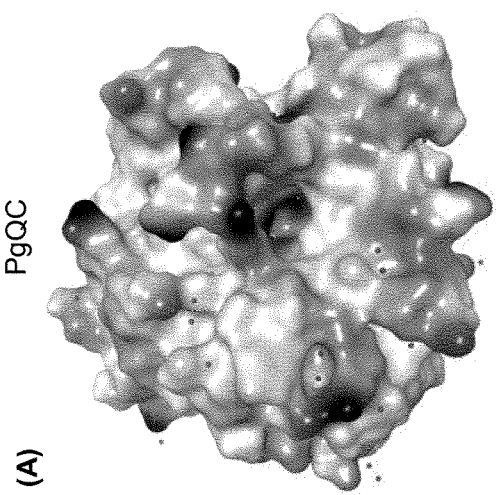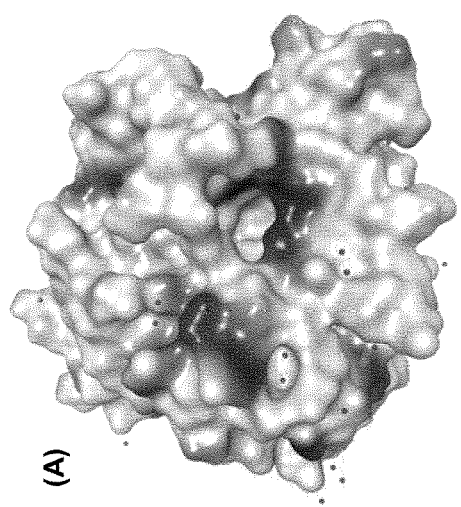

INHIBITORS OF BACTERIAL GLUTAMINYL CYCLASES FOR USE IN THE TREATMENT OF PERIODONTAL AND RELATED DISEASES

STATEMENT REGARDING SEQUENCE LISTING

The Sequence Listing associated with this application is provided in text format in lieu of a paper copy, and is hereby incorporated by reference into the specification. The name of the text file containing the Sequence Listing is SEQUENCE_LISTING_360079_402USPC. The text file is 13.8 KB, was created on Aug. 19, 2020, and is being submitted electronically via EFS-Web.

FIELD OF THE INVENTION

The present invention relates to novel compounds which are particularly useful as inhibitors of bacterial glutaminyl cyclases (bacQC); pharmaceutical compositions comprising such compounds; compounds and/or pharmaceutical compositions for use in methods for treatment, in particular for use in the treatment of periodontitis and related conditions. The present disclosure also relates to crystals comprising bacterial glutaminyl cyclases and methods for identifying candidate compounds which may associate with the binding pocket of a bacQC and/or are bacQC inhibitors.

BACKGROUND ART

Periodontal diseases are highly prevalent with about 30% of the human population being affected worldwide, have considerable impact on individuals and society, and are costly to treat. The cost of dental care is the fourth highest of all diseases and consuming between 5 and 10% of all healthcare resources (Batchelor, P. *British Dental Journal* 2014, 217, 405-409). Representative population studies show that periodontal diseases are widespread and their prevalence has been increasing since 1997 (Micheelis, W. et al. *Vierte Deutsche Mundgesundheitsstudie (DMS IV)*, Deutscher Arzte-Verlag, Köln, 2006). Amongst the adult population in Germany, 52.7% were found to be affected by moderately severe and 20.5% by severe forms of periodontitis. The health insurance expenditure in Germany for the direct treatment of periodontitis amounted to about EUR 1.1 billion (*Statistisches Bundesamt*, 2008), not including the costs incurred by secondary diseases.

Periodontitis is a general term describing inflammation condition of the periodontal apparatus which is caused by multi-bacterial induction and has strong relations to various systemic diseases, such as cardiovascular diseases, rheumatoid arthritis, chronic obstructive pulmonary disease and Alzheimer's disease.

The currently established therapy of periodontitis, according to the recommendations of the German Society Of Dental, Oral And Craniomandibular Sciences, is generally performed by manual supra and subgingival debridement (removal of the bacterial plaques) along with the application of antiseptic substances (daily disinfection by mouth washes), which disintegrates the entire oral biofilm and provides an opportunity for recolonization by potential pathogens. Furthermore, adjuvant systemic broad-spectrum antibiotic therapy is applied in advanced disease forms. The latter also leads to a non-selective destruction of the biofilm and has to be administered in high doses and over a prolonged period of time in order to reach sufficient therapeutic levels at the particular site of action, i.e. the gingival pocket. Standard adjuvant therapy of periodontitis involves, for instance, systemic administration of doxyciclin (per os) 1×200 mg/die for 1 day and 2×100 mg/die for further 18 days (Wissenschaftliche Stellungnahme: Adjuvante Antibiotika in der Parodontitistherapie, Deutsche Gesellschaft fur Zahn- Mund- und Kieferheilkunde, DZZ 2003). As a result, resistance development in oral pathogens is observed. Further, the microbiome in the patient's intestine is destroyed, which leads to a loss of metabolic support, immune modulation, and enables recolonization by potential pathogens. A focused and targeted therapy along with conservation of the remaining biofilm would represent a significant improvement in the treatment of periodontitis and conditions associated therewith.

The presence of periodontopathogenic bacteria varies among periodontitis patients. Nevertheless, the occurrence of certain bacterial species in the subgingival plaques has been found to be closely associated with the etiology of periodontal diseases (Socransky et al., *Journal of Clinical Periodontology*, 1998, 25, 134-144).

Thus, there is a high demand for the development of new treatments for periodontitis and related conditions capable of selectively targeting pathogens which induce a periodontal disease, while being essentially inactive on homologous human target proteins and preferably substantially preserving the rest of the naturally occurring biofilm. Such treatment would provide significant improvement to patients and healthcare systems.

Problems to be Solved by the Invention

In view of the above, the present invention aims at the object of identifying and providing compounds and/or pharmaceutical compositions useful in the treatment of periodontal and related diseases. Said compounds and/or pharmaceutical compositions should be preferably capable of selectively targeting pathogens which induce a periodontal disease. More preferably, the rest of the naturally occurring biofilm should be substantially preserved; homologous human target proteins should not be substantially inhibited. Even more preferably, the compounds and/or pharmaceutical compositions should exhibit high in vivo activities against the targeted pathogens.

A further object is the preparation of a crystal and/or co-crystal of therapeutic target protein(s), which can be used for identifying inhibitors capable of targeting pathogens which induce a periodontal disease, e.g., by means of structure-based drug-design.

A further object is to provide a method for identifying a candidate compound which may associate with a binding pocket of said therapeutic target protein(s), which compound is preferably an inhibitor of said therapeutic target protein.

A further object of the present invention is to provide an inhibitor of said therapeutic target protein(s), and a pharmaceutical composition comprising such inhibitor. Said inhibitor should be preferably a selective inhibitor, i.e. selectively killing or selectively inhibiting the growth of (a) target bacterial pathogen(s) while being substantially inactive towards other bacterial and/or human protein targets.

A further object of the present invention is to provide a method for treatment of the human or animal body, and/or a compound or a pharmaceutical composition for use in such method.

A further object of the present invention is to provide a method for therapy or prophylaxis of a bacterial infection, and/or a compound or a pharmaceutical composition for use in such method, preferably by selectively killing or selectively inhibiting the growth of the pathogenic bacterial species.

A further object of the present invention is to provide a method for therapy or prophylaxis of an acute, chronic or recurrent periodontal disease and/or a compound or a pharmaceutical composition compound for use in such method.

In the methods for treatment according to the above objects, the route of administration should be preferably topical administration or systemic administration, and the methods are preferably non-surgical methods.

SUMMARY OF THE INVENTION

As a solution to the above-formulated problems, the present disclosure provides a compound according to one of the following Formulae I or II,

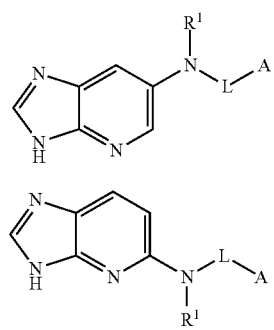

its individual enantiomers, its individual diastereoisomers, its hydrates, its solvates, its crystal forms, its individual tautomers or a pharmaceutically acceptable salt thereof, wherein L, A and $R^1$ are defined according to the appended claims.

The present disclosure further provides a pharmaceutical composition comprising the compound as defined above and a pharmaceutically acceptable excipient.

The present disclosure further provides a compound as defined above and/or a pharmaceutical composition as defined above for use in a method for treatment of the human or animal body; for use in a method for therapy and/or prophylaxis of a bacterial infection; and for use in a method for therapy and/or prophylaxis of an acute, chronic or recurrent periodontal disease.

The present disclosure further provides a crystal comprising a bacterial glutaminyl cyclase (bacQC) selected from PgQC and TfQC, and a co-crystal further comprising a candidate compound, preferably a bacQC inhibitor; as well as methods for preparing said crystal and/or co-crystal.

The present disclosure further provides methods for identifying a candidate compound which may associate with the binding pocket of the bacQC, preferably a bacQC inhibitor.

BRIEF DESCRIPTION OF THE DRAWINGS

FIG. 1 shows an amino acid sequence alignment of human QC (hQC, SEQ ID NO: 4) and putative bacterial glutaminyl cyclases (QCs, i.e. glutamine cyclotransferases) from *Porphyromonas gingivalis* (PgQC, SEQ ID NO: 1) (A); an amino acid sequence alignment of further putative QCs from *Prevotella intermedia* (PiQC, SEQ ID NO: 3), *P. gingivalis* (PgQC, SEQ ID NO: 1) and *Tannerella forsythia* (TfQC, SEQ ID NO: 2)) (B); amino acid numbering of the full-length sequence (SEQ ID NO: 1) of glutaminyl cyclase (i.e. glutamine cyclotransferase) from *P. gingivalis* (PgQC), amino acids 1-333 (C); and amino acid numbering of the full-length sequence (SEQ ID NO: 2) of glutaminyl cyclase (i.e. glutamine cyclotransferase) from *T. forsythia* (TfQC), amino acids 1-333 (D).

FIG. 2 shows SDS-PAGE of purified recombinant putative bacterial QCs expressed in *E. coli* Rosetta(DE3)pLysS.

FIG. 6 shows ribbon depiction for three glutaminyl cyclases: PgQC (A); TfQC (B); hQC (C); and overlay (D).

FIG. 8 shows molecular surfaces for PgQC (A); TfQC (B); and hQC (C) in the crystal wherein the hydrophilic areas are highlighted in darker grey (upper figures).

FIG. 9 shows molecular surfaces for PgQC (A); TfQC (B); and hQC (C) in the crystal wherein the lipophilic areas are highlighted in darker grey (lower figures).

DETAILED DESCRIPTION OF THE INVENTION

Therapeutic Target Proteins (bacQC)

Figure 3A:
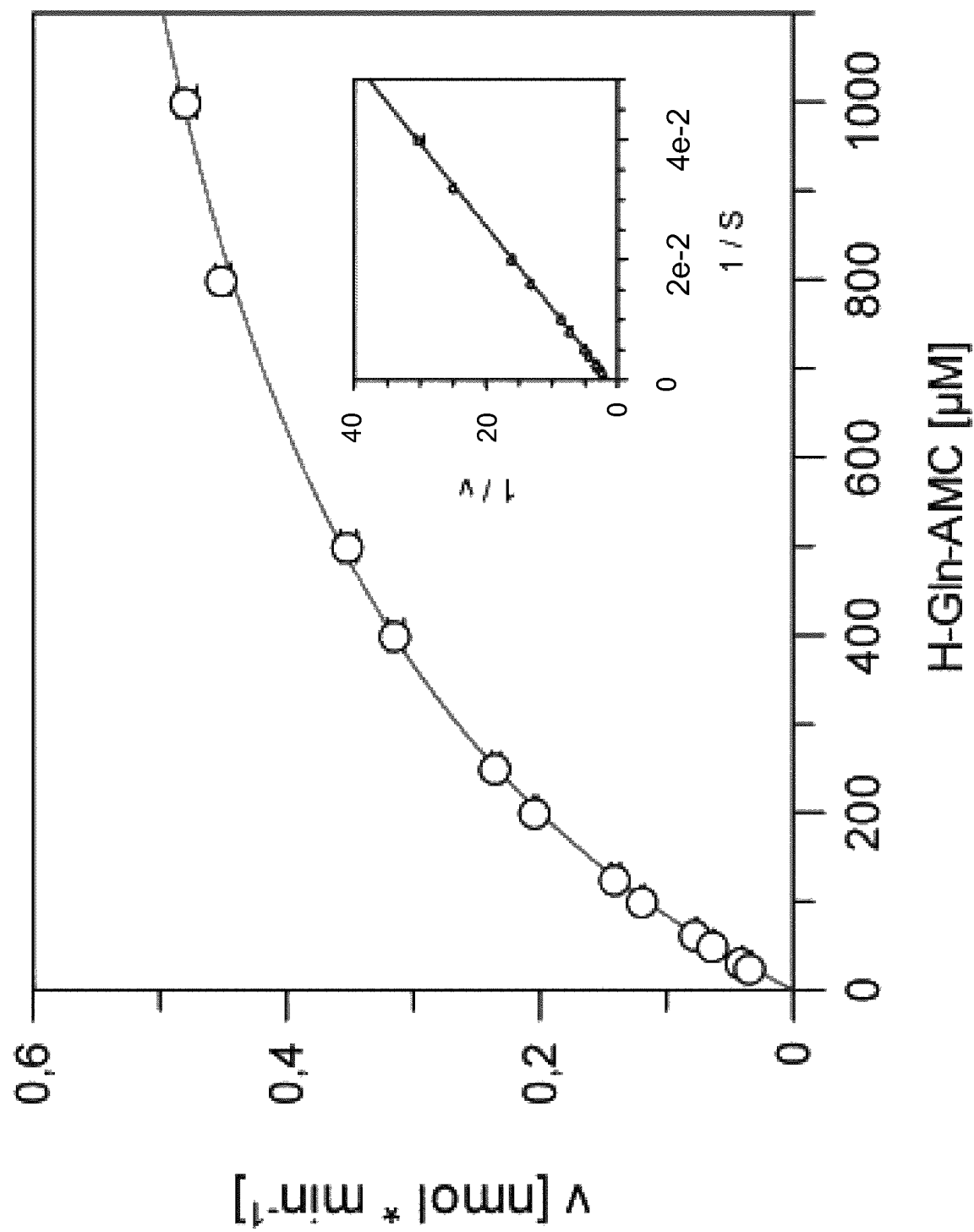
FIG. 3 shows Lineweaver-Burk plots for PgQC (A), PiQC (B) and TfQC (C) catalyzed cyclization of H-Gln-AMC.
Figure 3B:
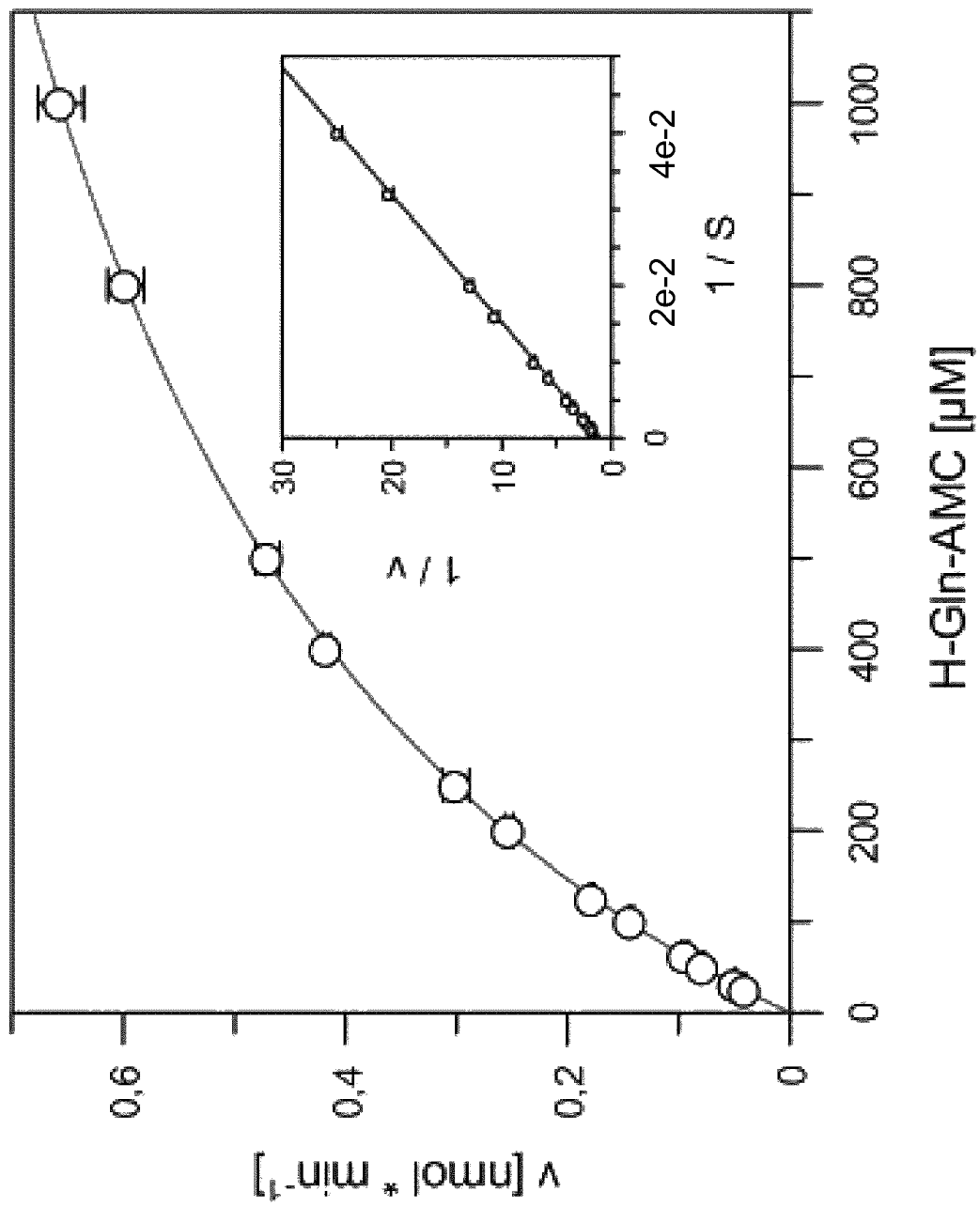

Socransky et al. (*Journal of Clinical Periodontology*, 1998, 25 134-144) described that the occurrence in subgingival plaques of a so-called "red complex" consisting of the tightly related group *Tannerella forsythia*, *Porphyromonas gingivalis* and *Treponema denticola* relates strongly to clinical measures of periodontal disease, and in particular to pocket depth and bleeding on probing.

A further related complex (so-called "orange complex") includes members of the *Fusobacterium nucleatum/periodonticum* subspecies, *Prevotella intermedia*, *Prevotella nigrescens* and *Peptostreptococcus micros*. Colonization of healthy periodontal sites by members of the "orange complex" was found to correlate with the occurrence of gingivitis. The bacteria of the "orange complex" furthermore promote the colonization by bacteria of the "red complex", which in turn are associated with deep pockets and chronic periodontitis.

Bacteria of the "red complex" and the "orange complex" secrete a variety of virulence factors. For instance, it was found that *P. gingivalis* secretes cysteine proteases such as gingipain, *P. intermedia* secretes salivary IgA proteases, and *T. forsythia* secretes glycosidases.

The present inventors found surprisingly that about 80% of the secreted proteins bearing a signal peptide in the secretome of the oral pathogens *P. gingivalis*, *T. forsythia*, and *P. intermedia* are cleaved at a Xaa-Gln peptide bond by a signal peptidase. The N-termini of the released proteins contain a pGlu-residue. This implies the existence of glutaminyl cyclases which seem to be essential for growth protein translocation across outer membrane and the growth of said periodontal pathogens.

Glutaminyl cyclases (QCs) (EC 2.3.2.5), also referred to as glutamine cyclotransferases, are acyltransferases that catalyze the cyclization of N-terminal glutaminyl residues of proteins to pyroglutamate (pGlu) under release of NH₃, thus modifying the N-terminus of the peptides:

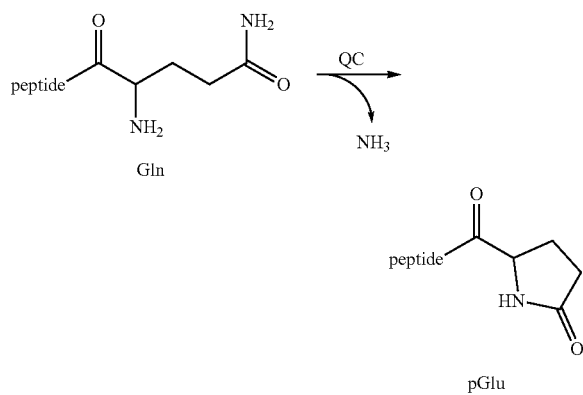

Two types of QCs (Type I and Type II) have been defined so far. Type I QCs were found in plants and in several pathogenic bacteria and human parasites (Huang et al., *J. Mol. Biol.* 2010, 401, 374-388). *Papaya* QC (pQC) is the best-known Type I QC. This enzyme was first discovered in the latex of the tropical plant *Carica papaya* (Messer, M. Nature 1963, 197, 1299). The enzyme exhibits catalytic activity over a broad pH range (pH 3.5-11). X-ray crystallographic analyses revealed that pQC is a hatbox-shaped molecule, consisting of a five-bladed β-propeller traversed by a central channel (Wintjens, R., Belrhali, H., Clantin, B., Azarkan, M., Bompard, C., Baeyens-Volant, D., Looze, Y., and Villeret, V. *J. Mol. Biol.* 2006, 357, 457-470). pQC contains a zinc ion but is not inhibited at all by heterocyclic chelators (Zerhouni et al., *Biochim. Biophys. Acta* 1998, 1387, 275-290), and it is therefore assumed that the zinc has only a structural and stabilizing function. pQC is highly resistant to proteolytic, chemical, and thermal denaturations (Wintjens et al., Zerhouni et al.)

Type II QCs were mainly identified in the neuroendocrine tissues of mammals. Among Type II QCs, the human QC (hQC) is the most extensively studied one, which is known to be important in the maturation of numerous neuropeptides and cytokines in their secretory pathways. In contrast to Type I QCs, hQC is quite susceptible to chemical and thermal denaturation. Schilling et al., 2003 (*J. Biol. Chem.* 2003, 278, 49773-49779) have shown that hQC was significantly unstable above pH 8.5 and below pH 6.0. hQC adopts an α/β topology (Huang et al. *Proc. Natl Acad. Sci. USA*, 2005, 102, 13117-13122) and was identified as a metalloenzyme, as suggested by the time-dependent inhibition by the heterocyclic chelators. Inactivated enzyme can be fully restored by the addition of $Zn^{2+}$ in the presence of equimolar concentrations of EDTA (Schilling et al., 2003). Thus, Type II QCs are metal-dependent transferases, suggesting that the active site bound metal ($Zn^{2+}$) is essential for the catalytic activity, in contrast to the Type I QCs, wherein zinc has only a structural and stabilizing function.

In summary, Type I QCs are generally found in plants, several bacteria and protozoa; they exhibit β-propeller structures; high resistance against proteolysis, heat, and acid; the optimal catalytic activity is at pH 3.5-11; and possess a structural $Ca^{2+}/Zn^{2+}$ ion.

In contrast, Type II QCs are mainly found in vertebrates; they exhibit α/β-topologies; low resistance against proteolysis, heat, and acid; the optimal catalytic activity is at pH 6.0-8.0; and there is catalytically essential $Zn^{2+}$ ion. Thus, Type II glutaminyl cyclases are zinc-dependent acyltransferases.

The present inventors surprisingly found that Type II QCs are expressed in the oral pathogens *P. gingivalis, T. forsythia*, and *P. intermedia*.

The primary structure of the QC protein from *P. gingivalis* (PgQC, SEQ ID NO: 1) has a 25% identity to human QC (hQC, SEQ ID NO: 4). Furthermore, QC from *P. intermedia* (PiQC, SEQ ID NO: 3) and *T. forsythia* (TfQC, SEQ ID NO: 2) were identified, which share an identity to PgQC of 42% and 49%, respectively. Further experimental evidence shows that these enzymes indeed belong to the Type II QC family, as confirmed inter alia by pH and ionic strength dependency of the bacQC activity, the inhibition of the QC activity by metal chelators, the folding patterns of all three proteins suggesting an α/β topology as indicated by the CD spectroscopic analysis, and their thermal stability.

The present inventors found that bacterial Type II QCs are expressed in and are essential for the growth of 2 out of 3 periodontitis-causing bacterial species of the "red complex", as well as at least one bacterial species of the "orange complex", and are therefore of crucial importance for as a target for the development of a therapeutic inhibitor with antibiotic properties for the treatment of periodontitis diseases and conditions.

Thus, in the context of the present, the therapeutic target proteins are bacterial glutaminyl cyclases (bacQCs), wherein a bacQC is defined as a polypeptide comprising an amino acid sequence selected from the group consisting of SEQ ID NO: 1 (also referred to as PgQC), SEQ ID NO: 2 (also referred to as TfQC), SEQ ID NO: 3 (also referred to as PiQC), and an amino acid sequence having a sequence identity of 90% or more to any one of SEQ ID NO:1, SEQ IDNO:2 and SEQ IDNO:3.

bacQCs can be identified, isolated and purified and used to identify inhibitors capable of selective targeting of periodontitis-inducing pathogens as further described in the examples herein. For the purposes of comparing two or more amino acid sequences, the degree of identity between two amino acid sequences (percentage of "sequence identity") can be determined by conventional methods, for example, by means of standard sequence alignment algorithms known in the state of the art, such as, for example BLAST (Altschul S. F. et al. *J Mol Biol.* 1990, 215(3), 403-10).

Compounds

By using the methods for identifying candidate compounds and/or inhibitors disclosed herein, the present inventors have now identified a novel group as a lead structural motif for the design and preparation of potent and therapeutically effective inhibitors of bacterial glutaminyl cyclases. Said structural motif is a imidazo[4,5-b]pyridine group as shown below (including the numbering of the ring atoms):

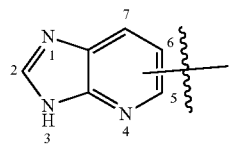

This structural motif represents a suitable metal binding group capable of reversibly binding to the $Zn^{2+}$ ion located in the binding pocket of the bacQCs. Preferably, when the imidazo[4,5-b]pyridine group is substituted at the 6-position of the pyridine ring, a particularly high bacQC inhibitory activity and selectivity can be attained.

More preferably, the group bound to the imidazo[4,5-b]pyridine group is either a benzyl amine or an aromatic sulfonamide, each bound via the N atom to the pyridine ring. In contrast, it was found that using aromatic amides instead provides a weak activity, and these are therefore less preferred. In other words, $R^a$ and $R^b$ preferably do not represent together =O.

In a further preferred embodiment, the compounds comprise a moiety represented by the following structure E:

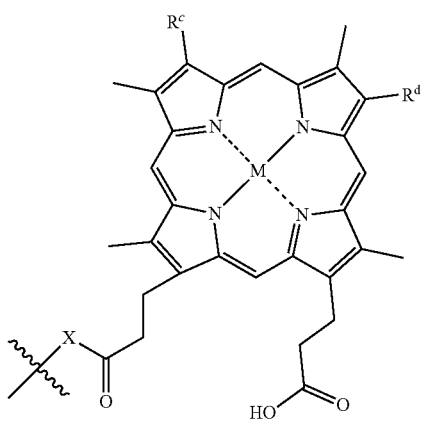

The presence of this moiety enhances the uptake of the inhibitor compounds according to the present invention into the cells of bacteria expressing Type II glutaminyl cyclases (such as *P. gingivalis*, *T. forsythia* and *P. intermedia*) which recognize, actively uptake and capture the above porphyrin moiety by means a metal-independent system (e.g., HA2 domain, which is a receptor for both haem and haemoglobin) and/or metal-dependent system (e.g., HusA, which is a haemophore-like porphyrin binding protein capable of recognizing the above group). Thus, conjugating an inhibitor of the general Formula I or II with a moiety represented by structure E provides enhanced, directed delivery to the pathogen cells, improved selectivity for the target oral pathogens, and/or improved in vivo antibiotic activity against these pathogens. These effects are particularly pronounced when a moiety represented by structure E is attached to group A of the inhibitor via a linker represented by structure E, as defined in the appended claims.

Specifically, the present disclosure provides compounds to any one of the following aspects <1>-<19>.

<1> A compound according to one of the following Formulae I or II,

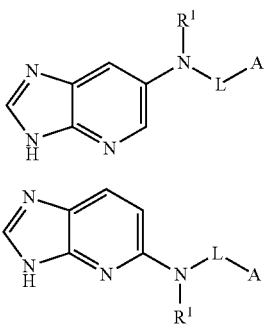

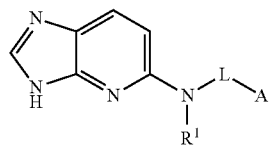

its individual enantiomers, its individual diastereoisomers, its hydrates, its solvates, its crystal forms, its individual tautomers or a pharmaceutically acceptable salt thereof, wherein:

A is selected from the group consisting of optionally substituted aryl, optionally substituted heterocyclyl, optionally substituted cycloalkyl and optionally substituted alkenyl;

$R^1$ is independently selected from the group consisting of H and optionally substituted alkyl;

L is selected from

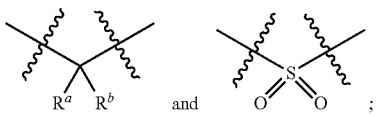

$R^a$ and $R^b$ are the same or different from each other and are independently selected from the group consisting of H, halo, optionally substituted alkyl, optionally substituted aryl, optionally substituted heteroalkyl and optionally substituted heteroaryl, and wherein $R^a$ and $R^b$ can optionally be joined together to form a carbocyclic or a heterocyclic ring.

<2> The compound according to of aspect <1>, wherein:
said aryl is independently a $C_{6-10}$, preferably $C_6$ aryl group;
said heterocyclyl is independently a monocyclic or bicyclic, $C_{1-11}$, preferably $C_{2-8}$, more preferably $C_{4-5}$ heterocyclic group comprising 1 to 4 ring heteroatoms selected from N, S and O;
said alkyl is independently a linear or branched, open-chained or cyclic $C_{1-6}$, preferably $C_{1-4}$, more preferably $C_{1-3}$, even more preferably $C_{1-2}$ alkyl group;
said cycloalkyl is independently a cyclic $C_{3-6}$, preferably $C_{4-6}$, more preferably $C_{5-6}$ alkyl group;
said alkenyl is independently a linear or branched, open-chained or cyclic $C_{2-6}$, preferably $C_{2-4}$, more preferably $C_2$ group comprising at least one C=C bond;
said heteroaryl is independently an aromatic, monocyclic or bicyclic, $C_{1-11}$, preferably $C_{2-8}$, more preferably $C_{4-5}$ heterocyclic group comprising 1 to 4 ring heteroatoms selected from N, S and O; and
said heteroalkyl is independently a linear or branched, open-chained or cyclic $C_{1-5}$, preferably $C_{1-3}$, more preferably $C_{1-2}$ heteroalkyl group comprising 1 to 4 heteroatoms selected from N, S and O.

<3> The compound according to any one of aspects <1> to <2>, which is represented by one the following formulae Ia, IIa, Ib and IIb, preferably Ia:

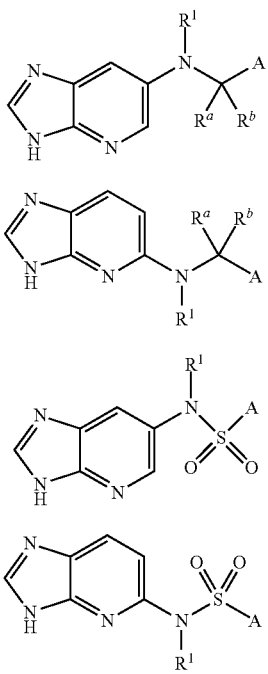

Ia

IIa

Ib

IIb wherein A is selected from optionally substituted aryl and optionally substituted heteroaryl; and
R¹, Rᵃ and Rᵇ are H.

<4> The compound according to any one of aspects <1> to <3>, wherein Rᵃ and Rᵇ are independently selected from ¹H and D.

<5> The compound according to any one of aspects <1> to <4>, wherein either one of Rᵃ and Rᵇ is ¹H and the other one is D; or each of them is ¹H; or each of them is D.

<6> The compound according to any one of aspects <1> to <5>, wherein:
A is represented by one of the following structures A-1 to A-7;

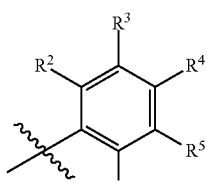

A-1

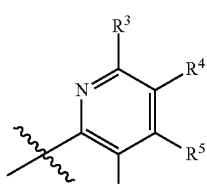

A-2

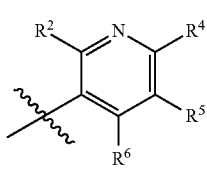

A-3

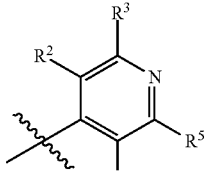

A-4

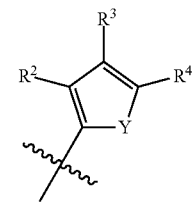

A-5

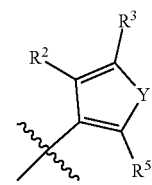

A-6

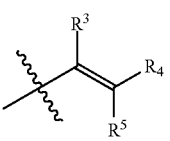

A-7 wherein Y is selected from O and S; and
R² to R⁶ are each independently selected from the group consisting of H, fluoro, chloro, bromo, iodo, alkyl, aryl, heteroaryl, alkoxy, aryloxy, (aminoalkyl)oxy, (heteroaryl)oxy, amino, (dialkyl)amino, (monoalkyl)amino, (alkyl)(heteroalkyl)amino, (diheteroalkyl)amino, [(alkyl)oxy]carbonyl and haloalkyl, each of which can optionally be further substituted.

<7> The compound according to aspect <6>, wherein either:
(a) R⁴, or
(b) R³, or
(c) R³ and R⁴
is/are each independently selected from the group consisting of fluoro, chloro, bromo, iodo, alkyl, aryl, heteroaryl, alkoxy, aryloxy, (aminoalkyl)oxy, (heteroaryl)oxy, amino, (dialkyl)amino, (monoalkyl)amino, (alkyl)(heteroalkyl)amino, (diheteroalkyl)amino, [(alkyl)oxy]carbonyl and haloalkyl, each of which can optionally be further substituted;
and the remaining ones of R² to R⁶ are H.

<8> The compound according to any one of aspects <6> to <7>, wherein
at least one of R², R³, R⁴, R⁵ and R⁶ is independently represented by the following structure B:

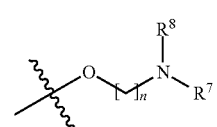

B wherein n=1, 2, 3, 4, 5 or 6;
R⁷ and R⁸ are independently selected from alkyl, aryl, heteroalkyl, heteroaryl, carbamimidoyl, formyl, alkylacyl and arylacyl, each of optionally be further substituted and wherein R⁷ and R⁸ can be optionally joined together to form a carbocyclic or a heterocyclic ring.

<9> The compound according to any one of aspects <6> to <8>, wherein:
R¹, $R^a$ and $R^b$ are H; and
A is represented by the structure A-1.

<10> The compound according to any one of aspects <1> to <7>, wherein A is substituted by at least one substituent represented by the following structure B:

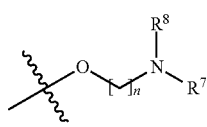

B wherein n=1, 2, 3, 4, 5 or 6; and
R⁷ and R⁸ are independently selected from alkyl, aryl, heteroalkyl, heteroaryl, carbamimidoyl, formyl, alkylacyl and arylacyl, each of which can optionally be further substituted and wherein R⁷ and R⁸ can be optionally joined together to form a carbocyclic or a heterocyclic ring.

<11> The compound according to any one of aspects <8> to <10>, wherein R⁷ is represented by the following structure E:

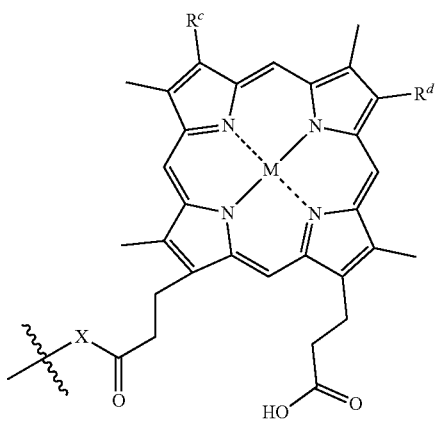

E wherein M is selected from $Fe^{2+}$ and $Fe^{3+}$ or is absent;
$R^c$ and $R^d$ are independently selected from —H, —CH₃, —CH=CH₂, —S₃H and —CH(OH)CH₂OH; and
X is selected from a covalent bond, an alkylene, aralkylene, heteroalkylene, carbocyclene, heterocyclene, heteroarylene, heteroaralkylene, aminoalkylene, alkylamino and carbonyl-alkylamino group; wherein each of these may have up to 12 carbon atoms and up to 11 heteroatoms in the main chain, and may be substituted by one or more $C_{1-6}$ alkyl group(s), $C_{1-6}$ heteroalkyl group(s), $C_{1-6}$ carbocyclyl group(s), $C_{1-5}$ heterocyclyl group(s), $C_{1-5}$ heteroaryl group(s), halogen atom(s), hydroxyl group(s), cyano group(s), primary, secondary or tertiary amino group(s), carboxyl group(s) and side chain(s) derived from proteinogenic or non-proteinogenic aminoacid(s).

<12> The compound according to aspect <11>, wherein X is represented by the following structure:

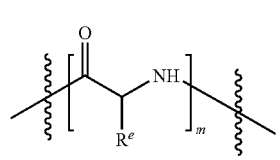

X wherein m=0, 1, 2 or 3, and
$R^e$ is a side chain derived from a proteinogenic amino acid.

<13> The compound according to any one of aspects <1> to <12>, wherein A is substituted by a substituent represented by the following structure F:

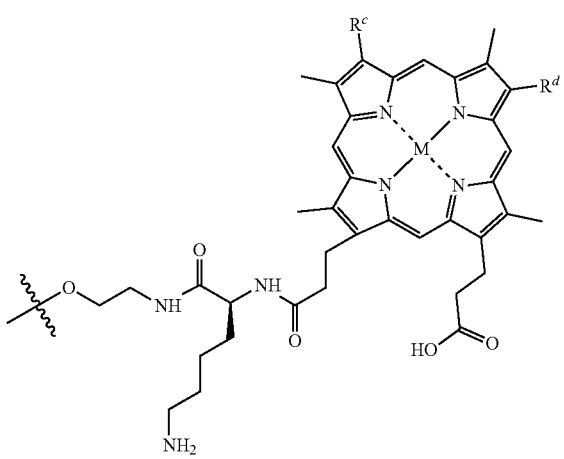

F wherein M is selected from $Fe^{2+}$ and $Fe^{3+}$ or is absent; and
$R^c$ and $R^d$ are independently selected from —H, —CH₃, —CH=CH₂, —S₃H and —CH(OH)CH₂OH.

<14> The compound according to aspect <13>, wherein A is as defined according to aspect <6>, and wherein at least one of R², R³, R⁴, R⁵ and R⁶ is represented by the structure F.

<15> The compound according to any one of aspects <1> to <14>, wherein A is substituted by at least one substituent represented by the following structure E1:

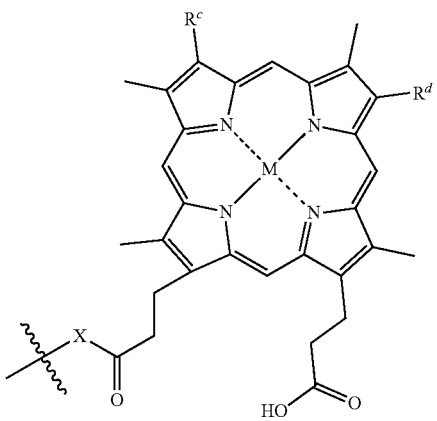

E1 wherein M is selected from $Fe^{2+}$ and $Fe^{3+}$ or is absent;

$R^c$ and $R^d$ are independently selected from —H, —CH$_3$, —CH=CH$_2$, —SO$_3$H and —CH(OH)CH$_2$OH; and X is selected from a covalent bond, O, NH, an alkylene, aralkylene, heteroalkylene, carbocyclene, heterocyclene, heteroarylene, heteroaralkylene, aminoalkylene, alkylamino and carbonyl-alkylamino group; wherein each of these may have up to 12 carbon atoms and up to 11 heteroatoms in the main chain, and may be substituted by one or more $C_{1-6}$ alkyl group(s), $C_{1-6}$ heteroalkyl group(s), $C_{1-6}$ carbocyclyl group(s), $C_{1-5}$ heterocyclyl group(s), $C_{1-5}$ heteroaryl group(s), halogen atom(s), hydroxyl group(s), cyano group(s), primary, secondary or tertiary amino group(s), carboxyl group(s) and side chain(s) derived from proteinogenic or non-proteinogenic aminoacid(s).

<16> The compound according to any one of aspects <1> to <15>, wherein

A is selected from the group consisting of alkoxyaryl, (alkoxy)(halo)aryl, (alkoxy)heteroaryl, alkylaryl, alkylheteroaryl, aminoaryl, aminoheteroaryl, arylaryl, arylheteroaryl, (aryloxy)aryl, (aryloxy)heteroaryl, haloaryl, haloheteroaryl, (heteroalkyl)aryl, (haloalkyl)aryl, (heteroaryl)aryl, [(heteroaryl)oxy]aryl, [(aminoalkyl)oxy]aryl, aryl, heteroaryl, cycloalkyl and heterocloalkyl, each of which can optionally be further substituted.

<17> The compound according to any one of aspects <1> to <16>, wherein:

A is selected from the group consisting of 2-alkoxyphenyl, 3-alkoxyphenyl, 4-alkoxyphenyl, 2,3-dialkoxyphenyl, 2,4-dialkoxyphenyl, 2,5-dialkoxyphenyl, 2,6-dialkoxyphenyl, 3,4-dialkoxyphenyl, 3,5-dialkoxyphenyl, 3,4,5-trialkoxyphenyl, 2,6-dihalo-4-alkoxyphenyl, 2-halo-4-alkoxyphenyl, 3-halo-5-alkoxyphenyl, 4-halo-3-alkoxyphenyl, 2-alkylphenyl, 3-alkylphenyl, 4-alkylphenyl, 3-[(alkyl)(heteroalkyl)amino]phenyl, 3-[(dialkyl)amino]phenyl, 3-[(diheteroalkyl)amino]phenyl, 3-[(monoalkyl)amino]phenyl, 4-[(alkyl)(heteroalkyl)amino]phenyl, 4-[(dialkyl)amino]phenyl, 4-[(diheteroalkyl)amino]phenyl, 4-[(heteroaryl)oxy]phenyl, 4-[(monoalkyl)amino]phenyl, arylphenyl, 2-(aryloxy)phenyl, 3-(aryloxy)phenyl, 4-(aryloxy)phenyl, 2-halophenyl, 3-halophenyl, 4-halophenyl, 2,3-dihalophenyl, 2,4-dihalophenyl, 2,5-dihalophenyl, 2,6-dihalophenyl, 3,4-dihalophenyl, 3,5-dihalophenyl, 2,3,4-trihalophenyl, 2,3,5-trihalophenyl, 3,4,5-trihalophenyl, 2,4,5-trihalophenyl, 2,4,6-trihalophenyl, 3-(haloalkyl)phenyl, 4-(haloalkyl)phenyl, 3-($C_5$ monoheteroaryl)phenyl, 4-($C_5$ monoheteroaryl)phenyl, 3-($C_4$ monoheteroaryl)phenyl, 4-($C_4$ monoheteroaryl)phenyl, 3-[(heteroaryl)oxy]phenyl, 4-{[amino(alkyl)]oxy}phenyl, 3-{[amino(alkyl)]oxy}phenyl, naphthyl, phenyl, $C_5$ monoheteroaryl, $C_4$ monoheteroaryl, morpholinyl and piperidinyl, each of which can optionally be further substituted.

<18> The compound according to any one of aspects <1> to <17>, wherein:

A is selected from the group consisting of 2-methoxyphenyl, 3-methoxyphenyl, 4-propoxyphenyl, 4-methoxyphenyl, 4-isopropoxyphenyl, 4-benzyloxyphenyl, 3,4-dimethoxyphenyl, 2,3-dihydro-1,4-benzodioxin-6-yl, 2,2-difluoro-1,3-benzodioxol-5-yl, 7-methoxy-1,3-benzodioxol-5-yl, 2,6-difluoro-4-methoxy-phenyl, 3-(1-piperidyl)phenyl, 4-morpholinophenyl, [1,1'-biphenyl]-3-yl, [1,1'-biphenyl]-4-yl, 3-phenoxyphenyl, 4-phenoxyphenyl, 2-chlorophenyl, 3-chlorophenyl, 4-chlorophenyl, 3,4-dichlorophenyl, 3,4,5-trifluorophenyl, 4-(2-pyridyl)phenyl, 4-(2-carbamimidamidoethyloxy)phenyl, 4-(2-aminoethoxy)phenyl, 4-(2-morpholinoethoxy)phenyl, phenyl, 2-pyridyl, 3-pyridyl, 4-pyridyl, 2-thienyl and 3-thienyl.

<19> A compound selected from the group consisting of:

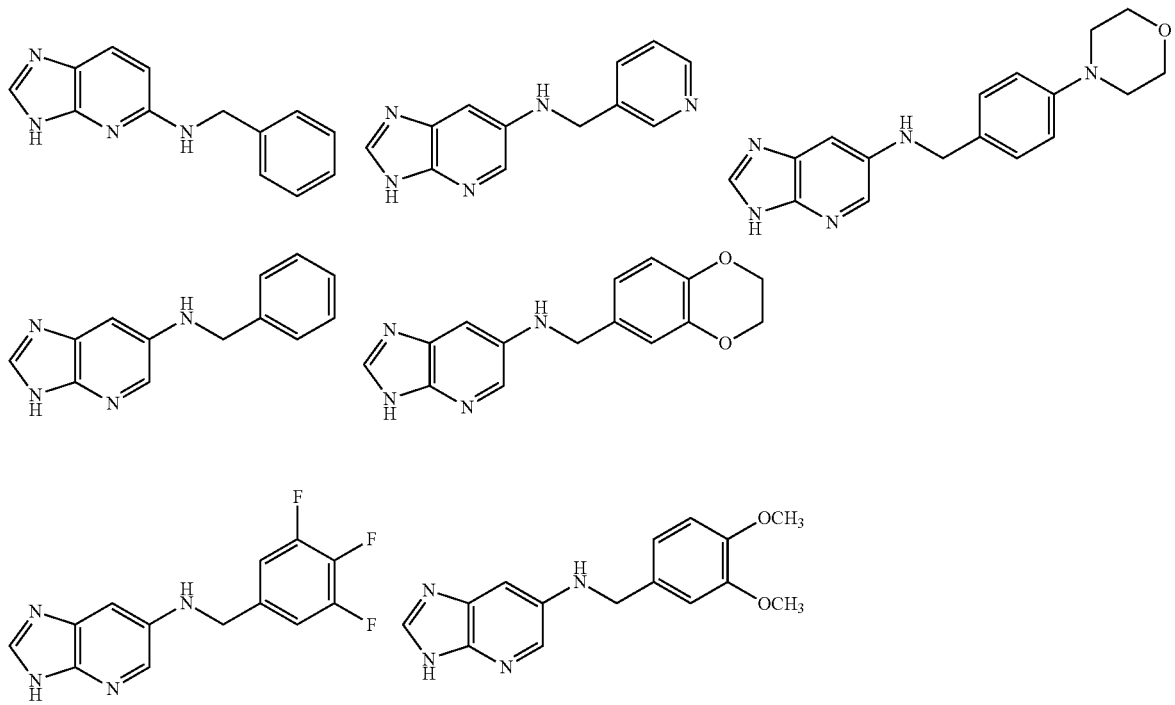

-continued
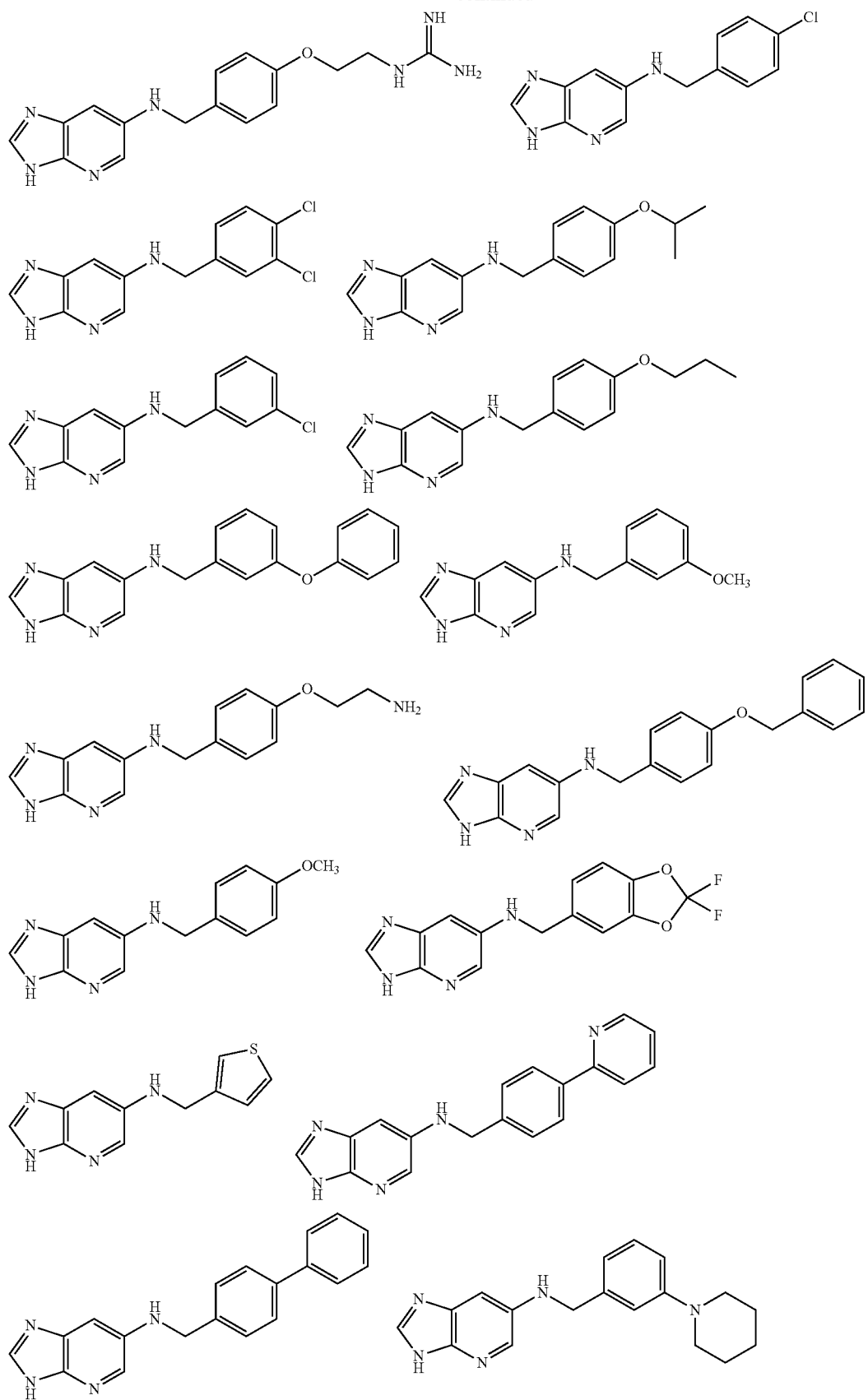

-continued

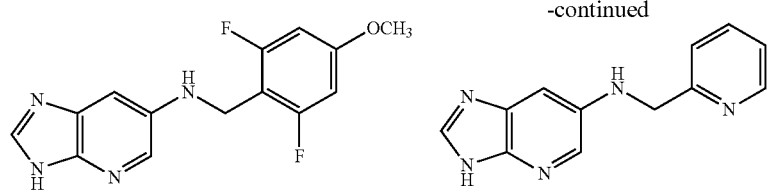

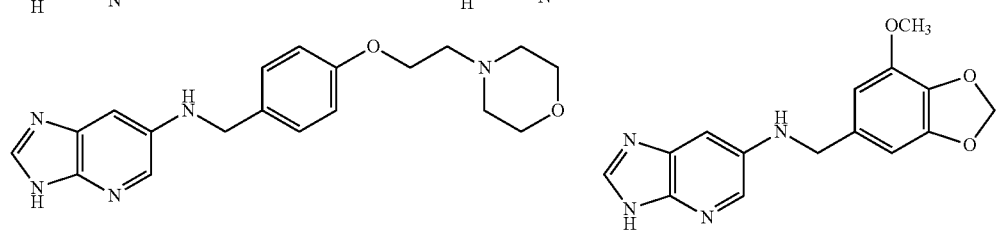

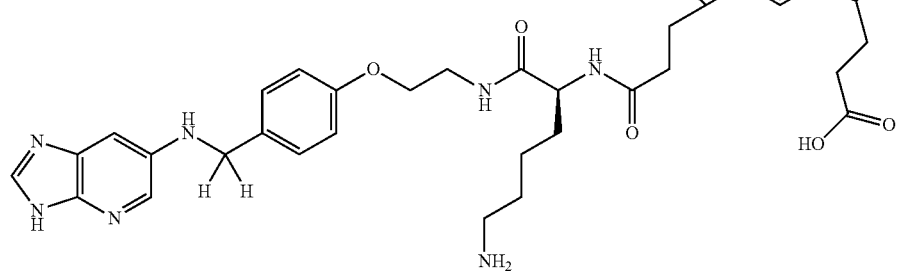

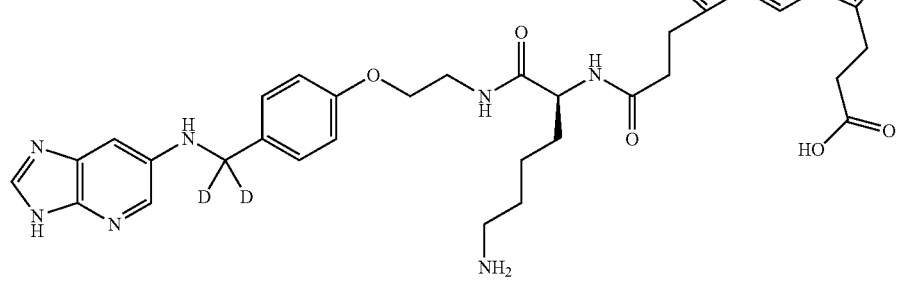

The expression "alkyl" as used herein, unless specifically limited, denotes a $C_{1-12}$ alkyl group, suitably a $C_{1-8}$ alkyl group, e.g. $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g. n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The term "alkyl" also comprises cycloalkyl groups. The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "heteroalkyl", unless specifically limited, refers to an alkyl group wherein one or more carbon atoms, preferably 1, 2 or 3, are replaced by heteroatoms selected from N, S and O.

The expressions "carbocyclyl" and "carbocyclic", unless specifically limited, denote any ring system in which all the ring atoms are carbon and which contains between three and twelve ring carbon atoms, suitably between three and ten carbon atoms and more suitably between three and eight carbon atoms. Carbocyclyl groups may be saturated or partially unsaturated, but do not include aromatic rings. Examples of carbocyclyl groups include monocyclic, bicyclic, and tricyclic ring systems, in particular monocyclic and bicyclic ring systems. Other carbocyclyl groups include bridged ring systems (e.g. bicyclo[2.2.1]heptenyl). A specific example of a carbocyclyl group is a cycloalkyl group. A further example of a carbocyclyl group is a cycloalkenyl group.

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). An example of a typical aryl group with one aromatic ring is phenyl. An example of a typical aryl group with two aromatic rings is naphthyl.

The expressions "heterocyclyl" and "heterocyclyc", unless specifically limited, refer to a carbocyclyl group wherein one or more (e.g. 1, 2 or 3) ring atoms are replaced by heteroatoms selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Heteroaryl groups represent a particular subtype within the general class of "heterocyclyl" or "heterocyclyc" groups. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); six membered rings (e.g. pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g. indol-6-yl), benzofuran, benzothiophene, quinoline, isoquinoline, indazole, benzimidazole, benzothiazole, quinazoline and purine.

The expressions "alkoxyaryl", "carboxyaryl", "cyanoaryl", "haloaryl", "hydroxyaryl" and "heteroarylaryl", unless specifically limited, denote an aryl residue which is substituted by at least one alkoxy, carboxy, cyano, halo, hydroxy and heteroaryl group, respectively.

The expressions "alkoxyheteroaryl", "carboxyheteroaryl", "cyanoheteroaryl", "haloheteroaryl" and "hydroxyheteroaryl", unless specifically limited, denote a heteroaryl residue which is substituted by at least one alkoxy, carboxy, cyano, halo, and hydroxy group, respectively.

The expression "alk", for example in the expressions "alkoxy", "haloalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary haloalkyl groups include fluoroalkyl e.g. $CF_3$; exemplary haloalkoxy groups include fluoroalkyl e.g. $OCF_3$.

The term "halogen" or "halo" comprises fluorine (F), chlorine (Cl), bromine (Br) and iodine (I).

The terms "hydrogen" or "H" as used herein encompass all isotopes of hydrogen, in particular protium ($^1H$) and deuterium ($^2H$, also denoted as D)

The term "optionally substituted" refers to optional substitution by one or several groups independently selected from: $C_{1-6}$ alkyl, $C_{1-6}$ heteroalkyl, $C_{1-6}$ carbocyclyl, $C_{1-5}$ heterocyclyl and $C_{1-5}$ heteroaryl group, each of which may be substituted by one or several halogen atoms and/or hydroxyl groups; a halogen atom; a cyano group; a primary, secondary or tertiary amino group; a hydroxyl group; and a carboxyl group.

Stereoisomers

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base, or by salt formation with an optically active base, such as quinine, quinidine, quinotoxine, cinkotoxine, (S)-phenylethylamine, (1R,2S)-ephedrine, (R)-phenylglycinol, (S)-2-aminobutanol, followed by fractional crystallization and regeneration of the free acid. The compounds may also be resolved by formation of diastereomeric esters or amides, followed by chromatographic separation and removal of the chiral auxiliary. Alternatively, the compounds may be resolved using a chiral HPLC column.

Polymorph Crystal Forms, Solvates, Hydrates

Furthermore, some of the individual crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization. In view of the close relationship between the free compounds and the compounds in the form of their salts, hydrates or solvates, whenever a compound is referred to in this context, a corresponding salt, solvate or polymorph is also intended, provided such is possible or appropriate under the circumstances.

Tautomers

As used herein, the term "tautomer" refers to the migration of protons between adjacent single and double bonds. The tautomerization process is reversible. Compounds described herein can undergo any possible tautomerization that is within the physical characteristics of the compound.

Pharmaceutically Acceptable Salts

As used herein, the term "pharmaceutically acceptable" embraces both human and veterinary use. For example, the term "pharmaceutically acceptable" embraces a veterinarily acceptable compound or a compound acceptable in human medicine and health care.

Salts, hydrates and solvates of the compounds of Formula I and physiologically functional derivatives thereof which are suitable for use in medicine are those wherein the counter-ion or associated solvent is pharmaceutically acceptable. However, salts, hydrates and solvates having non-pharmaceutically acceptable counter-ions or associated solvents are within the scope of the present invention, for example, for use as intermediates in the preparation of other compounds and their pharmaceutically acceptable salts, hydrates and solvates.

Suitable salts according to the invention include those formed with either organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalenes-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of the present invention.

Pharmaceutical Compositions

The pharmaceutical composition according to the present invention comprises a compound as described above and a pharmaceutically acceptable excipient.

As used herein, the term "pharmaceutical composition" is intended to encompass a product comprising the claimed compounds in the therapeutically effective amounts, as well as any product that results, directly or indirectly, from combinations of the claimed compounds. As used herein, the term "excipient" refers to a carrier, a binder, a disintegrator and/or a further suitable additive for galenic formulations, for instance, for liquid oral preparations, such as suspensions, elixirs and solutions; and/or for solid oral preparations, such as, for example, powders, capsules, gelcaps and tablets. Carriers, which can be added to the mixture, include necessary and inert pharmaceutical excipients, including, but not limited to, suitable suspending agents, lubricants, flavorants, sweeteners, preservatives, coatings, granulating agents, dyes, and coloring agents.

Therapeutic Applications

The present disclosure provides a compound, e.g., a compound any one of the above aspects <1>-<19>, and/or a pharmaceutical composition as described above for use in a method for treatment of the human or animal body. The present disclosure also provides a method for treatment of the human or animal body wherein the method comprises administration of a therapeutically effective amount of said compound or composition to a subject in need thereof.

The present disclosure further provides a compound and/or a pharmaceutical composition as described above for use in a method for therapy or prophylaxis of a bacterial infection. The present disclosure also provides a method for therapy or prophylaxis of a bacterial infection wherein the method comprises administration of a therapeutically effective amount of said compound or composition to a subject in need thereof. The bacterial infection is preferably caused by a bacterium that expresses a Type II bacterial glutaminyl cyclase (bacQC). More preferably, the bacterial infection is caused by a bacterium selected from the group consisting of the genera *Porphyromonas, Prevotella* and *Tannerella*, preferably selected from the group consisting of the species *Porphyromonas gingivalis, Prevotella intermedia* and *Tannerella forsythia*.

The bacQC inhibitor compound or the pharmaceutical composition used in the methods according the present disclosure preferably selectively kill or selectively inhibit the growth of a bacterium selected from the group consisting of the genera *Porphyromonas, Prevotella* and *Tannerella*, preferably selected from the group consisting of the species *Porphyromonas gingivalis, Prevotella intermedia* and *Tannerella forsythia*, within a biofilm, whereas the remaining bacteria within the biofilm preferably remain essentially unaffected (i.e. are killed or their growth is inhibited to a significantly smaller extent). Said biofilm is preferably a complex biofilm, more preferably a naturally occurring biofilm, and even more preferably a naturally occurring oral biofilm.

The present disclosure further provides a bacQC inhibitor compound or a pharmaceutical composition for use in a method for therapy or prophylaxis of an acute, chronic or recurrent periodontal disease or condition. The major categories of periodontal diseases and conditions are classified in the groups of dental plaque-induced gingival diseases, chronic periodontitis, aggressive periodontitis, periodontitis as a manifestation of systemic diseases, necrotizing periodontal diseases, abscesses of the periodontium, periodontitis associated with endodontic lesions, peri-implant mucositis, peri-implantitis, and endodontic infections. In the present disclosure, the acute, chronic or recurrent periodontal disease is preferably selected from the group consisting of dental plaque-induced gingival diseases, chronic periodontitis, aggressive periodontitis, periodontitis as a manifestation of systemic diseases, necrotizing periodontal diseases, abscesses of the periodontium, periodontitis associated with endodontic lesions, peri-implant mucositis, peri-implantitis, and endodontic infections. The present disclosure also provides a method for therapy or prophylaxis of an acute, chronic or recurrent periodontal disease which is preferably selected from the group consisting of dental plaque-induced gingival diseases, chronic periodontitis, aggressive periodontitis, periodontitis as a manifestation of systemic diseases, necrotizing periodontal diseases, abscesses of the periodontium, periodontitis associated with endodontic lesions, peri-implant mucositis, peri-implantitis, and endodontic infections, wherein the method comprises administration of a therapeutically effective amount of a bacQC inhibitor compound or a pharmaceutical composition according to the present disclosure to a subject in need thereof. Further acute, chronic or recurrent periodontal diseases are described, e.g., in Armitage, A. *Ann Periodontol* 1999, 4, 1-6.

In one embodiment of the present disclosure, the compound or the pharmaceutical composition according to the present disclosure is preferably used in any of the methods described above, wherein the route of administration is topical administration, and/or wherein the method is a nonsurgical method. In another embodiment, the inhibitor compound or the pharmaceutical composition according to the present disclosure is preferably used in any of the methods described above, wherein the route of administration is systemic administration, and/or wherein the method is a nonsurgical method.

The term "subject" as used herein refers to an animal, preferably a mammal, most preferably a human, who is or has been the object of treatment, therapy, prophylaxis, observation or experiment.

The term "therapeutically effective amount" as used herein means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

Protein Crystals

The present disclosure provides crystals of bacterial glutaminyl cyclases (bacQCs).

The atomic coordinates in the crystal structure of PgQC are shown in Table 1 on pages 21-42 of the European patent application EP18158343 filed with the European Patent Office on 23 Feb. 2018, the priority of which is claimed by the present application, and to which hereby reference is made; or alternatively, in the RCSB Protein Database (www.rcsb.org) under the PDB identification code 6QQL, deposited on 19 Feb. 2019. In one embodiment, the crystal comprising a bacterial glutaminyl cyclase (bacQC) is a crystal comprising a PgQC, the PgQC being a polypeptide comprising the amino acid sequence of SEQ ID NO. 1 or an amino acid sequence having a sequence identity of 90% or more to SEQ ID NO. 1, and preferably having:

the atomic coordinates according to Table 1 of EP18158343 or 6QQL as mentioned above, or wherein the root mean square deviation from the backbone atoms of the polypeptide chain according to Table 1 of EP18158343 or 6QQL as mentioned above is 2 Å or less, and/or a binding pocket defined by residues Gln133; Asp149; Glu182; Asp183; Tyr187; Gly188; Asp189; Asp190; Trp193; Cys194; Asp218; Met219; Phe232; Gly263; Ala264; Leu265; Thr266; Asp267; Val270; Ile284; Tyr286; Asn290; Glu291; His292; Gly293; Phe294; Trp298; His299 of SEQ ID NO: 1, and/or the space group P $3_1$ 2 1 and unit cell dimensions of a=89.9 Å, b=89.9 Å, c=164.7 Å, α=90°, β=90 and γ=120°.

Further preferably, the PgQC crystal diffracts x-rays for determination of atomic coordinates of the crystal to a resolution of between 2.81 and 44.95 Å.

The atomic coordinates in the crystal structure of TfQC are shown in Table 2 on pages 43-91 of the European patent application EP18158343 filed with the European Patent Office on 23 Feb. 2018, the priority of which is claimed by the present application, and to which hereby reference is made; or alternatively, in the RCSB Protein Database (www.rcsb.org) under the PDB identification code 6QRO, deposited on 19 Feb. 2019.

In another embodiment, the crystal comprising a bacterial glutaminyl cyclase (bacQC) may be a crystal comprising a TfQC, the TfQC being a polypeptide comprising the amino acid sequence of SEQ ID NO. 2 or an amino acid sequence having a sequence identity of 90% or more to SEQ ID NO. 2, and preferably having:

the atomic coordinates according to Table 2 of EP18158343 or 6QQL as mentioned above, or wherein the root mean square deviation from the backbone atoms of the polypeptide chain according to Table 2 of EP18158343 or 6QQL as mentioned above is 3 Å or less, and/or a binding pocket defined by residues His126; Arg130; His135; Glu183; Asp184; Gly186; Thr187; Glu189; Lys195; Pro196; Asp197; Trp199; Asp224; Met225; Gly269; Ala270; Ile271; Val272; Gln276; Tyr277; Ile290; Tyr292; Gln297; Ser 298; Gly299; Phe300; Trp304; His305 of SEQ ID NO: 2, and/or the space group P 1 and unit cell dimensions of a=56.1 Å, b=79.2 Å, c=83.1 Å, α=89.9°, β=90.0° and γ=71.9°.

Further preferably, the TfQC crystal diffracts x-rays for determination of atomic coordinates of the crystal to a resolution of between 2.10 and 38.28 Å.

The root mean square deviation from the backbone atoms of the polypeptide chain can be determined as a positional root mean square deviation from the structural coordinates of the equivalent $C_\alpha$ backbone atoms following structural alignment of the structure to be compared with the structure of the protein according to the present invention and using the program DALI (L. Holm and C. Sander, *Science*, 1996, vol. 273, 595-602). The term "binding pocket" as used herein includes references to a specific region (or atom) in a molecular entity that is capable of entering into a stabilizing interaction with another molecular entity. In certain embodiments, the term also refers to the reactive parts of a macromolecule that directly participate in its specific combination with another molecule. In an alternative embodiment, a binding site comprises or is defined by the three-dimensional arrangement of one or more amino acid residues within a folded polypeptide. Most preferably, the binding pocket of the bacQCs described herein is defined, respectively, by the atoms of the residues listed for each of the bacQCs above.

In a particular embodiment of the invention, the crystal comprising a bacterial glutaminyl cyclase (bacQC) is a crystal comprising a polypeptide fragment comprising a truncated amino acid sequence of SEQ ID NO. 1 or an amino acid sequence having a sequence identity of 90% or more to a truncated amino acid sequence of SEQ ID NO. 1. Said truncated amino acid sequence of SEQ ID NO. 1 is obtained by deletion of 1 to 132, preferably 1 to 20, more preferably 2 to 10 consecutive amino acids starting from the N-terminus of the amino acid sequence of SEQ ID NO. 1, and/or by deletion of 1 to 34, preferably 1 to 10, more preferably 2 to 5 consecutive amino acids starting from the C-terminus of SEQ ID NO. 1.

In another particular embodiment of the invention, the crystal comprising a bacterial glutaminyl cyclase (bacQC) is a crystal comprising a polypeptide fragment comprising a truncated amino acid sequence of SEQ ID NO. 2 or an amino acid sequence having a sequence identity of 90% or more to a truncated amino acid sequence of SEQ ID NO. 2. Said truncated amino acid sequence of SEQ ID NO. 2 is obtained by deletion of 1 to 125, preferably 1 to 21, more preferably 2 to 10 consecutive amino acids starting from the N-terminus of the amino acid sequence of SEQ ID NO. 2, and/or by deletion of 1 to 29, preferably 1 to 10, more preferably 2 to 5 consecutive amino acids starting from the C-terminus of SEQ ID NO. 2.

In yet another embodiment, a co-crystal is provided comprising bacQC as described above together with a candidate compound. The candidate compound is preferably bound to a binding pocket of the bacQC. The candidate compound is further preferably a bacQC inhibitor. Most preferably, the candidate compound is a compound according to one of the Formulae I or II as specified in any one of aspects <1> to <19>.

The crystals and co-crystals according to the present invention are preferably of sufficient quality and size to allow for the determination of the three-dimensional X-ray diffraction structure of a bacterial glutaminyl cyclase to a resolution of about 1.9 Å and to about 2.8 Å.

Both crystal structures share an α-β hydrolase fold, that is determined by 8 stranded β-sheet surrounded by 7 α-helices. In both cases the Zn-ion is tetrahedrally coordinated with 2 aspartates and 1 histidine, respectively. The fourth coordination site is occupied by a water molecule, the substrate or a metal binding group as sub-structural part of an inhibitor. These metal interactions of a small group and the Zn ion are essential for the design of an active compound used as antibacterial agent against the pathogens mentioned herein. Furthermore, the binding sites are formed by hydrophobic and hydrophilic areas that are different compared to the human enzyme and that are responsible to generate the selectivity for the bacterial enzymes (see FIGS. 7-10).

The crystals and co-crystals according to the present invention can be prepared as by batch, liquid bridge, dialysis, vapor diffusion methods, such as hanging or sitting drop vapor diffusion, as further described below.

One preferred method for preparing the bacQC crystal as defined above comprises the steps of:

(a) providing a solution comprising a bacQC as defined above, preferably in the presence of 150 mM NaCl, in a suitable buffer such as 50 mM Tris-HCl pH 8.0;

(b) mixing said solution with an equal amount crystallization solution comprising (i) 1 M HEPES pH 8.0, 2 M ammonium sulfate, 3% (v/v) PEG400 in the case of PgQC; or (ii) 0.1 M sodium acetate pH 4.6, 2 M ammonium sulfate in the case of TfQC; and (c) incubating the obtained mixture under conditions to promote hanging or sitting drop vapor diffusion for a time sufficient to obtain the crystal of the bacQC.

One method for preparing the co-crystal of a bacQC together with a candidate compound comprises the steps:

(a) providing a solution comprising a bacQC as defined above, preferably PgQC, and a candidate compound dissolved in 100 mM HCl, in a molar ratio of bacQC:compound=1:2.3;

(b) mixing said solution with an equal amount crystallization solution comprising 1 M HEPES pH 8.0, 2 M ammonium sulfate, 3% (v/v) PEG400; and (c) incubating the obtained mixture under conditions to promote hanging or sitting drop vapor diffusion for a time sufficient to obtain the co-crystal of the bacQC and the candidate compound.

Another method for preparing the co-crystal of a bacQC together with a candidate compound comprises the steps:

(d) providing a solution as seed stock of harvested and crushed bacQC, preferably TfQC crystal without candidate compound produced as defined above;

(e) providing a solution comprising a bacQC as defined above, and a candidate compound dissolved in 100 mM HC, in a molar ratio of bacQC:compound=1:1.2;

(f) mixing said solution with an equal amount crystallization solution comprising 1 M Potassium PIPES pH 6.6 or pH 6.8, 32.5% (v/v) PEG 600, 0.1 M NaCl and 15% seed stock solution;

(g) incubating the obtained mixture under conditions to promote hanging or sitting drop vapor diffusion for a time sufficient to obtain the co-crystal of the bacQC and the candidate compound.

Methods for Identifying Candidate Compounds and/or Inhibitors The present invention provides a method for identifying a candidate compound which may associate with a binding pocket of a bacQC comprising the following steps:

(a) generating a 3-dimensional model of the respective bacQC using the structural coordinates described in Table 1 of EP18158343 or 6QQL as mentioned above or 2, (b) analyzing the binding pocket provided by residues Gln133; Asp149; Glu182; Asp183; Tyr187; Gly188; Asp189; Asp190: Trp193; Cys194; Asp218; Met219; Phe232; Gly263; Ala264; Leu265; Thr266; Asp267; Val270; Ile284; Tyr286; Asn290; Glu291; His292; Gly293; Phe294; Trp298; His299 of SEQ ID NO: 1 according to the coordinates of Table 1 of EP18158343 or 6QQL as mentioned above, or analyzing the binding pocket provided by residues His126; Arg130; His135; Glu183; Asp184; Gly186; Thr187; Glu189; Lys195; Pro196; Asp197; Trp199; Asp224; Met225; Gly269; Ala270; Ile271; Val272; Gln276; Tyr277; Ile290; Tyr292; Gln297; Ser298; Gly299; Phe300; Trp304; His305 of SEQ ID NO: 2 according to the coordinates of Table 2 of EP18158343 or 6QQL as mentioned above;

(c) performing computer modeling analysis to identify a candidate compound which may associate with a binding pocket of the respective bacQC.

Preferably, the method further comprises:
(d) verifying in vitro whether the candidate compound reduces the catalytic activity of the bacQC, thereby classifying a candidate compound that reduces the catalytic activity of the bacQC as a bacQC inhibitor.

Verifying whether a candidate compound reduces the catalytic activity of the bacQC can be performed, for example, by a method for identifying an inhibitor of the bacQC comprising the following steps (d1)-(d5):
(d1) providing a composition comprising a substrate of the bacQC and the bacQC;
(d2) providing a candidate compound identified in (c);
(d3) contacting the candidate compound with the composition;
(d4) monitoring the catalytic activity of the bacQC;
(d5) classifying the candidate compound as an inhibitor of the bacQC based on the effect of the candidate compound on the catalytic activity of bacQC, wherein a candidate compound that reduces the catalytic activity of the bacQC is classified a bacQC inhibitor.

Said composition (in step d1) can be an aqueous solution, preferably comprising suitable buffer and/or salt components. Said substrate is preferably a peptide or peptide derivative comprising a glutamine residue at its N-terminus. Said substrate is preferably labeled, more preferably isotopically labeled, most preferably a fluorogenic substrate. The fluorogenic substrate preferably undergoes a change in fluorescence intensity after being converted in the course of a reaction catalyzed by a bacQC.

A suitable fluorogenic substrate for monitoring bacQC activity is H-Gln-AMC, as described in Schilling, S., Hoffmann, T., Wermann, M., Heiser, U., Wasternack, C., and Demuth, H.-U. *Anal. Biochem.* 2002, 303, 49-56 (Schilling et al., 2002), as shown in the following scheme:

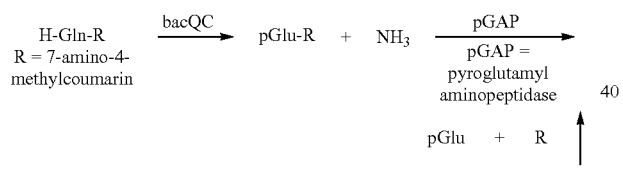

The candidate compound can be contacted prior to, simultaneously with or after the addition of the remaining components of the composition of step (d1). The candidate compound is preferably provided in solution, more preferably as a DMSO solution.

The conversion of the substrate is monitored over time, e.g., by monitoring the emission of the fluorophore generated by the cleavage of a fluorogenic substrate. bacQC activity can be determined from a standard curve of the AMC under assay conditions.

The bacQC catalytic activity can be determined using different concentration of substrate, bacQC and/or candidate compound. Suitable measures for the bacQC catalytic activity are, e.g., inhibitory constants ($K_i$), 50% residual activity (RA) in the presence of a given concentration of a candidate compound, and/or $IC_{50}$ values.

The present invention further provides a method for identifying a candidate compound which associates with a binding pocket of a bacQC, the method comprising the following steps:
(a) generating a 3-dimensional model of a co-crystal comprising bacQC as described above together with a candidate compound;
(b) analyzing the distances between the atoms of the candidate compound and the atoms of the binding pocket provided by residues Gln133; Asp149; Glu182; Asp183; Tyr187; Gly188; Asp189; Asp190; Trp193; Cys194; Asp218; Met219; Phe232; Gly263; Ala264; Leu265; Thr266; Asp267; Val270; Ile284; Tyr286; Asn290; Glu291; His292; Gly293; Phe294; Trp298; His299 of SEQ ID NO: 1, or the atoms of the binding pocket atoms of by residues XXXX His126; Arg130; His135; Glu183; Asp184; Gly186; Thr187; Glu189; Lys195; Pro196; Asp197; Trp199; Asp224; Met225; Gly269; Ala270; Ile271; Val272; Gln276; Tyr277; Ile290; Tyr292; Gln297; Ser 298; Gly299; Phe300; Trp304; His305 of SEQ ID NO: 2, to identify a candidate compound that associates with the binding pocket of the bacQC.

Preferably, the method further comprises:
(c) verifying in vitro whether the candidate compound reduces the catalytic activity of the bacQC, thereby classifying a candidate compound that reduces the catalytic activity of the bacQC as a bacQC inhibitor.

Verifying whether a candidate compound reduces the catalytic activity of the bacQC can be performed, for example, by a method for identifying an inhibitor of the bacQC comprising the following steps (c1)-(c5):
(c1) providing a composition comprising a substrate of the bacQC and the bacQC;
(c2) providing a candidate compound identified in (b);
(c3) contacting the candidate compound with the composition;
(c4) monitoring the catalytic activity of the bacQC;
(c5) classifying the candidate compound as an inhibitor of the bacQC based on the effect of the candidate compound on the catalytic activity of bacQC, wherein a candidate compound that reduces the catalytic activity of the bacQC is classified a bacQC inhibitor.

EXAMPLES

I. Identification and Preparation of Putative Bacterial Glutaminyl Cyclases (bacQC)

a) Identification

Bioinformatics analysis of the secretome of the oral pathogens *P. gingivalis, T. forsythia*, and *P. intermedia* (http://www.oralgen.lanl.gov/) showed that about 80% of the secreted proteins bearing a signal peptide are cleaved at a Xaa-Gln peptide bond by the signal peptidase. The N-termini of the released proteins contain a pGlu-residue. This implies the existence of glutaminyl cyclases which seem to be essential for growth protein translocation across outer membrane and the growth of periodontal pathogens.

FIG. 1 shows an amino acid sequence alignment of human QC (hQC, SEQ ID NO: 4) and putative bacterial QC from *P. gingivalis* (PgQC, SEQ ID NO: 1) (A), and an amino acid sequence alignment of further putative QC *P. intermedia* (PiQC, SEQ ID NO: 3) and *T. forsythia* (TfQC, SEQ ID NO: 2) and *P. gingivalis* (PgQC, SEQ ID NO: 1) (B). Putative PgQC possesses a 25% identity to human QC. Furthermore, putative TfQC exhibits a 49% identity to PgQC and QC from *P. intermedia* possess a 42% identity to PgQC. Grey underlined cysteine residues reflects disulfide bridges in hQC which is missing in PgQC. Bold sequences in human QC reflects highly conserved residues of Type II QC. Grey sequences described putative signal sequences of PgQC and hQC Furthermore the typical metal binding motif Asp-Glu- His is presented in bold and underlined letters. A putative metal binding motif was also identified in TfQC and PiQC (B, bold letters). The alignments were prepared using program Clustal Omega at EMBL-EBlnet; (*) indicates positions which have a single, fully conserved residue, (:) indicates conservation between groups of strongly similar properties, (.) indicates conservation between groups of weakly similar properties (http://www.ebi.ac.uk/Tools/msa/clustalo/).

BLAST analysis revealed an open reading frame (ORF) encoding putative QC protein in *P. gingivalis* (WP_005874301). The primary structure of this putative QC protein shows a 25% identity to human QC. Furthermore, putative QC proteins were also identified in the genome of the oral pathogens *P. intermedia* (WP_014709208) and *T. forsythia* (WP_014225037) which shares a 42% or 49% identity to putative QC from *P. gingivalis* (FIG. 1). As shown by the amino acid alignment, conserved residues of human QC seem to be different in bacterial QCs from those conserved cysteine residues which form disulfide bound in human and other Type II QCs are presumably not presence in all three putative bacterial QC. However, highly conserved metal binding motif Asp144, Glu184 (Asp) and His322 of Type II QC (Wintjens et al., 2006) seem to be present in bacterial putative QC which could represent the catalytic center. The primary structures of these proteins may provide an indication that these proteins are actual QCs.

b) Preparation

FIG. 2 shows SDS-PAGE of purified recombinant putative bacterial QCs expressed in *E. coli* Rosetta(DE3)pLysS and purified as described in detail below. Therefore, 30 μg purified protein were loaded to 12% SDS-PAGE and visualized by coomassie staining, lane 1, PageRuler Broad Range unstained (Thermofisher Scientific), lane 2, His-PgQC, lane 3, HisPiQC and lane 5, HisTfQC. All three putative bacterial QCs possess a theoretical molecular mass of =37 KDa.

aa) Host Strains and Media

*E. coli* strain DH5a or XL-1 blue (Stratagene) were used for cloning procedures. *E. coli* Rosetta(DE3)pLysS (Novagene) was used for protein expression. The alkaline phosphatase activity assay was performed in the CC118 pGP1-2 strain (Tabor, S. and Richardson, C. C. *Proc. Natl. Acad. Sci. U.S.A.* 1985, 82, 1074-1078; Manoil, C., J. J. Mekalanos and Beckwith, *J. J. Bacteriol.* 1990, 172(2), 515-518). All *E. coli* strains were grown in Luria-Bertani medium as indicated at 20° C., 30° C. or 37° C. Antibiotics (ampicillin [50 to 125 mg/liter], chloramphenicol [15 to 30 mg/liter], and kanamycin [25 mg/liter]) were added where appropriate. For preparation of solid media 1.5% agar (Roth) was added to corresponding broth.

bb) Molecular Cloning of Plasmid Vectors Encoding the Bacterial QCs

All cloning procedures were performed applying standard molecular biology techniques. For protein expression, open reading frames (ORFs) of PgQC (SEQ ID NO: 1, putative QC from *P. gingivalis*), PiQC (SEQ ID NO: 3 putative QC from *P. intermedia*) and TfQC (SEQ ID NO: 2, putative QC from *T. forsythia*) were amplified using synthesized DNA sequences purchased from Eurofins Genomics as templates in a PCR to introduce a NheI/NdeI restriction site essential for direct cloning into the vector pET28a(+) (Novagen). For the construction of a PgQC-'PhoA fusion protein, putative pgQC with predicted signal sequence was subcloned into pET26b(+) via NheI/XhoI restriction site using primer pair $_{seq}$pgQC NdeI (forward) and $_{seq}$pgQCXhoI reverse. Furthermore, pgQC with native signal sequence including a ribosome binding site of a pET26b(+) vector was amplified using primer pair $_{seq}$pgQC RBS NotI (forward) and $_{seq}$pgQC XbaI (reverse) to clone into the phoA expression vector pECD637. All Primers for cloning were purchased from Metabion and described in Table 1.

TABLE 1

Oligonucleotides used for cloning of bacQC constructs

| SEQ ID NO: | Primer | Sequence (5' → 3') |
|---|---|---|
| 5 | pgQC NdeI (forward) | AAA CAT ATG AAC GGC AAT AAC ACA AGT GAA |
| 6 | pgQC NheI (reverse) | TTT GCT AGC TCA GTG TGA AGC GGC TTT |
| 7 | piQC NdeI (forward) | TTT CAT ATG AAA GGA AAA TCG TCT AAC |
| 8 | piQC NheI (reverse) | ATG CTA GCT TAC ATG CTG TAA AGC AC |
| 9 | tfQC NdeI (forward) | TCA CAT ATG GGT CAG AAA AAT ACG ACA |
| 10 | tfQC NheI (reverse) | ATG CTA GCT TAT TTC TCA TTA TAA ATC AC |
| 11 | $_{seq}$pgQC NdeI (forward) | AAA CAT ATG AAA AGA CTG ATA ACA ACA GGA GCA GCC TTT CTA CTG GCT GCT ACA CTC TCT GCC TGC AAC GGC AAT AAC ACA AGT GAA ACG |
| 12 | $_{seq}$pgQC XhoI (reverse) | TTT CTC GAG GTG TGA AGC GGC TTT CAC |
| 13 | $_{seq}$pgQC RBS NotI (forward) | TGG CGG CCG CTA AGA AGG AGA |
| 14 | $_{seq}$pgQC XbaI (reverse) | TTT TCT AGA GTG TGA AGC GGC TTT CAC | cc) Expression of Bacterial QC as His Tag Fusion Protein or as 'PhoA Fusion Protein The expression vector pET28a(+)::pgQC was transformed in *E. coli* Rosetta(DE3)pLysS. Bacteria were grown in Luria-Bertani medium containing kanamycin (25 μg/ml) and chloramphenicol (15 μg/ml) at 37° C. until the cell density reached an OD 600~0.6. The cultures were induced with 0.4 mM isopropyl β-D-1-thiogalactopyranoside and a 2% (v/v) ethanol volume was added followed by an incubation time for 16 h at 20° C. Cultures were harvested by centrifugation at 4° C. and 3900 g for 30 min and cell pellets were storage at −20°.

For expression of $_{seq}$PgQC-'PhoA fusion protein, recombinant vector pECD$^{637}$::$_{seq}$pgQC was transformed into CC118 (lacking e.g. phoA gene) along with helper plasmid pGP1-2. Cultures were inoculated at 30° C. overnight. Furthermore overnight cultures were diluted into fresh Luria-Bertani media to a final optical density (OD600) ~0.4 followed by an incubation at 42° C. for 20 min to induce expression of $_{seq}$PgQC-'PhoA fusion proteins. Then cultures were inoculated for further 2 h at 30° C. Finally optical density OD600 was determined using spectrophotometer (BioRad) and 200 µl of cultures were harvested by centrifugation at 4° C. and 16000 g for 15 min for determination of PhoA activity.

dd) Purification of Bacterial QCs

Cell pellet of 500 ml culture were resuspended in 20 ml buffer consists of 50 mM Tris-HCl, 150 mM NaCl pH 8.0, 10 µg/ml DNase and protease inhibitor cocktail mix (complete mini tablets, EDTA-free, Roche). Cells were disrupted by passing through French Press (Thermo Scientific, Waltman, MA, USA) for 3-4 times. Cell debris was removed by centrifugation at 4° C. and 30000 g for 30 min. Supernatant was 1:2 diluted with equilibration buffer and loaded on 5 ml HisTrap column (GE Healthcare). The column was equilibrated with 50 mM Tris-HCl containing 150 mM NaCl pH 8.0. After washing with several column volumes of equilibration buffer and at least with 20 mM imidazole protein were eluted using multiple step gradients, reaching a final concentration of 250 mM imidazole, whereas majority of pure protein was already eluted with approximately 100 mM imidazole. All bacQC containing fractions were pooled, concentrated with Vivaspin 20 (Sartorius AG) and applied to a HiPrep 26/10 desalting column (GE, Healthcare), which was equilibrated with 50 mM Tris-HCl, 150 mM NaCl pH 8.0. The purification was analyzed by SDS-PAGE and the protein content was determined by absorption at 280 nm using NanoDrop 2000 spectrophotometer (Thermo Scientific) or according to the methods of Bradford or Gill and von Hippel (Bradford, M. M. 1976 Anal Biochem 72, 248-254; Gill, S. C. and von Hippel, P. H. 1989 Anal Biochem 182, 319-326). Finally purified recombinant fusion bacQC proteins were shock-frozen in liquid nitrogen and stored at −80° C. or glycerol was added to a final concentration of 50% and storage at −20° C. His Tag of N-terminal fusion proteins were removed using 1 Unit Thrombin per 1 mg fusion protein (Thrombin cleavage Capture Kit, Novagen) in presence of 20 mM Tris-HCl, 150 mM NaCl, 2.5 mM CaCl$_2$) at pH 8.0 followed by an incubation for 16 h at 4° C. Thrombin was removed through binding to Steptavidin Agarose (Thrombin cleavage Capture Kit, Novagen) and bacQC proteins without HisTag were recovered by spin-filtration. After further desalting step using HiPrep (26/10) bacQC fractions were pooled and concentrated with Vivaspin 20 (Sartorius AG). Finally recombinant bacQC in 50 mM Tris-HCl, 150 mM NaCl pH 8.0 was shock-frozen in liquid nitrogen and storage at −80° C. or glycerol was added to a final concentration of 50% and storage at −20° C. PiQC was expressed and purified in the same way like PgQC. TfQC was expressed in the same way like PgQC and purified using HiTrap Talon column (GE, Healthcare).

Conclusions

All putative bacterial QC were expressed in *E. coli* Rosetta(DE3)pLysS without signal sequence as N-terminal His Tag fusion proteins and purified to homogeneity via affinity chromatography. 16-40 mg recombinant pure His-Tag fusion proteins were isolated from approximately 500 ml of induced *E. coli* cultures.

Subsequently, His-tag of fusion proteins was cleaved by thrombin followed by enzymatic characterization of these putative bacterial QCs.

II. Protein Crystallization a) PgQC Crystallization

Crystals of crystallographic quality were obtained from PgQC expressed and purified as described above. PgQC was crystallized at a concentration of 90 µM (2.3 mg/ml) within 40 days at 15° C. using hanging drop vapor diffusion technique. In a drop, 1 µL protein solution was mixed with an equal volume of crystallization buffer consisting of 0.1 M HEPES pH 8.0, 3% (v/v) PEG 400 and 2 M (NH$_4$)$_2$SO$_4$. For the crystallization process, the protein-containing drop was placed in vapor equilibration with 500 µL crystallization buffer included in a reservoir.

Prior to X-ray measurement, crystals were cryoprotected by rapid soaking in crystallization buffer containing 18% (v/v) glycerol and subsequently flash frozen at −180° C. Data from a diffracting single crystal were collected in-house using a CCD detector (SATURN 944+, Rigaku Europe) mounted on a copper rotating-anode source (RA Micro 007, Rigaku Europe). Afterwards collected diffraction data were processed, scaled and merged using XDSGUI. The measured PgQC crystals belong to the trigonal space group P 31 2 1 with the cell constants a=89.9 Å, b=89.9 Å, c=164.7 Å, and α=90°, β=90°, γ=120°. They contain two molecules of PgQC in the asymmetric unit and diffract to 2.8 Å.

The initial phases for the PgQC structure were obtained by molecular replacement using the program PHASER MR from the CCP4 crystallographic suite and the search model PgQC with PQ 50, in which some cycles of manual rebuilding using the program COOT and maximum-likelihood refinement using REFMAC5 were carried out. The model was refined to an Rwork value of 0.2428 and an Rfree value of 0.30404. To obtain a final PgQC model, repeating cycles of manual rebuilding and refinement are sufficient.

b) TfQC Crystallization

Crystals of crystallographic quality were obtained from TfQC expressed and purified as described above. The Protein could be crystallized at a concentration of 9.91 mg/mL (279 µM) within 91 days at 15° C. using sitting drop vapor diffusion technique. Therefore, 200 nL protein was mixed with an equal volume of crystallization buffer consisting of 2 M (NH$_4$)$_2$SO$_4$ and 0.1 M Sodium acetate pH 4.6, in a drop staying in contact by vapor diffusion with a reservoir containing 55 µL of crystallization buffer.

Prior to X-ray measurement, crystals were cryoprotected by rapid soaking in crystallization buffer containing 25% (v/v) ethylene glycol and subsequently flash frozen at −180° C. The following data from a diffracting single crystal were collected in-house using a CCD detector (SATURN 944+, Rigaku Europe) mounted on a copper rotating-anode source (RA Micro 007, Rigaku Europe).

The obtained diffraction data were processed, scaled and merged using the program XDSGUI. TfQC crystals belong to the triclinic space group P1 with the cell constants a=56.1 Å, b=79.2 Å, c=83.1 Å, and α=89.9, β=90°, γ=71.90. They contain four molecules of TfQC in the asymmetric unit and diffract to 2.1 Å.

The initial phases of the estimated TfQC structure were obtained by molecular replacement using PHASER MR from the CCP4 crystallographic suite. To these solution strategy a suitable search model must be generated, because at these time point no model of TfQC existed. This model was prepared from an initial one of PgQC with PQ 50 by side chain pruning using the Program SCULPTOR from the PHENIX suite. The final TfQC model was obtained after repeating cycles of manual rebuilding using the program COOT and maximum-likelihood refinement using PHENIX.REFINE. It was refined to an Rwork value of 0.1938 and an $R_{free}$ value of 0.2404.

III. Fluorometric Assay for Glutaminyl Cyclase Activity

QC activity was evaluated using H-Gln-AMC as the substrate (as previously described in Schilling et al., 2002).

The assay consists of varying concentration of the fluorogenic substrate and 0.5 U pyroglutaminyl aminopeptidase in 50 mM Tris-HCl, 50 mM NaCl at pH 8.0. After 10 minute incubation time at 30° C. reaction was initiated by addition of bacQC to a final volume of 125 µl reaction mixture. The excitation/emission wavelength was 380/460 nm. bacQC activity was determined from a standard curve of the fluorophore AMC under assay conditions. All determinations were carried out in 96 well microtiter plates (Fisher Scientific) at 30° C. using the FluoStar Optima (BMG Labtech). The kinetic data were evaluated using GraFit software (Version 7, Erithacus software Ltd., Horley, UK).

Figure 3:
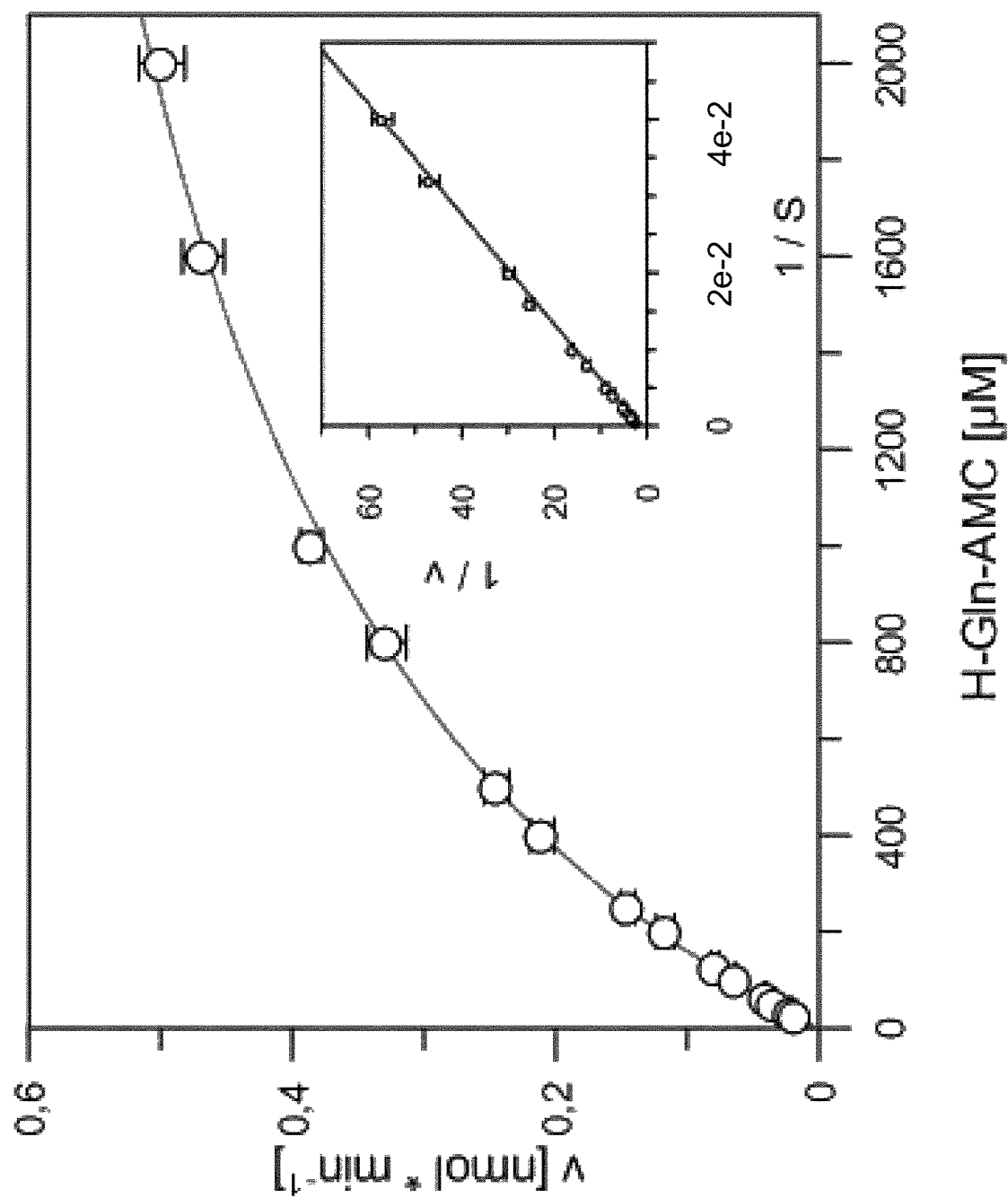

FIG. 3 shows Lineweaver-Burk plots for PgQC (A), PiQC (B) and TfQC (C) catalyzed cyclization of H-Gln-AMC. The inset shows a secondary plot of the obtained slopes of the Lineweaver-Burk evaluation. bacQC activity measurement carried out in 50 mM Tris-HCl, pH 8.0 and 50 mM Tris-HCl at 30° C. The kinetic data were evaluated using GraFit software (Version 7, Erithacus software Ltd., Horley, UK). Enzymatic parameters of bacterial QC were determined (Table 2), which differ from those of hQC (Schilling, S., Manhart, S., Hoffmann, T., Ludwig, H.-H., Wasternack, C., and Demuth, H.-U. *Biol. Chem.* 2003, 384, 1583-1592).

TABLE 2

Kinetic parameters for the conversion of H-Gln-AMC by bacterial QC. Determination of kinetic parameters was carried out in 50 mM Tris-HCl pH 8 and 50 mM NaCl at 30° C.

| Enzyme | $K_m$ [µM] | $k_{cat}$ [s$^{-1}$] | $k_{cat}/K_m$ [mM$^{-1}$ s$^{-1}$] |
|---|---|---|---|
| PgQC | 510.94 ± 13.3 | 4.71 ± 0.22 | 9.24 ± 0.28 |
| PiQC | 645.33 ± 7.4 | 8.51 ± 0.37 | 13.18 ± 0.05 |
| TfQC | 1091.67 ± 34.36 | 4.49 ± 0.22 | 4.1 ± 0.14 |

Conclusions

Purified recombinant proteins were tested for enzymatic activity using fluorometric assay with H-Gln-AMC as substrate. H-Gln-AMC as substrate was turned over by these bacterial proteins resulted in an increase of RFU and therefore an increasing reaction rate (FIG. 3). The affinity for H-Gln AMC as substrate is, in the case of PgQC and PiQC, approximately tenfold lower than that of hQC for this substrate. The $K_m$ value of TfQC is actually 20-fold higher than the $K_m$ value of hQC. Furthermore, the efficiency of bacterial proteins seems to be similar to that of hQC whereat PiQC possesses a twofold higher turnover number comparing PgQC or TfQC.

IV. Inhibitor Assay for Bacterial Glutaminyl Cyclase Activity

For inhibitor testing, the sample composition was the same as described above, except for the addition of the putative inhibitory compound. This resulted in presence of 1% or 2% (v/v) DMSO in reaction mixture. Inhibitory constants were determined using different concentration of H-Gln-AMC varying from ¼ $K_m$-2 $K_m$. Final concentration of bacterial QC was in a range between 25 nM-50 nM. The inhibitory constant was evaluated by fitting the set of progress curves to the general equation for competitive inhibition using GraFit software (Version 7, Erithacus software Ltd., Horley, UK).

Figure 4:
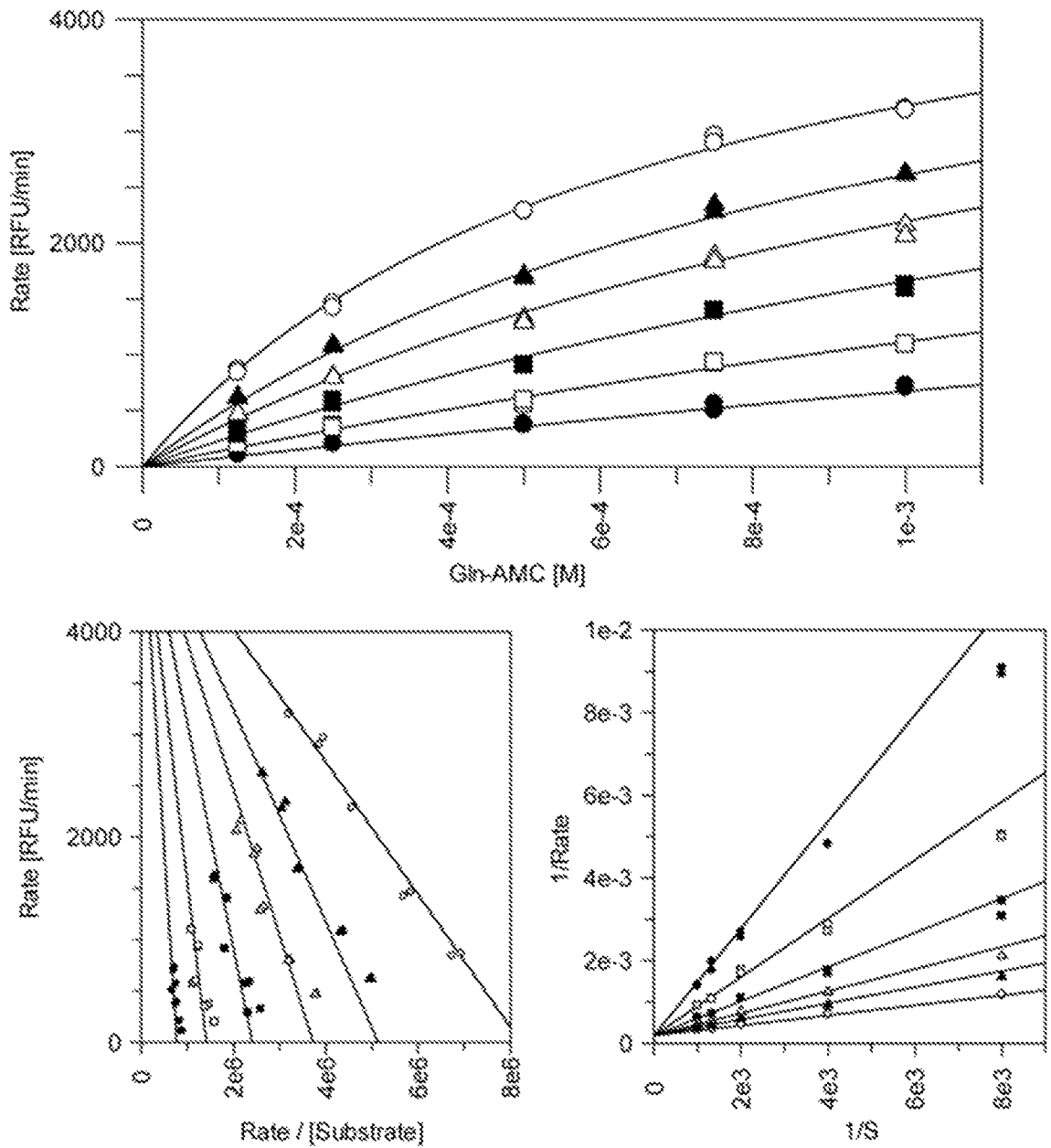
FIG. 4 shows exemplary v/S characteristics, Lineweaver-Burk and Eadie-Hofstee plots for PgQC-catalyzed cyclization of H-Gln-AMC in the presence of reference compound MWT-S-00431.

FIG. 4 shows exemplary v/S characteristics, Lineweaver-Burk and Eadie-Hofstee plots for PgQC catalyzed cyclization of H-Gln-AMC (A) in presence of (●) 1 µM, (□) 0.5 µM, (■) 0.25 µM, (Δ) 0.125 µM and (▲) 0.063 µM of reference compound MWT-S-00431 ((3,5-dichlorophenyl-1,4,6,7-tetrahydro-5H-imidazo[4,5-c]pyridin-5-yl)methanone). (○) represents reaction without inhibitor. Determinations were carried out in 50 mM Tris-HCl, 50 mM NaCl pH 8.0 and 1% (v/v) DMSO at 30° C. The kinetic parameters shown in Table 3 were obtained.

TABLE 3

Kinetic parameters for the inhibition of the conversion of H-Gln-AMC by PgQC in the presence of reference compound MWT-S-00431.

| Parameter | Value | Std. Error |
|---|---|---|
| $V_{max}$ [µM min$^{-1}$] | 4.41161 | $1.0569 \cdot 10^{-1}$ |
| $K_m$ [M] | $6.45485 \cdot 10^{-4}$ | $3.14087 \cdot 10^{-5}$ |
| $K_i$ [M] | $1.03698 \cdot 10^{-7}$ | $3.31239 \cdot 10^{-9}$ |

V. Inhibition of Glutaminyl Cyclases by the Compounds

The following compounds were synthesized as described in the Description of synthetic methods below. Average $K_i$ values for the inhibition of PgQC (isolated and purified as described above), TfQC, PiQC and hQC were measured using the above inhibitor assay and are shown in. $K_i$ refers to the average $K_i$ values measured as described above, and Std($K_i$) refers to the standard deviation of $K_i$.

TABLE 4

Inhibition of PgQC, TfQC, PiQC and hQC by bacQC inhibitors

| Compound Structure | Example No. | PgQC $K_i$ [nM] | TfQC $K_i$ [nM] | PiQC $K_i$ [nM] | hQC $K_i$ [nM] |
|---|---|---|---|---|---|
| 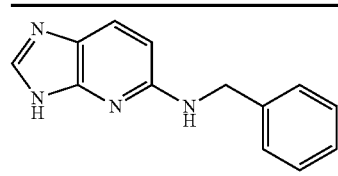 | 1 | 1945 ± 318 | 8255 ± 361 | 9400 ± 325 | 8800 ± 127 |

TABLE 4-continued
Inhibition of PgQC, TfQC, PiQC and hQC by bacQC inhibitors
| Compound Structure | Example No. | PgQC $K_i$ [nM] | TfQC $K_i$ [nM] | PiQC $K_i$ [nM] | hQC $K_i$ [nM] |
|---|---|---|---|---|---|
| 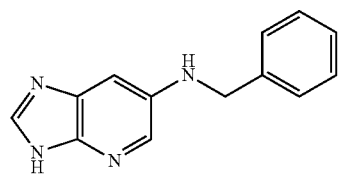 [SMILES: c1ccc(CNc2cnc3[nH]cnc3c2)cc1] | 2 | 149 ± 4 | 1400 ± 156 | 1945 ± 148 | 1280 ± 71 |
| 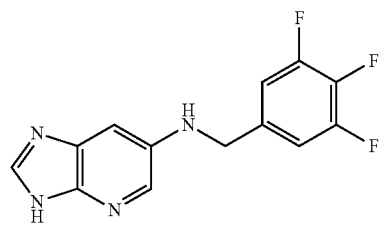 [SMILES: Fc1cc(CNc2cnc3[nH]cnc3c2)cc(F)c1F] | 3 | 157 ± 6 | n.d. | n.d. | n.d. |
| 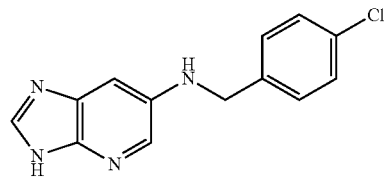 [SMILES: Clc1ccc(CNc2cnc3[nH]cnc3c2)cc1] | 4 | 53 ± 1 | n.d. | n.d. | 655 ± 27 |
| 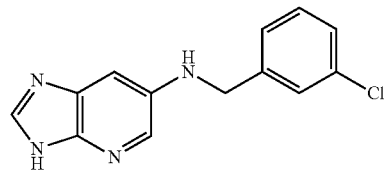 [SMILES: Clc1cccc(CNc2cnc3[nH]cnc3c2)c1] | 5 | 106 ± 13 | n.d. | n.d. | 769 ± 153 |
| 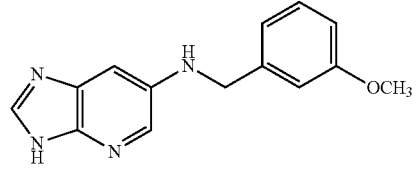 [SMILES: COc1cccc(CNc2cnc3[nH]cnc3c2)c1] | 6 | 77 ± 2 | n.d. | n.d. | 599 ± 40 |
| 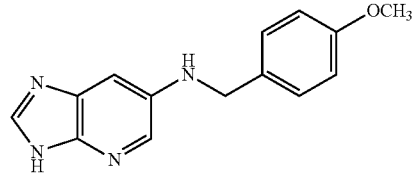 [SMILES: COc1ccc(CNc2cnc3[nH]cnc3c2)cc1] | 7 | 83 ± 3 | n.d. | n.d. | n.d. |
| 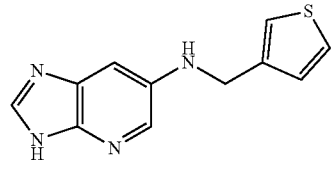 [SMILES: c1nc2cc(NCc3ccsc3)cnc2[nH]1] | 8 | 185 ± 11 | n.d. | n.d. | 1870 ± 78 |
| 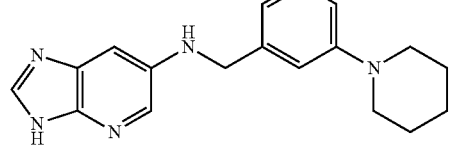 | 9 | 442 ± 71 | n.d. | n.d. | n.d. |

TABLE 4-continued
Inhibition of PgQC, TfQC, PiQC and hQC by bacQC inhibitors
| Compound Structure | Example No. | PgQC $K_i$ [nM] | TfQC $K_i$ [nM] | PiQC $K_i$ [nM] | hQC $K_i$ [nM] |
| --- | --- | --- | --- | --- | --- |
| 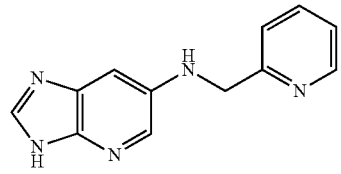 [SMILES: c1ccc(CNc2cnc3[nH]cnc3c2)nc1] | 10 | 395 ± 5 | n.d. | n.d. | n.d. |
| 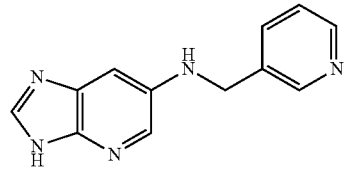 [SMILES: c1cncc(CNc2cnc3[nH]cnc3c2)c1] | 11 | 139 ± 4 | n.d. | n.d. | n.d. |
| 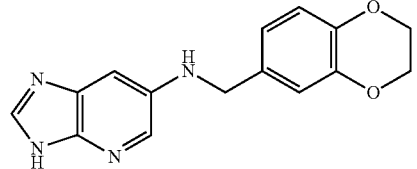 [SMILES: c1nc2cc(NCc3ccc4c(c3)OCCO4)cnc2[nH]1] | 12 | 44 ± 1 | 680 ± 45 | 728 ± 35 | 543 ± 20 |
| 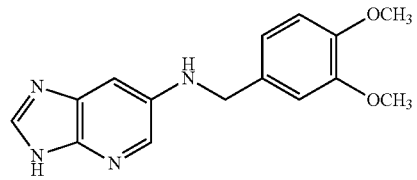 [SMILES: COc1ccc(CNc2cnc3[nH]cnc3c2)cc1OC] | 13 | 133 ± 6 | n.d. | n.d. | 556 ± 28 |
| 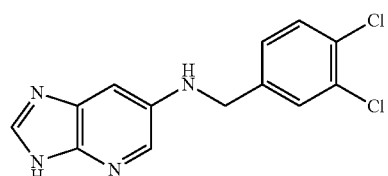 | 14 | 53 ± 2 | 358 ± 64 | 542 ± 44 | 431 ± 19 |
| 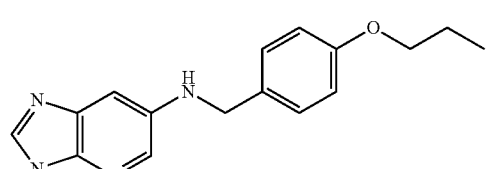 | 15 | 34 ± 2 | n.d. | n.d. | n.d. |
| 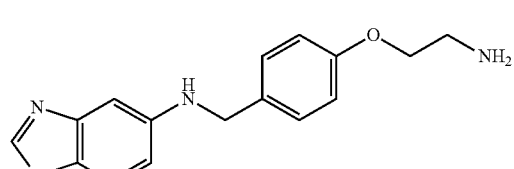 | 16 | 30 ± 2 | 317 ± 52 | 815 ± 4 | 1067 ± 230 |

TABLE 4-continued

Inhibition of PgQC, TfQC, PiQC and hQC by bacQC inhibitors

| Compound Structure | Example No. | PgQC $K_i$ [nM] | TfQC $K_i$ [nM] | PiQC $K_i$ [nM] | hQC $K_i$ [nM] |
|---|---|---|---|---|---|
| 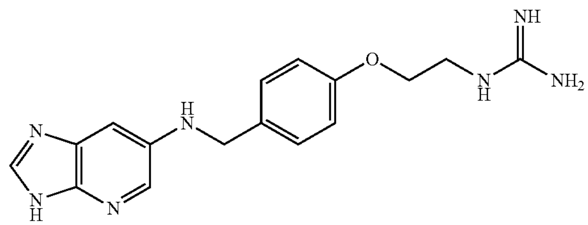 [SMILES: N=C(N)NCCOc1ccc(CNc2cnc3[nH]cnc3c2)cc1] | 17 | 14 ± 0.1 | 123 ± 16 | 349 ± 17 | 455 ± 14 |
| 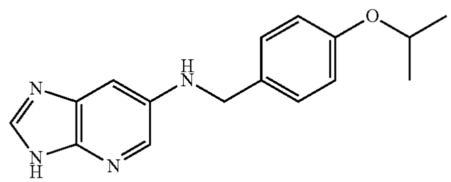 [SMILES: CC(C)Oc1ccc(CNc2cnc3[nH]cnc3c2)cc1] | 18 | 86 ± 5 | n.d. | n.d. | n.d. |
| 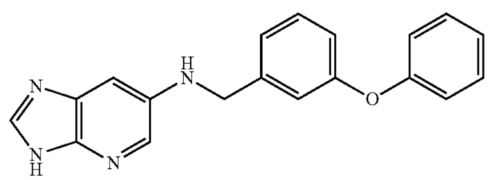 [SMILES: c1ccc(Oc2cccc(CNc3cnc4[nH]cnc4c3)c2)cc1] | 19 | 15 ± 0.1 | n.d. | n.d. | n.d. |
| 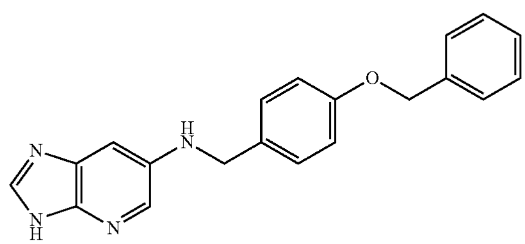 [SMILES: c1ccc(COc2ccc(CNc3cnc4[nH]cnc4c3)cc2)cc1] | 20 | 42 ± 4 | n.d. | n.d. | n.d. |
| 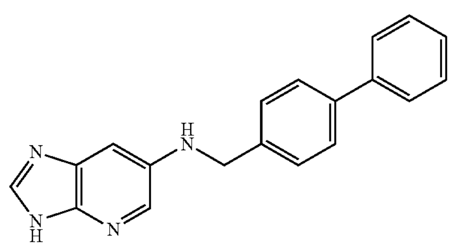 [SMILES: c1ccc(-c2ccc(CNc3cnc4[nH]cnc4c3)cc2)cc1] | 21 | 19 ± 1 | n.d. | n.d. | n.d. |
| 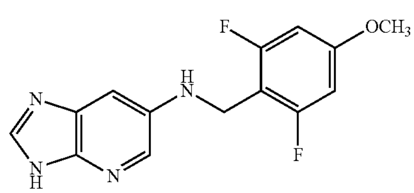 [SMILES: COc1cc(F)c(CNc2cnc3[nH]cnc3c2)c(F)c1] | 22 | 30 ± 1 | n.d. | n.d. | n.d. |
| 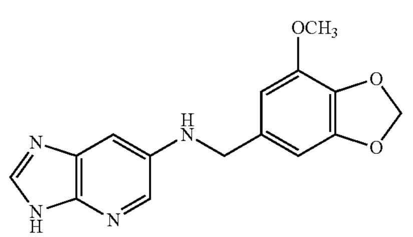 [SMILES: COc1cc(CNc2cnc3[nH]cnc3c2)cc2c1OCO2] | 23 | 65 ± 13 | n.d. | n.d. | n.d. |

TABLE 4-continued

Inhibition of PgQC, TfQC, PiQC and hQC by bacQC inhibitors

| Compound Structure | Example No. | PgQC $K_i$ [nM] | TfQC $K_i$ [nM] | PiQC $K_i$ [nM] | hQC $K_i$ [nM] |
|---|---|---|---|---|---|
| (imidazo[4,5-b]pyridine-NH-CH2-benzodioxole-CF2) | 24 | 67 ± 1 | n.d. | n.d. | n.d. |
| (imidazo[4,5-b]pyridine-NH-CH2-phenyl-pyridyl) | 25 | 38 ± 3 | n.d. | n.d. | n.d. |
| (imidazo[4,5-b]pyridine-NH-CH2-phenyl-O-CH2CH2-morpholine) | 26 | 33 ± 1 | n.d. | n.d. | n.d. |
| (imidazo[4,5-b]pyridine-NH-CH2-phenyl-morpholine) | 27 | 60 ± 2 | n.d. | n.d. | n.d. |

Conclusion

All of the compound according to the present invention exhibit inhibitory activity against bacterial glutaminyl cyclases. The above results show that the compounds and/or pharmaceutical compositions are useful in the treatment of periodontal and related diseases. In particular, the compounds and or pharmaceutical compositions are capable of selectively targeting pathogens which induce a periodontal disease (*P. gingivalis, T. forsythia* and *P. intermedia*) while at the same time being essentially inert with respect to the homologous to the human enzyme.

Furthermore, it was found that when the rest of the naturally occurring biofilm should be substantially preserved. Even more preferably, the compounds and/or pharmaceutical compositions should exhibit high in vivo activities against the targeted pathogens.

Furthermore, it was found that when the said pathogens are embedded within a biofilm (e.g., a complex biofilm, a naturally occurring biofilm or a naturally occurring oral biofilm), the remaining bacteria within the biofilm preferably remain essentially unaffected the compounds according to the present invention (i.e. are killed or their growth is inhibited to a significantly smaller extent).

As can be seen from the experimental data above, a particularly high inhibitory activity can be achieved when the imidazo[4,5-b]pyridine core is substituted at the 6-position (i.e. according to Formula I, like in Example 2), in contrast to substitution at the 5-position (i.e. according to Formula II, like in Example 1). Nevertheless, in both cases significant bacQC inhibitory activity and selectivity for PgQC over hQC human enzyme is observed (Table 5).

TABLE 5

Comparison of inhibition parameters of the compounds from Examples 1 and 2

| Target Protein | $K_i$ [µM] | | relative inhibitory activity |
|---|---|---|---|
| | Example 1 | Example 2 | [$K_i$(Example 1)]/[$K_i$(Example 2)] |
| PgQC | 1.95 | 0.15 | 13 |
| PiQC | 9.4 | 1.95 | 4.8 |
| TfQC | 8.3 | 1.4 | 5.9 |
| hQC | 8.8 | 1.28 | 6.9 |

Finally, in view of the relatively high degree of homology between PiQC and the other two bacQCs (as shown in FIG. 1), it that the compounds identified as inhibitors of PgQC and/or TfQC by using the methods of the present invention can also be expected to exhibit a significant PiQC activity (as evidenced by the experimental data in Table 6 above).

VI. Determination of $_{seq}$QC-'PhoA Activity

Figure 5:
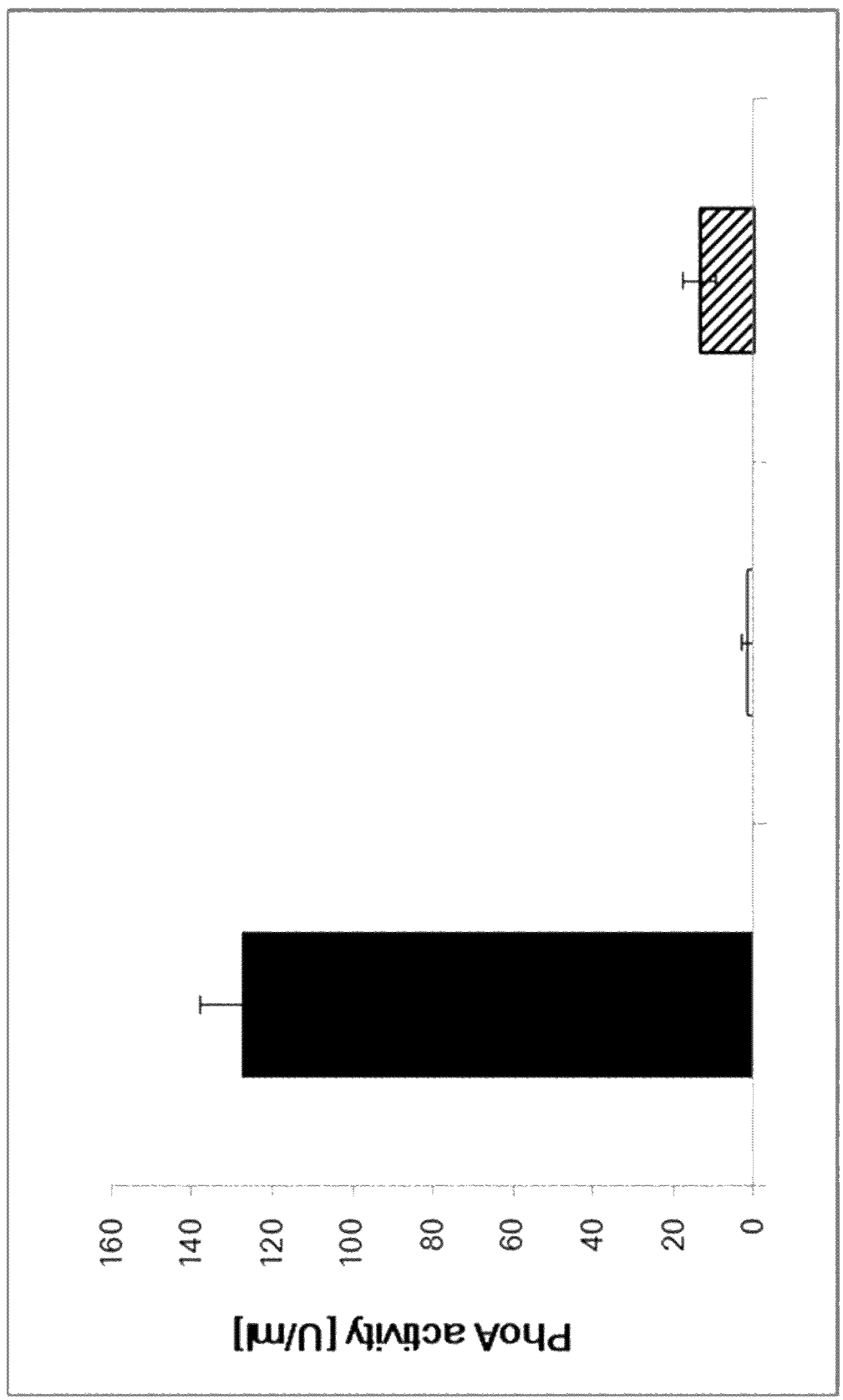
FIG. 5 shows PhoA activity in permeabilized *E. coli* CC118 pGP1-2 cells expressing seqPgQC-'PhoA fusion proteins.
Figure 7:
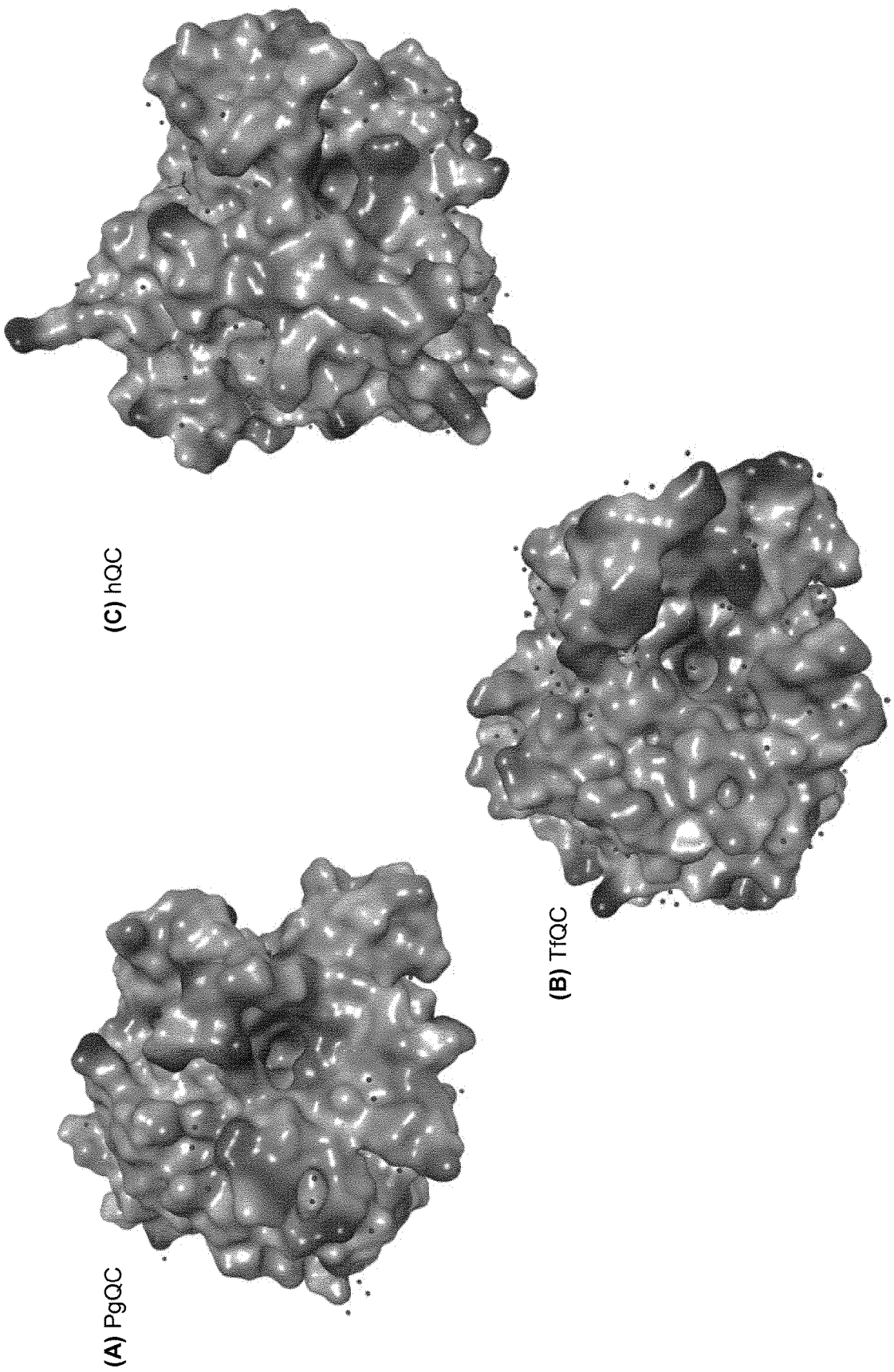
FIG. 7 shows molecular surfaces for three glutaminyl cyclases in the crystal: PgQC (A); TfQC (B); and hQC (PDB code 3SI0) (C). Surface is colored by lipophilicity (green: more lipophilic, purple: more hydrophilic); the centered hole shows the active site.
Figure 10:
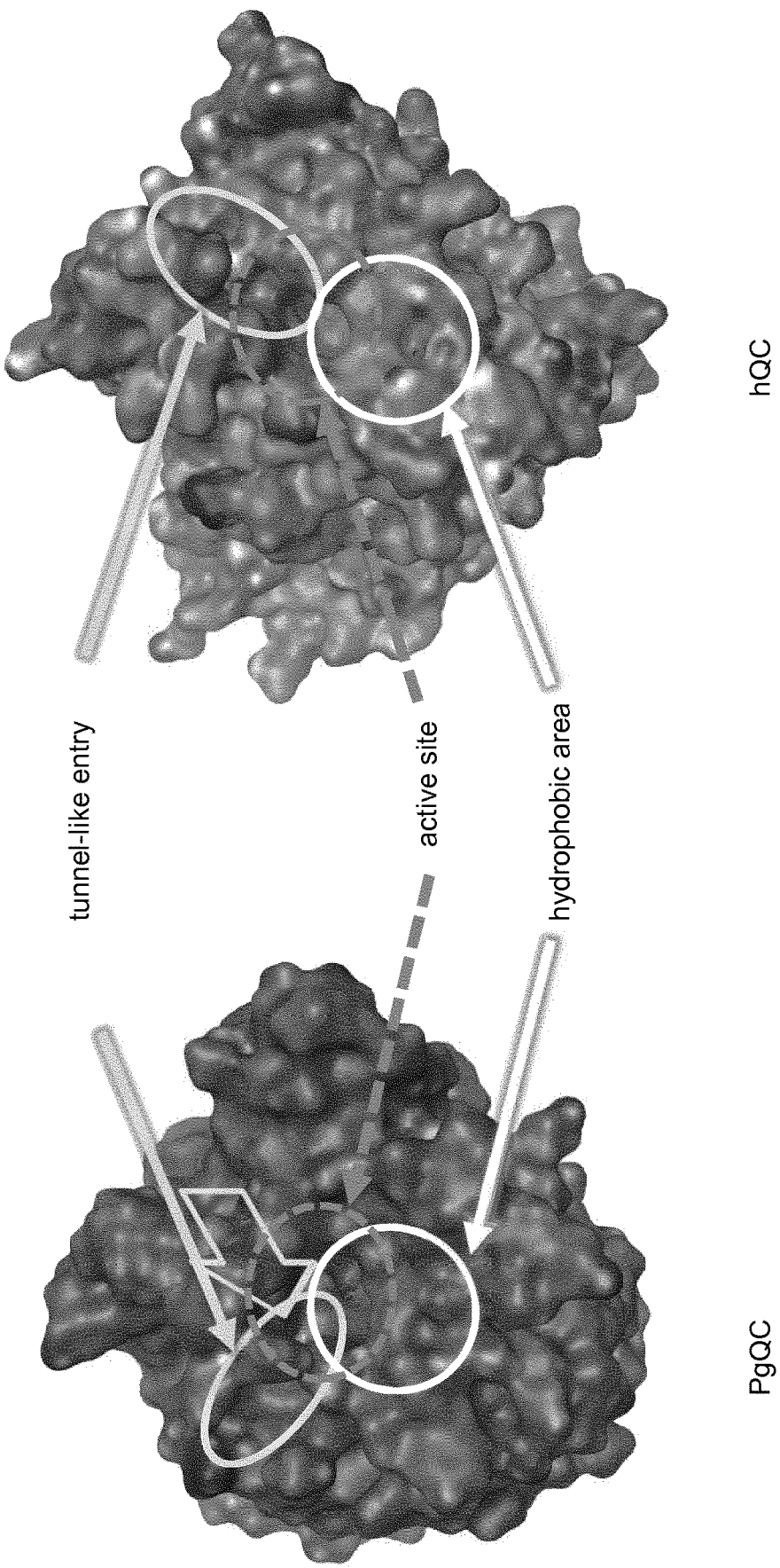
FIG. 10 shows a comparison of the active sites and molecular surfaces of PgQC and hQC.

FIG. 5. shows the PhoA activity in permeabilized *E. coli* CC118 pGP1-2 cells expressing $_{seq}$PgQC-'PhoA fusion proteins. PgQC with native putative signal sequence was cloned in pECD637 create a $_{seq}$PgQC-'PhoA fusion protein. Resulted vector was transformed into *E. coli* strain CC118 pGP1-2. The expression of fusion protein was initiated by incubation of the culture at 42° C. for 20 min. The PhoA activity of the induced culture was determined as described previously (Pribyl, T., *Topologie des CzcCBA-Efflux-Komplexes aus Ralstonia metallidurans CH*34. Dissertation, 2001, Martin-Luther-University Halle-Wittenberg). Black bar represent PhoA activity of *E. coli* cells expressing $_{seq}$PgQC-'PhoA, striped bar displays PhoA activity of cells expressing 'BlaM-'PhoA and served as positive control and cells expressed vector without insert were used as negative control (blank bar).

PhoA activity was determined from cultures grown as described above using chromogenic substrate p-nitrophenylphosphate (PNPP) (Pribyl, 2001). Therefore 200 μl cell suspension with known OD600 was harvested at 13000 rpm at 4° C. for 10 min. Cell pellet was washed in 0.5 ml 10 mM Tris-HCl pH 8.0, 10 mM MgSO$_4$ und 1 mM iodoacetamide. Resulted cell pellet was resuspended in 1 ml 1 M Tris-HCl pH 8.0, 0.1 mM ZnCl$_2$ und 1 mM iodoacetamide. Then 50 μl 0.1% (w/v) SDS and 50 μl Chloroform was added to the mixture followed by an incubation time for 5 min at 37° C. The reaction was then initiated by addition of 100 μl substrate solution (1 M Tris-HCl pH 8.0, 0.4% (w/v) PNPP). The reaction mixture was furthermore incubated at 37° C. until the solution turns yellow. The reaction was then stopped by addition of 120 μl 1 M KH$_2$PO$_4$, 0.5 M EDTA pH 8.0. The time taken to develop a yellow coloration defined specific enzymatic PhoA activity. Cell debris was removed by centrifugation (13000 rpm, 20 min) and optical density at 420 nm was determined of supernatant. PhoA activity was determined according to the Lambert-Beer law. *E. coli* CC118 pGP1-2 cultures bearing the empty vector pECD637 served as negative control whereas *E. coli* CC118 pGP1-2 with pECD619 (Pribyl, 2001) served as positive control. This plasmid encodes a short form of β-lactamase ('blaM) inclusive signal sequence downstream of 'phoA domain.

Conclusion

In silico analysis of open reading frame of PgQC revealed a putative signal sequence. This indicates a localization of PgQC outside the cytoplasm in *P. gingivalis*. C-terminal fusions of PgQC inclusive "native" signal sequences with alkaline phosphatase (PhoA) were constructed to investigate the "nature" localization of PgQC. Fusions with alkaline phosphatases are exclusively active when localized in the periplasm. Expression of $_{seq}$PgQC-'PhoA resulted in high phosphatase activity of 638.5 U/l±50.9 (FIG. 5). This indicates that PgQC is localized in the periplasm.

VII. Description of Synthetic Methods a) Synthesis of 5-substituted imidazo[4,5-b]pyridineamines 5-substituted imidazo[4,5-b]pyridineamines were prepared by a general method comprising: treating 6-chloropyridine-2,3-diamine with triethyl orthoformate at elevated temperature to obtain 5-chloroimidazo[4,5-b]pyridine (Step A1); followed by a cross-coupling reaction of the product from Step A1 with a respective amine in the presence of a suitable Pd-catalyst and a base to obtain the corresponding 5-substituted imidazo[4,5-b]pyridineamine (Step A2).

The compound of Example 1 was prepared by the above method, as shown in the following Scheme 1.

Scheme 1: Synthetic scheme for the preparation of Example 1.

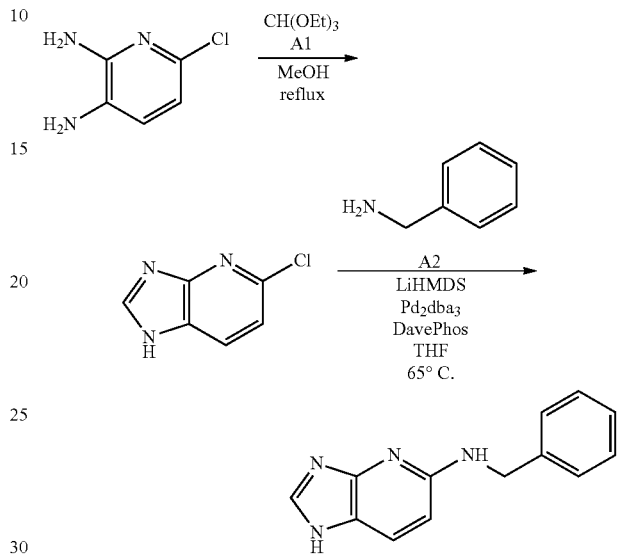

Example 1:
N-Benzylimidazo[4,5-b]pyridin-5-amine

Step A1: 5-Chloroimidazo[4,5-b]pyridine

A solution of 6-Chloropyridine-2,3-diamine (718 mg, 5 mmol) in Methanol (10 ml) and Triethyl orthoformate (10 ml) was heated to reflux for 3 hours. The volatiles were evaporated and the residue was purified by flash chromatography on silica using a CHCl$_3$-MeOH gradient. Yield: 540 mg (58%); ESI-MS m/z 151.1 [M+H]$^+$ Step A2: N-Benzylimidazo[4,5-b]pyridin-5-amine 5-Chloro[4,5-b]pyridine (207 mg, 1.1 mmol, 1 eq), DavePhos (10 mg, 0.0264 mmol, 0.25 eq) and Pd$_2$(dba)$_3$ (9 mg, 0.011 mmol, 0.1 eq) were dissolved in dry THF (15 ml) under Argon atmosphere. LN(TMS)$_2$ (1M in THF, 2.4 ml, 2.4 mmol, 2.2 eq) and benzylamine (144 μl, 1.3 mmol, 1.2 eq) were added and the mixture was stirred at 65° C. for 18 h. After cooling to room temperature the mixture was acidified by means of aqueous HCl (5 N) and stirring was continued for further 10 min. The reaction mixture was poured into saturated aqueous NaHCO$_3$ and extracted with EtOAc (3×25 ml). The combined organic layers were dried over MgCO$_3$ and evaporated to dryness. The residue was purified by semi-preparative HPLC. Yield: 90 mg (24%); MS m/z: 225.2 [M+H]: HPLC (Gradient A): rt 8.93 min. 100%; $^1$H-NMR (DMSO-d6) δ: 4.55 (s, 2H); 6.80 (d, 1H, $^3$J=8.8 Hz); 7.22-7.27 (m, 1H); 7.30-7.37 (m, 4H); 7.83-7.91 (m, 2H); 9.08 (s, 1H)

b) Synthesis of 6-Substituted imidazo[4,5-b]pyridineamines

6-Substituted imidazo[4,5-b]pyridineamines were prepared by a general method comprising the steps: treating 2-chloro-3,5-dinitropyridine with ammonia in a suitable solvent or solvent mixture to obtain 3,5-dinitropyridine-2-amine (Step B1); treating the product obtained in Step B1 with (NH$_4$)$_2$S to obtain 5-nitropyridin-2,3-diamine (Step B2); treating the product obtained in Step B2 with triethyl orthoformate to obtain 6-nitroimidazo[4,5-b]pyridine (Step B3); treating the product obtained in Step B3 with a suitable reducing agent to obtain imidazo[4,5-b]pyridin-6-amine (Step B4); followed by treating the product obtained in Step B4 with a respective aldehyde in the presence of a suitable reducing agent, such as NaBH$_4$, to obtain the corresponding N-alyklimidazo[4,5-b]pyridin-6-amine (Step B5).

A synthetic route according to the above general method is exemplified in Scheme 2 below.

further purification. Yield: 2.64 g (92%); ESI-MS m/z: 165.1 [M+H]$^+$; HPLC (Gradient A): rt 6.21 min, 100%

Step 4: Imidazo[4,5-b]pyridin-6-amine

A solution of 6-Nitroimidazo[4,5-b]pyridine (1240 mg, 7.5 mmol, 1 eq) in aqueous hydrochloric acid (10%) was treated with SnCl$_2$ (5076 mg, 22.5 mmol, 3 eq) and heated in a microwave to 100° C. for 30 minutes. After cooling to room temperature the mixture was basified by means of aqueous NaOH (1 M) and evaporated. The residue was suspended in MeOH and filtered. The filtrate was evaporated and the residue was purified by flash chromatography (silica,

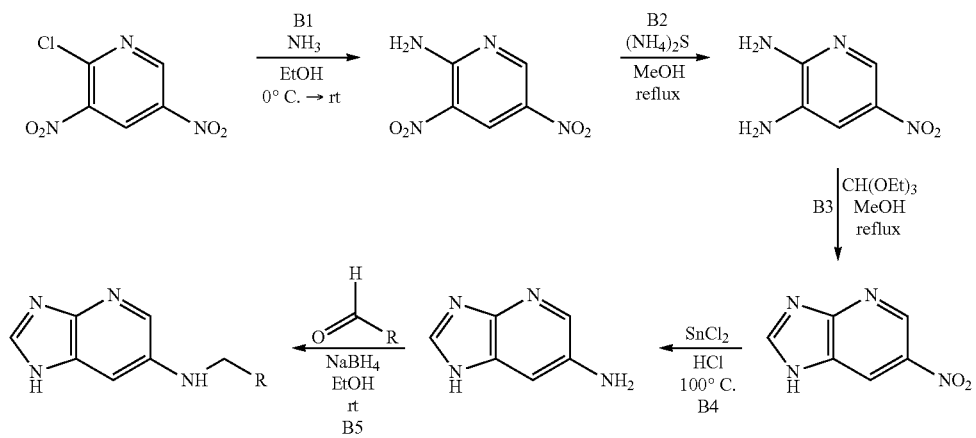

Scheme 2: Synthetic scheme for the preparation of 6-substituted imidazo[4,5-b]pyridineamines aa) Synthesis of Imidazo[4,5-b]pyridin-6-amine Step B1: 3,5-Dinitropyridin-2-amine A solution of 2-Chloro-3,5-dinitropyridine (5 g, 24.6 mmol, 1 eq) in Ethanol (150 ml) was treated dropwise with aqueous NH$_3$ (7 ml, 123 mmol, 5 eq) at 0° C. After complete addition, the mixture was stirred at ambient temperature for 1 hour. The solid product was collected by filtration and dried. The compound was used without further purification. Yield: 4.17 g (92%)

Step B2: 5-Nitropyridin-2,3-diamine

A solution of 3,5-Dinitropyridine-2-amine (3.9 g, 21.2 mmol, 1 eq) in Methanol (80 ml) was treated with 20% aqueous (NH$_4$)$_2$S (36.1 ml, 106 mmol, 5 eq) and heated to reflux for 1 hour. After cooling, the solid was collected by filtration and dried. The product was used without further purification. Yield: 3.2 g (98%); ESI-MS m/z: 155.0 [M+H]$^+$; HPLC (Gradient A): rt 4.08 min, 100%; $^1$H-NMR (DMSO-d6) δ: 5.31 (br s, 2H), 6.98 (br s, 2H), 7.36 (d, 1H, $^4$J=2.2 Hz), 8.28 (d, 1H, $^4$J=2.6 Hz)

Step 3: 6-Nitroimidazo[4,5-b]pyridine

A solution of 5-Nitropyridin-2,3-diamine (2.7 g, 17.5 mmol) in Methanol (14 ml) and Triethyl orthoformate (14 ml) was stirred at 150° C. in a microwave for 10 min. The solvents were evaporated and the residue was used without CHCl$_3$/MeOH gradient with 0.5% NH$_3$). Yield: 993 mg (98%); ESI-MS m/z: 135.2 [M+H]$^+$; HPLC (Gradient A): rt 1.47 min, 100% bb) General Procedure for the Synthesis of N-Alyklimidazo[4,5-b]pyridin-6-amines Step 5: N-Alyklimidazo[4,5-b]pyridin-6-amines Imidazo[4,5-b]pyridin-6-amine (1 eq) and the respective aldehyde (1 eq) were dissolved in EtOH (5 ml) and stirred at room temperature for 4 hours. NaBH$_4$ (1.5 eq) was added and stirring was continued over night. The reaction was quenched by means of water and extracted with EtOAc (3×20 ml). The combined organic layers were washed with brine, dried over Na$_2$SO$_4$ and evaporated. The residue was purified by flash chromatography (silica, CHCl$_3$/MeOH gradient).

The following examples of 6-substituted imidazo[4,5-b]pyridineamines were prepared by using the above described methods.

Example 2:
N-Benzylimidazo[4,5-b]pyridin-6-amine

The compound was synthesized starting from Imidazo[4,5-b]pyridin-6-amine (50 mg, 0.4 mmol) and Benzaldehyde (38 µl, 0.4 mmol) as described above. Yield: 30 mg (36%); MS m/z: 225.2 [M+H]$^+$; HPLC (Gradient A): rt 8.45 min, 100%; $^1$H-NMR (DMSO-d6) δ: 4.33 (s, 2H); 6.35 (br s, 1H);

6.93 (s, 1H); 7.21-7.26 (m, 1H); 7.31- 7.36 (m, 2H); 7.39-7.43 (m, 2H); 7.94 (d, 1H, $^4J$=2.6 Hz); 8.07 (s, 1H); 12.20 (br s, 1H).

Example 3: N-(3,4,5-Trifluorobenzyl)imidazo[4,5-b]pyridin-6-amine

The compound was synthesized starting from Imidazo[4,5-b]pyridin-6-amine (67 mg, 0.5 mmol) and 3,4,5-Trifluorobenzaldehyde (80 mg, 0.5 mmol) as described above. Yield: 74 mg (53%); MS m/z: 279.1 [M+H]$^+$; HPLC (Gradient A): rt 10.13 min, 100%; $^1$H-NMR (DMSO-d6) δ: 4.34 (d, 2H, $^3J$=5.7 Hz); 6.44 (br s, 1H); 6.94 (s, 1H); 7.31-7.39 (m, 2H); 7.92 (d, 1H, $^4J$=2.6 Hz); 8.10 (s, 1H); 12.16 (br s, 1H).

Example 4: N-(4-Chlorobenzyl)imidazo[4,5-b]pyridin-6-amine

The compound was synthesized starting from Imidazo[4,5-b]pyridin-6-amine (50 mg, 0.4 mmol) and 4-Chlorobenzaldehyde (52 mg, 0.4 mmol) as described above. Yield: 48 mg (50%); MS m/z: 259.1 [M+H]$^+$; HPLC (Gradient A): rt 9.97 min, 100%; $^1$H-NMR (DMSO-d6) δ: 4.33 (s, 2H); 6.39 (br s, 1H); 6.91 (s, 1H); 7.36-7.45 (m, 4H); 7.93 (d, 1H, $^4J$=2.5 Hz); 8.08 (s, 1H); 12.22 (br s, 1H).

Example 5: N-(3-Chlorobenzyl)imidazo[4,5-b]pyridin-6-amine

The compound was synthesized starting from Imidazo[4,5-b]pyridin-6-amine (50 mg, 0.4 mmol) and 3-Chlorobenzaldehyde (42 μl, 0.4 mmol) as described above. Yield: 70 mg (73%); MS m/z: 259.1 [M+H]$^+$; HPLC (Gradient A): rt 9.84 min, 100%; $^1$H-NMR (DMSO-d6) δ: 4.36 (d, 2H, $^3J$=5.9 Hz); 6.42 (s, 1H); 6.93 (s, 1H); 7.27-7.31 (m, 1H); 7.35-7.39 (m, 2H); 7.45-7.47 (m, 1H); 7.93 (d, 1H, $^4J$=2.3 Hz); 8.08 (s, 1H); 12.09 (br s, 1H).

Example 6: N-(3-Methoxybenzyl)imidazo[4,5-b]pyridin-6-amine

The compound was synthesized starting from Imidazo[4,5-b]pyridin-6-amine (50 mg, 0.4 mmol) and 3-Methoxybenzaldehyde (46 μl, 0.4 mmol) as described above. Yield: 40 mg (42%); MS m/z: 255.1 [M+H]$^+$; HPLC (Gradient A): rt 8.51 min, 97%; $^1$H-NMR (DMSO-d6) δ: 3.73 (s, 3H); 4.28-4.32 (m, 2H); 6.34 (br s, 1H); 6.80 (dd, 1H, $^3J$=8.1 Hz, $^4J$=1.9 Hz); 6.92 (s, 1H); 6.96-7.00 (m, 2H); 7.22-7.27 (m, 1H); 7.93 (d, 1H, $^4J$=2.5 Hz); 8.07 (s, 1H); 12.18 (br s, 1H).

Example 7: N-(4-Methoxybenzyl)imidazo[4,5-b]pyridin-6-amine

The compound was synthesized starting from Imidazo[4,5-b]pyridin-6-amine (50 mg, 0.4 mmol) and 3-Methoxybenzaldehyde (46 μl, 0.4 mmol) as described above. Yield: 25 mg (26%); MS m/z: 255.1 [M+H]$^+$; HPLC (Gradient A): rt 8.43 min, 97%; $^1$H-NMR (DMSO-d6) δ: 3.72 (s, 3H); 4.24 (s, 2H); 6.25 (br s, 1H); 6.85-6.97 (m, 3H); 7.29-7.35 (m, 2H); 7.92 (d, 1H, $^4J$=2.4 Hz); 8.06 (s, 1H); 12.13 (br s, 1H).

Example 8: N-(3-Thienylmethyl)imidazo[4,5-b]pyridin-6-amine

The compound was synthesized starting from Imidazo[4,5-b]pyridin-6-amine (50 mg, 0.4 mmol) and Thiophene-3-carbaldehyde (33 μl, 0.4 mmol) as described above. Yield: 60 mg (70%); MS m/z: 231.2 [M+H]$^+$; HPLC (Gradient A): rt 7.63 min, 100%; $^1$H-NMR (DMSO-d6) δ: 4.31 (s, 2H); 7.03 (d, 1H, $^4J$=2.5 Hz); 7.13 (dd, 1H, $^3J$=4.9 Hz, $^4J$=1.1 Hz); 7.37-7.40 (m, 1H); 7.49 (dd, 1H, $^3J$=4.9 Hz, $^4J$=3.0 Hz); 7.96 (d, 1H, $^4J$=2.5 Hz).

Example 9: N-(3-(1-Piperidyl)benzyl)imidazo[4,5-b]pyridin-6-amine

The compound was synthesized starting from Imidazo[4,5-b]pyridin-6-amine (50 mg, 0.4 mmol) and 3-(1-Piperidyl)benzaldehyde (71 mg, 0.4 mmol) as described above. Yield: 56 mg (49%); MS m/z: 308.3 [M+H]$^+$; HPLC (Gradient A): rt (double peak) 5.17/5.49 min, 100%; $^1$H-NMR (DMSO-d6) δ: 1.48-1.63 (m, 6H); 3.07-3.14 (m, 4H); 4.25 (s, 2H); 6.76-6.81 (m, 2H); 6.95 (d, $^4J$=2.5 Hz); 6.99 (s, 1H); 7.14 (t, 1H, 3J=7.8 Hz); 7.96 (d, 1H, 4J=2.5 Hz); 8.15 (s, 1H).

Example 10: N-(2-Pyridylmethyl)imidazo[4,5-b]pyridin-6-amine

The compound was synthesized starting from Imidazo[4,5-b]pyridin-6-amine (50 mg, 0.4 mmol) and Pyridine-2-carbaldehyde (35 μl, 0.4 mmol) as described above. Yield: 6 mg (7%); MS m/z: 226.2 [M+H]$^+$; HPLC (Gradient B): rt 4.96 min, 100%; $^1$H-NMR (DMSO-d6) δ: 4.43 (s, 2H); 6.97 (d, 1H, $^4J$=2.5 Hz); 7.25-7.30 (m, 1H); 7.42 (d, 1H, $^3J$=7.8 Hz); 7.72-7.78 (m, 1H); 8.01 (d, 1H, $^4J$=2.5 Hz); 8.27 (s, 1H); 8.55 (d, 1H, $^3J$=4.5 Hz).

Example 11: N-(3-Pyridylmethyl)imidazo[4,5-b]pyridin-6-amine

The compound was synthesized starting from Imidazo[4,5-b]pyridin-6-amine (50 mg, 0.4 mmol) and Pyridine-3-carbaldehyde (35 μl. 0.4 mmol) as described above. Yield: 15 mg (18%); MS m/z: 226.2 [M+H]1; HPLC (Gradient B): rt 4.64 min, 94%; $^1$H-NMR (DMSO-d6) δ: 4.38 (s, 2H); 7.01 (d, 1H, $^4J$=2.5 Hz); 7.34-7.39 (m, 1H); 7.78-7.83 (m, 1H); 7.97 (d, 1H, $^4J$=2.5 Hz); 8.21 (s, 1H); 8.46 (dd, 1H, $^3J$=4.7 Hz, 4J=1.4 Hz); 8.64 (d, 1H, 4J=1.6 Hz).

Example 12: N-(2,3-Dihydro-1,4-benzodioxin-6-ylmethyl)imidazo[4,5-b]pyridin-6-amine The compound was synthesized starting from Imidazo[4,5-b]pyridin-6-amine (50 mg, 0.4 mmol) and 1,4-Benzodioxane-6-carbaldehyde (61 mg, 0.4 mmol) as described above. Yield: 21 mg (20%); MS m/z: 283.2 [M+H]$^+$; HPLC (Gradient A): rt 8.59 min, 96%; $^1$H-NMR (DMSO-d6) δ: 4.16-4.23 (m, 6H); 6.27 (br s, 1H); 6.77-6.94 (m, 4H); 7.91 (d, 1H, $^4J$=2.5 Hz); 8.08 (s, 1H); 12.25 (br s, 1H).

Example 13: N-(3,4-Dimethoxybenzyl)imidazo[4,5-b]pyridin-6-amine

The compound was synthesized starting from Imidazo[4,5-b]pyridin-6-amine (134 mg, 1 mmol) and 3,4-Dimethoxybenzaldehyde (166 mg, 1 mmol) as described above. Yield: 90 mg (32%); MS m/z: 285.2 [M+H]$^+$; HPLC (Gradient A): rt 7.79 min, 100%; $^1$H-NMR (DMSO-d6) δ: 3.70-3.76 (m, 6H); 4.24 (s, 2H); 6.24 (br s, 1H); 6.87-6.97 (m, 3H); 7.01-7.04 (m, 1H); 7.93 (d, 1H, $^4J$=2.3 Hz); 8.07 (s, 1H); 12.16 (br s, 1H).

Example 14: N-(3,4-Dichlorobenzyl)imidazo[4,5-b]pyridin-6-amine

The compound was synthesized starting from Imidazo[4,5-b]pyridin-6-amine (50 mg, 0.4 mmol) and 3,4-Dichlorobenzaldehyde (65 mg, 0.4 mmol) as described above. Yield: 75 mg (69%); MS m/z: 293.1 [M+H]$^+$; HPLC (Gradient A): rt 11.09 min, 100%; $^1$H-NMR (DMSO-d6) δ: 4.36 (s, 2H); 6.45 (br s, 1H); 6.94 (d, 1H, $^4$J=1.6 Hz); 7.39 (dd, 1H, $^3$J=8.3 Hz, $^4$J=1.7 Hz); 7.59 (d, 1H, $^3$J=8.3 Hz); 7.66 (d, 1H, $^4$J=1.6 Hz); 7.93 (d, 1H, $^4$J=2.5 Hz); 8.09 (s, 1H); 12.25 (br s, 1H).

Example 15: N-(4-Propoxybenzyl)imidazo[4,5-b]pyridin-6-amine

The compound was synthesized starting from Imidazo[4,5-b]pyridin-6-amine (134 mg, 1 mmol) and 4-Propoxybenzaldehyde (158 μl, 1 mmol) as described above. Yield: 110 mg (39%); MS m/z: 283.3 [M+H]$^+$; HPLC (Gradient A): rt 11.07 min, 100%; $^1$H-NMR (DMSO-d6) δ: 0.96 (t, 3H, $^3$J=7.4 Hz); 1.70 (sext, 2H, $^3$J=7.0 Hz); 3.88 (t, 2H, $^3$J=6.5 Hz); 4.24 (s, 2H); 6.84-6.97 (m, 3H); 7.27-7.34 (m, 2H); 7.93 (d, 1H, $^4$J=1.4 Hz); 8.07 (s, 1H); 12.18 (br s, 1H).

Example 16: N-(4-(2-Aminoethoxy)benzyl)imidazo[4,5-b]pyridin-6-amine

The compound was synthesized starting from Imidazo[4,5-b]pyridin-6-amine (268 mg, 2 mmol) and N-Boc-(4-(2-Aminoethoxy)benzaldehyde (531 mg, 2 mmol) as described above, followed by Boc-deprotection using TFA/DCM (1:1, 2 ml) and TIS (100 μl) and purification by semi-preparative HPLC. Yield: 53 mg (9%); MS m/z: 284.1 [M+H]$^+$; HPLC (Gradient A): rt 5.12 min, 100%; $^1$H-NMR (DMSO-d6) δ: 3.18-3.25 (m, 2H); 4.13 (t, 2H, $^3$J=5.0 Hz); 4.31 (s, 2H); 6.94-6.99 (m, 2H); 7.07 (d, 1H, $^4$J=2.4 Hz); 7.33-7.38 (m, 2H); 7.91-8.01 (m, 3H); 8.09 (d, 1H, $^4$J=2.4 Hz); 8.85 (s, 1H).

Example 17: 1-(2-(4-((Imidazo[4,5-b]pyridin-6-ylamino)methyl)-phenoxy)ethyl)guanidine A solution of N-(4-(2-Aminoethoxy)benzyl)imidazo[4,5-b]pyridin-6-amine*TFA (41 mg, 0.08 mmol, 1 eq) in DMF was treated with N,N'-Bis(tert-butoxycarbonyl)-S-methyl-isothiourea (23 mg, 0.08 mmol, 1 eq), DMAP (1 mg, 0.008 mmol, 0.1 eq) and TEA (33 μl, 0.24 mmol, 3 eq). The mixture was stirred for 16 hours at room temperature, quenched with water and extracted with EtOAc (3×20 ml). The combined organic layers were dried over MgCO$_3$ and evaporated. Boc deprotection was carried out with TFA/DCM (1:1, 2 ml) and TIS (100 μl). The volatiles were evaporated and the residue was purified by semi-preparative HPLC. Yield: 18 mg (41%); MS m/z: 326.1 [M+H]$^+$; HPLC (Gradient A): rt 5.95 min, 100%; $^1$H-NMR (DMSO-d6) δ: 4.04 (t, 2H, $^3$J=5.3 Hz); 4.30 (s, 2H); 6.91-6.95 (m, 2H); 7.07 (d, 1H, $^4$J=2.5 Hz); 7.32-7.36 (m, 2H); 7.64 (t, 1H, $^3$J=5.8 Hz); 8.09 (d, 1H, $^4$J=2.4 Hz); 8.86 (s, 1H).

Example 18: N-[(4-Isopropoxyphenyl)methyl]-3H-imidazo[4,5-b]pyridin-6-amine

The compound was synthesized starting from Imidazo[4,5-b]pyridin-6-amine (67 mg, 0.5 mmol) and 4-Isopropoxybenzaldehyde (78 μl, 0.5 mmol) as described above. Yield: 6 mg (4%); MS m/z: 283.2 [M+H]$^+$; HPLC (Gradient A): rt 10.69 min, 89.7%; $^1$H-NMR (DMSO-d6) δ: 1.23 (d, 6H, $^3$J=5.9 Hz), 4.20-4.24 (m, 2H), 4.50-4.60 (m, 1H), 6.83-6.89 (m, 3H), 7.26-7.32 (m, 2H), 7.92 (br s, 1H), 8.05 (br s, 1H), 12.02 (br s, 1H)

Example 19: N-[(3-Phenoxyphenyl)methyl]-3H-imidazo[4,5-b]pyridin-6-amine

The compound was synthesized starting from Imidazo[4,5-b]pyridin-6-amine (50 mg, 0.4 mmol) and 3-Phenoxybenzaldehyde (64 μl, 0.4 mmol) as described above. Yield: 19 mg (16%); MS m/z: 317.3 [M+H]$^+$; HPLC (Gradient A): rt 12.13 min, 100%; $^1$H-NMR (DMSO-d6) δ: 4.30-4.36 (m, 2H), 6.41 (br s, 1H), 6.80-6.97 (m, 4H), 7.02- 7.20 (m, 3H), 7.28-7.36 (m, 3H), 7.82-8.16 (m, 2H), 12.03 (br s, 1H)

Example 20: N-[(4-Benzyloxyphenyl)methyl]-3H-imidazo[4,5-b]pyridin-6-amine

The compound was synthesized starting from Imidazo[4,5-b]pyridin-6-amine (50 mg, 0.4 mmol) and 3-Benzyloxybenzaldehyde (79 mg, 0.4 mmol) as described above. Yield: 47 mg (38%); MS m/z: 331.2 [M+H]$^+$; HPLC (Gradient A): rt 12.59 min, 97.8%; $^1$H-NMR (DMSO-d6) δ: 4.22-4.26 (m, 2H), 5.06 (s, 2H), 6.24 (br s, 1H), 6.86-7.00 (m, 3H), 7.28-7.45 (m, 7H), 7.90-7.93 (m, 1H), 8.05 (s, 1H), 12.05 (br s, 1H)

Example 21: N-[(4-Biphenyl)methyl]-3H-imidazo[4,5-b]pyridin-6-amine

The compound was synthesized starting from Imidazo[4,5-b]pyridin-6-amine (50 mg, 0.4 mmol) and 4-Biphenylcarboxaldehyde (68 mg, 0.4 mmol) as described above. Yield: 30 mg (27%); MS m/z: 301.2 [M+H]$^+$; HPLC (Gradient A): rt 12.37 min, 100%; $^1$H-NMR (DMSO-d6) δ: 4.37 (d, 2H, $^3$J=5.4 Hz), 6.40 (br s, 1H), 6.94 (br s, 1H), 7.31-7.37 (m, 1H), 7.41-7.51 (m, 4H), 7.60-7.67 (m, 4H), 7.95 (s, 1H), 8.06 (s, 1H), 12.04 (br s, 1H)

Example 22: N-[(2,6-Difluoro-4-methoxy-phenyl)methyl]-3H-imidazo[4,5-b]pyridin-6-amine The compound was synthesized starting from Imidazo[4,5-b]pyridin-6-amine (67 mg, 0.5 mmol) and 2,6-difluoro-4-methoxybenzaldehyde (86 mg, 0.4 mmol) as described above. Yield: 77 mg (53%); MS m/z: 291.2 [M+H]$^+$; HPLC (Gradient A): rt 9.60 min, 100%; $^1$H-NMR (DMSO-d6) δ: 3.76 (s, 3H), 4.22 (d, 2H, $^3$J=5.9 Hz), 5.97 (br s, 1H), 6.71-6.79 (m, 2H), 7.10 (br s, 1H), 7.92 (s, 1H), 8.09 (s, 1H), 12.16 (br s, 1H)

Example 23: N-[(7-Methoxy-1,3-benzodioxol-5-yl)methyl]-3H-imidazo-[4,5-b]pyridin-6-amine The compound was synthesized starting from Imidazo[4,5-b]pyridin-6-amine (60 mg, 0.45 mmol) and 5-Methoxypiperonal (81 mg, 0.45 mmol) as described above. Yield: 44 mg (33%); MS m/z: 299.2 [M+H]$^+$; HPLC (Gradient A): rt 8.91 min, 100%; $^1$H-NMR (DMSO-d6) δ: 3.80 (s, 3H), 4.21 (s, 2H), 5.93 (s, 2H), 6.27 (br s, 1H), 6.63 (s, 1H), 6.72 (s, 1H), 6.94 (s, 1H), 7.91 (s, 1H), 8.07 (s, 1H), 12.23 (br s, 1H)

Example 24: N-[(2,2-Difluoro-1,3-benzodioxol-5-yl)methyl]-3H-imidazo-[4,5-b]pyridin-6-amine The compound was synthesized starting from Imidazo[4,5-b]pyridin-6-amine (67 mg, 0.5 mmol) and 2,2-Difluoro- 1,3-benzodioxole-5-carboxaldehyde (93 mg, 0.5 mmol) as described above. Yield: 60 mg (40%); MS m/z: 305.3 [M+H]$^+$; HPLC (Gradient A): rt 11.07 min, 100%; $^1$H-NMR (DMSO-d6) δ: 4.34 (d, 2H, $^3$J=6.4 Hz), 6.45/6.26 (br s, 1H, Rotamer), 6.85/7.08 (br s, 1H, Rotamer), 7.22-7.31 (m, 1H), 7.33-7.38 (m, 1H), 7.43 (s, 1H), 7.85-8.15 (m, 2H), 12.02/12.59 (br s, 1H)

Example 25: N-[[4-(2-Pyridyl)phenyl]methyl]-3H-imidazo[4,5-b]pyridin-6-amine

The compound was synthesized starting from Imidazo[4,5-b]pyridin-6-amine (67 mg, 0.5 mmol) and 4-(2-Pyridyl)benzaldehyde (92 mg, 0.5 mmol) as described above. Yield: 25 mg (17%); MS m/z: 302.4 [M+H]$^+$; HPLC (Gradient A): rt 6.00 min, 100%; $^1$H-NMR (DMSO-d6) δ: 4.39 (d, 2H, $^3$J=5.9 Hz), 6.45 (br s, 1H), 7.29-7.35 (m, 1H), 7.51 (d, 2H, $^3$J=8.3 Hz), 7.82-7.88 (m, 1H), 7.91-7.98 (m, 2H), 8.02-8.09 (m, 3H), 8.64 (d, 2H, $^3$J=4.9 Hz), 12.02 (br s, 1H)

Example 26: N-[[4-(2-Morpholinoethoxy)phenyl]methyl]-3H-imidazo[4,5-b]pyridin-6-amine The compound was synthesized starting from Imidazo[4,5-b]pyridin-6-amine (67 mg, 0.5 mmol) and 4-(2-Morpholinoethoxy)benzaldehyde (118 mg, 0.5 mmol) as described above. Yield: 21 mg (12%); MS m/z: 177.6 [M+2H]$^2$+, 354.4 [M+H]$^+$; HPLC (Gradient A): rt 5.76 min, 100%; $^1$H-NMR (MeOH-d4) δ: 2.55-2.61 (m, 4H), 2.78 (t, 2H, $^3$J=5.4 Hz), 3.67-3.72 (m, 4H), 4.11 (t, 2H, $^3$J=5.4 Hz), 4.30 (s, 2H), 6.87-6.93 (m, 2H), 7.02 (br s, 1H), 7.29-7.35 (m, 2H), 7.94 (s, 1H), 8.05 (s, 1H)

Example 27: N-[(4-morpholinophenyl)methyl]-3H-imidazo[4,5-b]pyridin-6-amine

The compound was synthesized starting from Imidazo[4,5-b]pyridin-6-amine (67 mg, 0.5 mmol) and 4-(4-Morpholinyl)benzaldehyde (96 mg, 0.5 mmol) as described above. Yield: 42 mg (26%); MS m/z: 310.4 [M+H]$^+$; HPLC (Gradient A): rt 6.91 min, 93.9%; $^1$H-NMR (MeOH-d4) δ: 3.07-3.11 (m, 4H), 3.79-3.82 (m, 4H), 4.29 (s, 2H), 6.91-6.96 (m, 2H), 7.01 (br s, 1H), 7.27-7.32 (m, 2H), 7.95 (br s, 1H), 8.04 (br s, 1H)

cc) General Procedure for the Synthesis of N-Benzylimidazo[4,5-b]pyridin-6-amine-porphyrin Conjugates Step C1

Imidazo[4,5-b]pyridine-6-amine (1 eq) was dissolved in MeOH or EtOH (c=0.05-0.08 M). The respective aldehyde was added and the mixture was stirred at room temperature until TLC indicated complete turnover of the starting materials. NaBH$_4$ (1.5 eq) (in the case of R$^{a/b}$=$^1$H) or NaBD$_4$ (1.7 eq) (in the case of R$^{a/b}$=D), respectively, was added carefully and stirring was continued overnight. The volatiles were evaporated and the residue was purified by flash chromatography (Al$_2$O$_3$, CHCl$_3$/MeOH gradient).

The purified product was dissolved in MeOH (c=0.06-0.12 M) and treated with freshly prepared 1M HCl in MeOH (16 eq). After stirring at room temperature for 3 h, the volatiles were evaporated and the residue was used without further purification.

Scheme 3: Exemplary synthetic scheme for the synthesis of N-Benzylimidazo[4,5-b]pyridine-6-amine-porphyrin conjugates

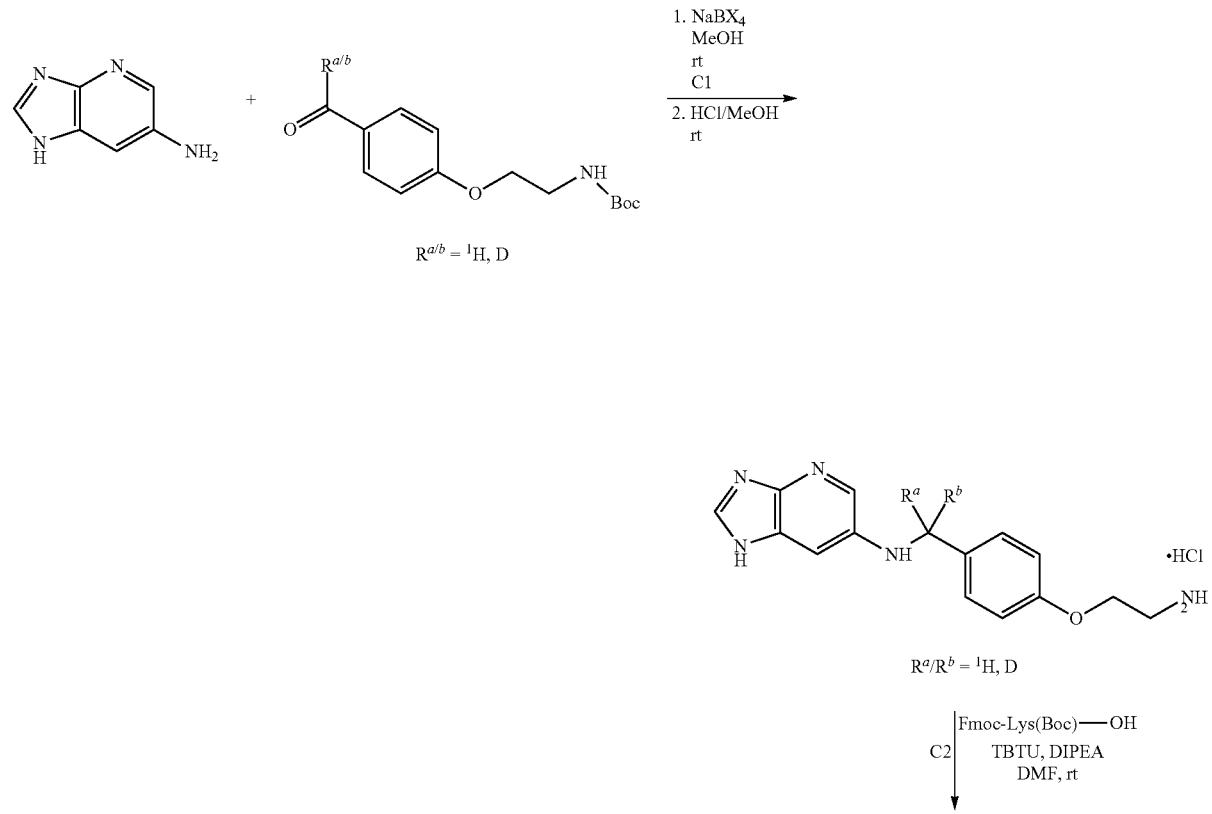

porphyrin = 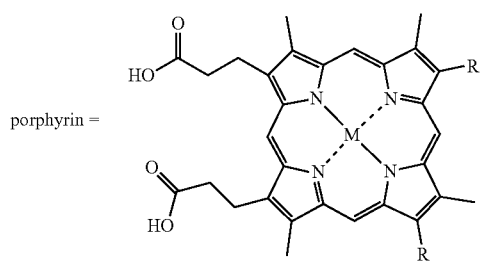

Me = $Fe^{2+}$, $Fe^{3+}$ or absent

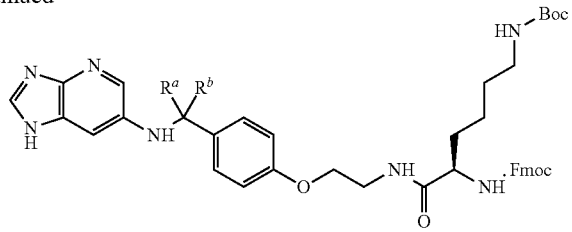

C3 | 1. DBU, DMF, rt
2. TBTU, DIPEA, HOBt, porphyrin, rt
3. TFA/DCM, rt

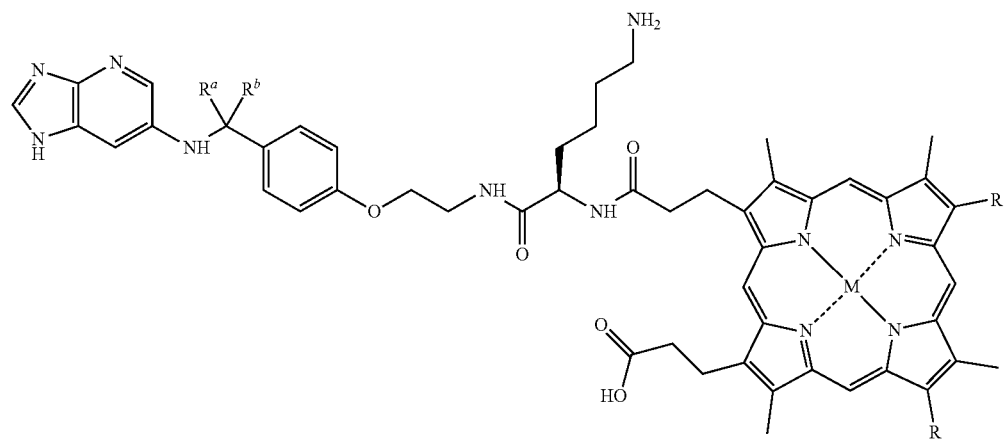

$R^a/R^b = {}^1H, D$

Step C2

N-[[4-(2-Aminoethoxy)phenyl]-methyl]-1H-imidazo[4,5-b]pyridin-6-amine or N-[[4-(2-aminoethoxy)-phenyl]dideuterio-methyl]-1H-imidazo[4,5-b]pyridin-6-amine (1 eq) obtained by step C1 was dissolved in dimethylformamide (c=0.1-0.13 M). Fmoc-Lys(Boc)-OH (1.2 eq), TBTU (1.2 eq) and DIPEA (4 eq) were added and the mixture was stirred at room temperature for 4-5 hours. Water was added and extracted with EtOAc (3×100 ml). The combined organic layers were dried over $Na_2SO_4$ and evaporated. The residue was purified by flash chromatography ($Al_2O_3$, $CHCl_3$/MeOH gradient).

Step C3

The respective product obtained by step C2 (1 eq) was dissolved in dimethylformamide (c=0.03 M), treated with DBU (1 eq) and stirred at room temperature for 30-40 minutes. A suitable porphyrin (1.2 eq), HOBt (1.2 eq), TBTU (1 eq) and DIPEA (4 eq) were dissolved in dimethylformamide, premixed for 50 minutes at room temperature and added to the solution. The mixture was stirred at room temperature overnight. The reaction was carefully quenched by addition of TFA/DCM (1:1 v/v, 10 ml) and stirring was continued for 45 minutes. The volatiles were evaporated and the crude mixture was directly subjected to semi-preparative HPLC.

Example 28: 3-[(1Z,4Z,9Z,15Z)-18-[3-[[(1S)-5-Amino-1-[2-[4-[(3H-imidazo[4,5-b]pyridin-6-ylamino)methyl]phenoxy]-ethylcarbamoyl]pentyl]amino]-3-oxo-propyl]-3,8,13,17-tetramethyl-21,23-dihydroporphyrin-2-yl]-propanoic Acid

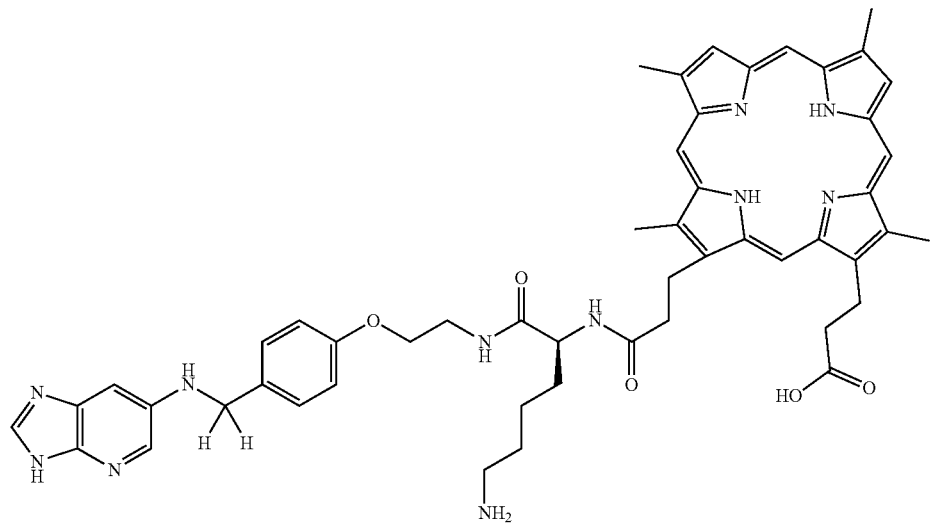

Yield (last step): 15 mg (6%); MS m/z: 453.1 [M+2H]$^{2+}$; 904.8 (M+H)$^{+}$ HPLC (Gradient A): rt 12.43 min, 94%; $^1$H-NMR (DMSO-d6) δ: 0.96-1.53 (m, 8H), 2.40-2.48 (m, 3H), 3.02-3.26 (m, 5H), 3.59-3.80 (m, 12H), 4.20- 4.26 (m, 2H), 4.26-4.33 (m, 2H), 4.33-4.45 (m, 2H), 6.70 (d, 2H, J=8.7 Hz), 7.04-7.08 (m, 1H), 7.17-7.24 (m, 2H), 7.42-7.51 (m, 3H), 7.87 (t, 1H, $^3$J=5.4 Hz), 8.05-8.12 (m, 2H), 8.97 (br s, 1H), 9.34 (d, 1H, J=24.0 Hz), 9.35 (s, 1H), 10.19 (d, 1H, J=8.6 Hz), 10.32 (s, 1H), 10.33 (d, 2H, J=9.8 Hz) 12.34 (br s, 1H).

Example 29: 3-[(4Z,10Z,15Z,19Z)-18-[3-[[(1S)-5-amino-1-[2-[4-[dideuterio-(1H-imidazo[4,5-b]pyridin-6-ylamino)-methyl]phenoxy]ethylcarbamoyl]pentyl]amino]-3-oxo-propyl]-3,8,13,17-tetramethyl-22,24-dihydro-porphyrin-2-yl]propanoic Acid

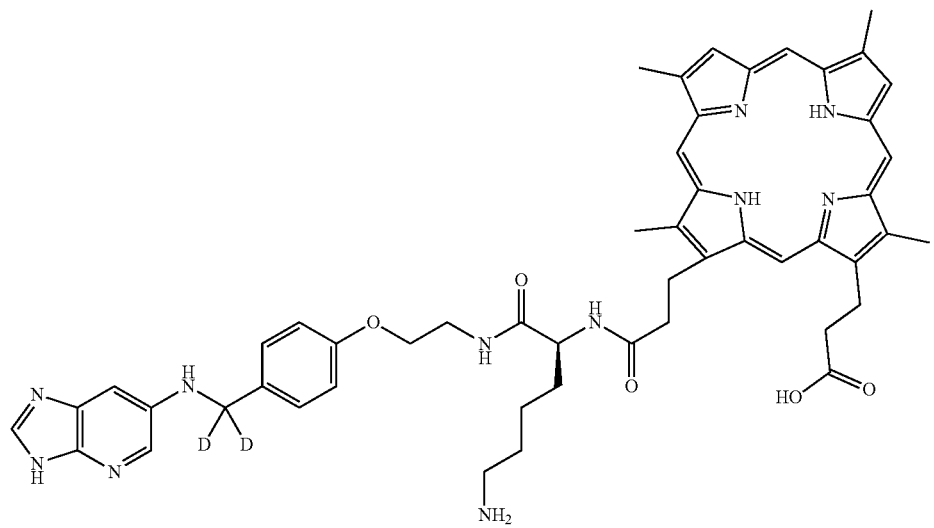 [SMILES: [2H]C([2H])(Nc1cnc2[nH]cnc2c1)c1ccc(OCCNC(=O)[C@H](CCCCN)NC(=O)CCc2c(C)c3cc4nc(cc5[nH]c(cc6nc(cc2[nH]3)C(CCC(=O)O)=C6C)cc5C)C=C4C)cc1]

Yield (last step): 37 mg (26%); MS m/z: 453.9 $[M+2H]^{2+}$; 906.4 (M+H) HPLC (Gradient A): rt 12.45 min, >99%; $^1$H-NMR (DMSO-d6) δ: 0.96-1.53 (m, 6H), 2.40-2.48 (m, 2H), 3.02-3.26 (m, 6H), 3.59-3.80 (m, 14H), 4.26-4.45 (m, 5H), 6.70 (d, 2H, J=8.4 Hz), 7.04-7.08 (m, 1H), 7.17-7.24 (m, 2H), 7.42-7.51 (m, 3H), 7.87 (m, 1H), 8.05-8.12 (m, 2H), 8.98 (br s, 1H), 9.34 (d, 1H, J=23.7 Hz), 9.35 (s, 1H), 10.28 (d, 1H, J=8.4 Hz), 10.31 (s, 1H), 10.33 (d, 2H, J=10.0 Hz).

c) Analytical Methods

HPLC: The analytical HPLC-system consisted of a Merck-Hitachi device (model LaChrom) utilizing a LUNA RP 18 (5 μm), analytical column (length: 125 mm, diameter: 4 mm), and a diode array detector (DAD) with λ=214 nm as the reporting wavelength. The compounds were analyzed using a gradient at a flow rate of 1 mL/min; whereby eluent (A) was acetonitrile, eluent (B) was water, both containing 0.04% (v/v) trifluoroacetic acid applying one of the following gradients:

Gradient A: 0 min—5% (A), 15 min—60% (A), 20 min—95% (A), 30 min—95% (A), 31 min—5% (A), 35 min—5% (A)

Gradient B: 0 min—1% (A), 5 min—1% (A), 20 min—20% (A), 30 min—95% (A), 34 min—95% (A), 35 min—1% (A), 37 min—1% (A)

The purities of all reported compounds were determined by the percentage of the peak area at 214 nm.

Mass-Spectrometry

ESI- & APCI-Mass spectra were obtained with a SCIEX API 1200 spectrometer (Perkin Elmer) or an expression CMS (Advion).

NMR-Spectroscopy

The 1H NMR-Spectra were recorded at an Agilent DD2 400-MHz spectrometer. Chemical shifts are expressed as parts per million (ppm) downfield from tetramethylsilane. Splitting patterns have been designated as follows: s (singlet), d (doublet), dd (doublet of doublet), t (triplet), m (multiplet) and br (broad signal).

INDUSTRIAL APPLICABILITY

The crystals and co-crystals according to the present invention are crystals of therapeutic target proteins (bacterial glutaminyl cyclases, bacQCs) and can be specifically and substantially used for identifying inhibitors capable of selective targeting of periodontitis-inducing pathogens by using the methods for identifying candidate compounds which may associate with the binding pocket of a bacQC and/or are bacQC inhibitors disclosed herein.

Thus, the crystals are relevant to the treatment of a particular disease, e.g. periodontitis, and, accordingly, susceptible to industrial applicability.

The methods for identifying candidate compounds which may associate with the binding pocket of a bacQC and/or are bacQC inhibitors according to the present invention are industrially applicable in view of the pharmaceutical relevance of the bacQC enzymes to the occurrence of periodontitis and their essentiality for the growth of periodontal pathogens demonstrated herein.

The compounds according to the present invention, including compounds identified by the methods for identifying candidate compounds which may associate with the binding pocket of a bacQC and/or are bacQC inhibitors, and the pharmaceutical composition according to the present invention are also susceptible to industrial applicability, because these can be used in methods for treatment of the human or animal body, in particular in a method for therapy or prophylaxis of a bacterial infection, e.g. a bacterial infection caused by a bacterium selected from the group consisting of *Porphyromonas gingivalis*, *Prevotella intermedia* and *Tannerella forsythia*, and/or in a method for therapy or prophylaxis of an acute, chronic or recurrent periodontal disease, e.g. periodontitis.

The research activities leading to these results were supported by the European Union.

---

The invention claimed is:

1. A compound according to the following Formula I,

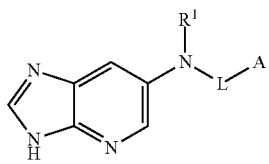

its individual enantiomers, its individual diastereoisomers, its hydrates, its solvates, its crystal forms, its individual tautomers or a pharmaceutically acceptable salt thereof, wherein:

A is selected from the group consisting of optionally substituted aryl, optionally substituted heterocyclyl, optionally substituted cycloalkyl and optionally substituted alkenyl;

$R^1$ is independently selected from the group consisting of H and optionally substituted alkyl;

L is

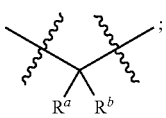

$R^a$ and $R^b$ are the same or different from each other and are independently selected from the group consisting of H, halo, optionally substituted alkyl, optionally substituted aryl, optionally substituted heteroalkyl and optionally substituted heteroaryl, and wherein $R^a$ and $R^b$ can optionally be joined together to form a carbocyclic or a heterocyclic ring.

2. The compound according to claim 1, wherein:

said aryl is independently a $C_{6-10}$, preferably $C_6$ aryl group;

said heterocyclyl is independently a monocyclic or bicyclic $C_{1-11}$, preferably $C_{2-8}$, more preferably $C_{4-5}$ heterocyclic group comprising 1 to 4 ring heteroatoms selected from N, S and O;

said alkyl is independently a linear or branched, open-chained or cyclic $C_{1-6}$, preferably $C_{1-4}$, more preferably $C_{1-3}$, even more preferably $C_{1-2}$ alkyl group;

said cycloalkyl is independently a cyclic $C_{3-6}$, preferably $C_{4-6}$, more preferably $C_{5-6}$ alkyl group;

said alkenyl is independently a linear or branched, open-chained or cyclic $C_{2-6}$, preferably $C_{2-4}$, more preferably $C_2$ group comprising at least one C=C bond;

said heteroaryl is independently an aromatic monocyclic or bicyclic $C_{1-11}$, preferably $C_{2-8}$, more preferably $C_{4-5}$ heterocyclic group comprising 1 to 4 ring heteroatoms selected from N, S and O; and said heteroalkyl is independently a linear or branched, open-chained or cyclic $C_{1-5}$, preferably $C_{1-3}$, more preferably $C_{1-2}$ heteroalkyl group comprising 1 to 4 heteroatoms selected from N, S and O.

3. The compound according to claim 1, which is represented by the following Formula Ia,

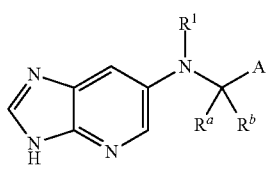

wherein A is selected from optionally substituted aryl and optionally substituted heteroaryl; and $R^1$, $R^a$ and $R^b$ are H.

4. The compound according to claim 1, wherein $R^a$ and $R^b$ are independently selected from $^1$H and D.

5. The compound according to claim 1, wherein A is substituted by at least one substituent represented by the following structure B:

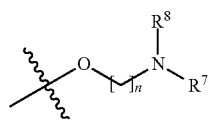

wherein n=1, 2, 3, 4, 5 or 6; and $R^7$ and $R^8$ are independently selected from alkyl, aryl, heteroalkyl, heteroaryl, carbamimidoyl, formyl, alkylacyl and arylacyl, each of which can optionally be further substituted and wherein $R^7$ and $R^8$ can be optionally joined together to form a carbocyclic or a heterocyclic ring.

6. The compound according to claim 5, wherein $R^7$ is represented by the following structure E:

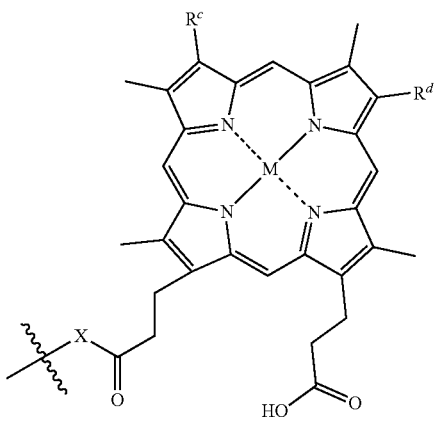

wherein M is selected from $Fe^{2+}$ and $Fe^{3+}$ or is absent;
$R^c$ and $R^d$ are independently selected from —H, —$CH_3$, —CH=$CH_2$, —$SO_3H$ and —CH(OH)$CH_2$OH; and
X is selected from a covalent bond, an alkylene, aralkylene, heteroalkylene, carbocyclene, heterocyclene, heteroarylene, heteroaralkylene, aminoalkylene, alkylamino and carbonyl-alkylamino group; wherein each of these may have up to 12 carbon atoms and up to 11 heteroatoms in the main chain, and may be substituted by one or more $C_{1-6}$ alkyl group(s), $C_{1-6}$ heteroalkyl group(s), $C_{1-6}$ carbocyclyl group(s), $C_{1-5}$ heterocyclyl group(s), $C_{1-5}$ heteroaryl group(s), halogen atom(s), hydroxyl group(s), cyano group(s), primary, secondary or tertiary amino group(s), carboxyl group(s) and side chain(s) derived from proteinogenic or non-proteinogenic aminoacid(s).

7. The compound according to claim 6, wherein X is represented by the following structure:

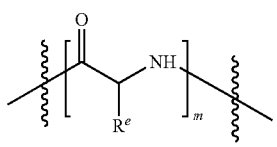

wherein m=0, 1, 2 or 3, and
$R^e$ is a side chain derived from a proteinogenic amino acid.

8. The compound according to claim 1, wherein A is substituted by a substituent represented by the following structure F:

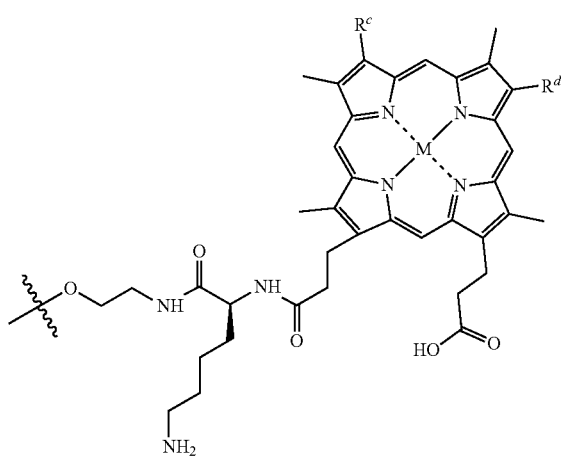

wherein M is selected from $Fe^{2+}$ and $Fe^{3+}$ or is absent; and
$R^c$ and $R^d$ are independently selected from —H, —$CH_3$, —CH=$CH_2$, —$SO_3H$ and —CH(OH)$CH_2$OH.

9. A pharmaceutical composition comprising the compound according to claim 1, or an enantiomer, a diastereoisomer, a hydrate, a solvate, a crystal form, a tautomer or a pharmaceutically acceptable salt thereof, or a pharmaceutical composition comprising the compound, an enantiomer, a diastereoisomer, a hydrate, a solvate, a crystal form, a tautomer or a pharmaceutically acceptable salt thereof, and a pharmaceutically acceptable excipient.

10. The compound according to claim 1, wherein optionally substituted refers to optional substitution by one or several groups independently selected from: $C_{1-6}$ alkyl, $C_{1-6}$ heteroalkyl, $C_{1-6}$ carbocyclyl, $C_{1-5}$ heterocyclyl and $C_{1-5}$ heteroaryl group, each of which may be substituted by one or several halogen atoms and/or hydroxyl groups; a halogen atom; a cyano group; a primary, secondary or tertiary amino group; a hydroxyl group;
and a carboxyl group.

11. The compound according to claim 1, wherein A in Formula I is selected from the group consisting of alkoxyaryl, (alkoxy)(halo)aryl, (alkoxy)heteroaryl, alkylaryl, alkylheteroaryl, aminoaryl, aminoheteroaryl, arylaryl, arylheteroaryl, (aryloxy)aryl, (aryloxy)heteroaryl, haloaryl, haloheteroaryl, (heteroalkyl)aryl, (haloalkyl)aryl, (heteroaryl)aryl, [(heteroaryl)oxy]aryl, [(aminoalkyl)oxy]aryl, aryl, heteroaryl, cycloalkyl and heterocycloalkyl, each of which can optionally be further substituted.

12. The compound according to claim 1, wherein A in Formula I is selected from the group consisting of 2-alkoxyphenyl, 3-alkoxyphenyl, 4-alkoxyphenyl, 2,3-dialkoxyphenyl, 2,4-dialkoxyphenyl, 2,5-dialkoxyphenyl, 2,6-dialkoxyphenyl, 3,4-dialkoxyphenyl, 3,5-dialkoxyphenyl, 3,4,5-trialkoxyphenyl, 2,6-dihalo-4-alkoxyphenyl, 2-halo-4-alkoxyphenyl, 3-halo-5-alkoxyphenyl, 4-halo-3-alkoxyphenyl, 2-alkylphenyl, 3-alkylphenyl, 4-alkylphenyl, 3-[(alkyl)(heteroalkyl)amino]phenyl, 3-[(dialkyl)amino]phenyl, 3-[(diheteroalkyl)amino]phenyl, 3-[(monoalkyl)amino]phenyl, 4-[(alkyl)(heteroalkyl)amino]phenyl, 4-[(dialkyl)amino]phenyl, 4-[(diheteroalkyl)amino]phenyl, 4-[(heteroaryl)oxy]phenyl, 4-[(monoalkyl)amino]phenyl, arylphenyl, 2-(aryloxy)phenyl, 3-(aryloxy)phenyl, 4-(aryloxy)phenyl, 2-halophenyl, 3-halophenyl, 4-halophenyl, 2,3-dihalophenyl, 2,4-dihalophenyl, 2,5-dihalophenyl, 2,6-dihalophenyl, 3,4-dihalophenyl, 3,5-dihalophenyl, 2,3,4-trihalophenyl, 2,3,5-trihalophenyl, 3,4,5-trihalophenyl, 2,4,5-trihalophenyl, 2,4,6-trihalophenyl, 3-(haloalkyl)phenyl, 4-(haloalkyl)phenyl, 3-(C5 monoheteroaryl)phenyl, 4-(C5 monoheteroaryl)phenyl, 3-(C4 monoheteroaryl)phenyl, 4-(C4 monoheteroaryl)phenyl, 3-[(heteroaryl)oxy]phenyl, 4-{[amino(alkyl)]oxy}phenyl, 3-{[amino(alkyl)]oxy}phenyl, naphthyl, phenyl, C5 monoheteroaryl, C4 monoheteroaryl, morpholinyl and piperidinyl, each of which can optionally be further substituted.

13. The compound according to claim 1, wherein A in Formula I is selected from the group consisting of 2-methoxyphenyl, 3-methoxyphenyl, 4-propoxyphenyl, 4-methoxyphenyl, 4-isopropoxyphenyl, 4-benzyloxyphenyl, 3,4-dimethoxyphenyl, 2,3-dihydro-1,4-benzodioxin-6-yl, 2,2-difluoro-1,3-benzodioxol-5-yl, 7-methoxy-1,3-benzodioxol-5-yl, 2,6-difluoro-4-methoxy-phenyl, 3-(1-piperidyl)phenyl, 4-morpholinophenyl, [1,1'-biphenyl]-3-yl, [1,1'-biphenyl]-4-yl, 3-phenoxyphenyl, 4-phenoxyphenyl, 2-chlorophenyl, 3-chlorophenyl, 4-chlorophenyl, 3,4-dichlorophenyl, 3,4,5-trifluorophenyl, 4-(2-pyridyl)phenyl, 4-(2-carbamimidamidoethyloxy)phenyl, 4-(2-aminoethoxy)phenyl, 4-(2-morpholinoethoxy)phenyl, phenyl, 2-pyridyl, 3-pyridyl, 4-pyridyl, 2-thienyl and 3-thienyl.

14. The compound according to claim 1, having a structure selected from the group consisting of:

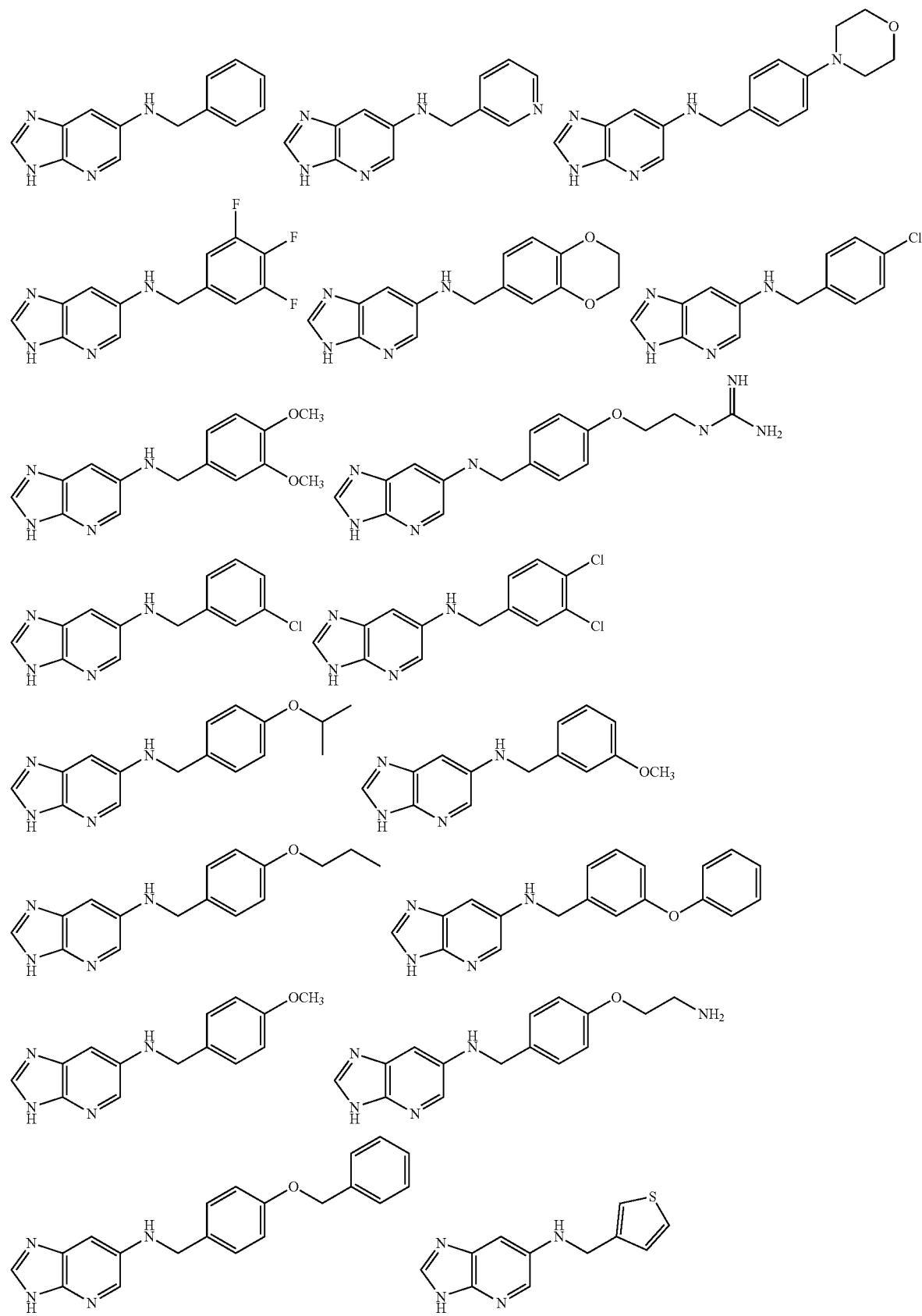

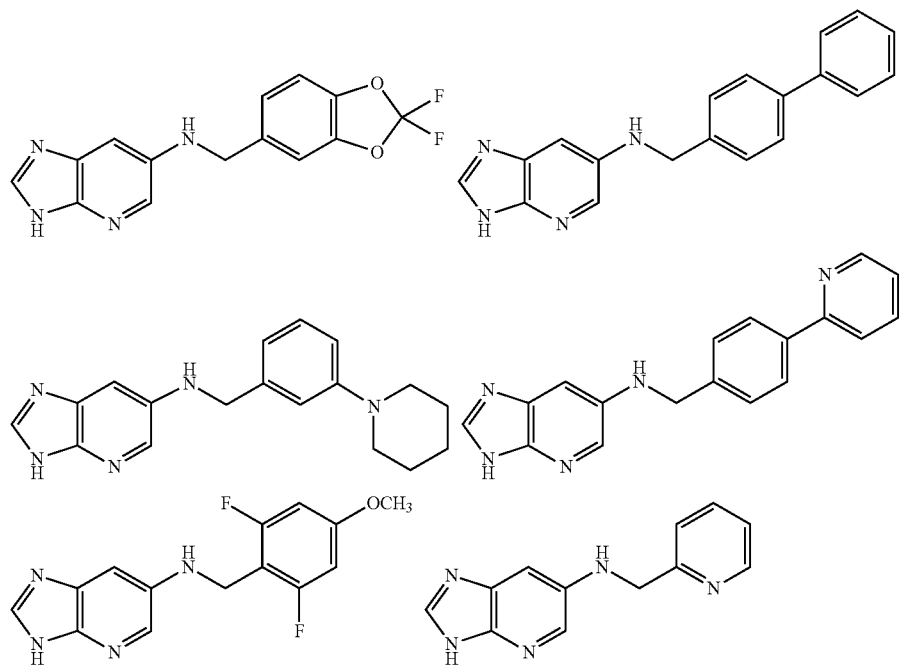
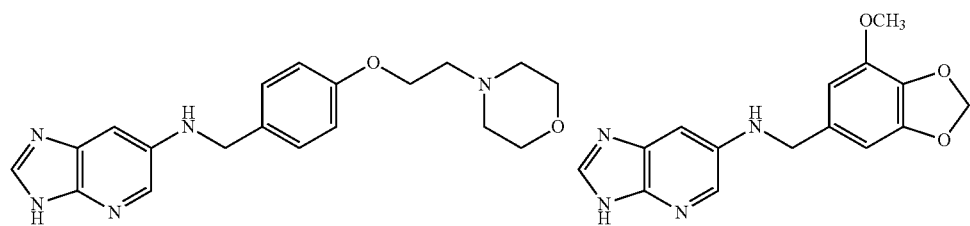
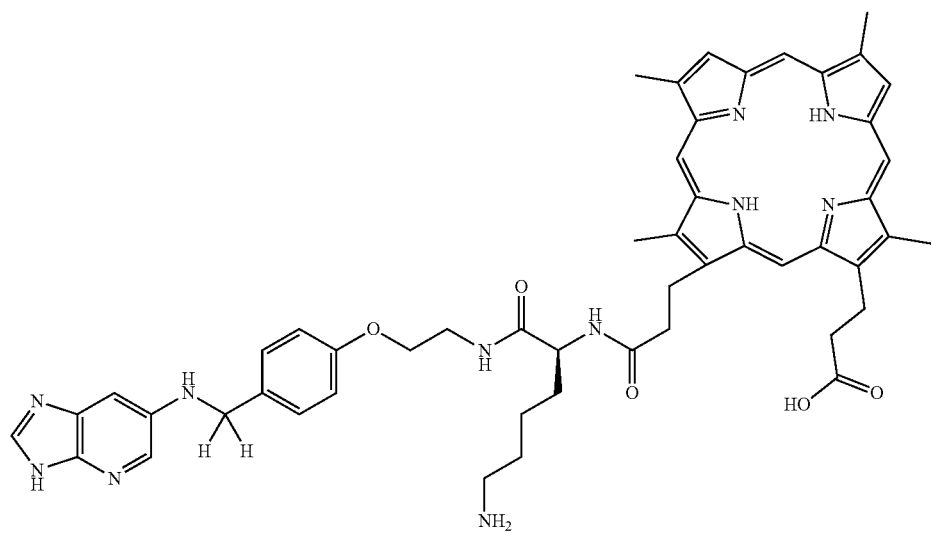
and

-continued
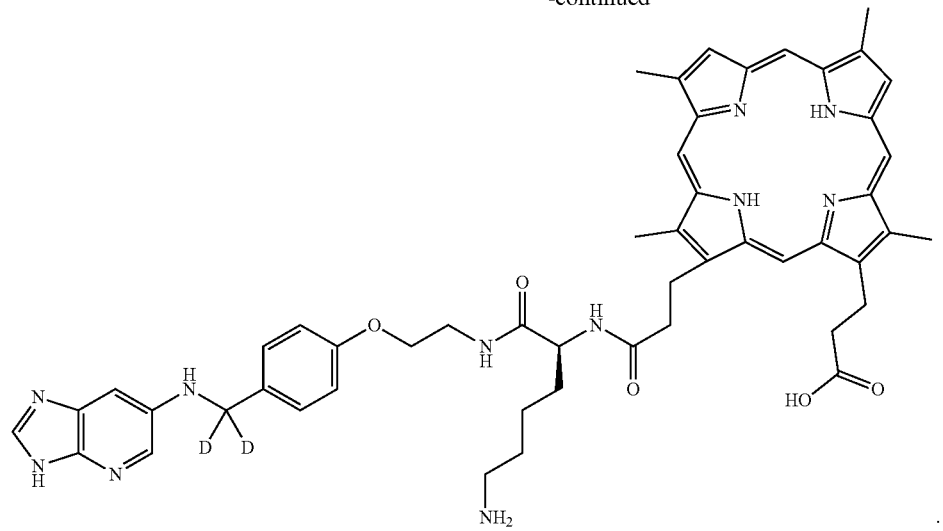
* * * * *

SEQUENCE LISTING

<160> NUMBER OF SEQ ID NOS: 14

<210> SEQ ID NO 1
<211> LENGTH: 333
<212> TYPE: PRT
<213> ORGANISM: Porphyromonas gingivalis
<220> FEATURE:
<223> OTHER INFORMATION: PgQC

<400> SEQUENCE: 1

```
Met Lys Arg Leu Ile Thr Thr Gly Ala Ala Phe Leu Leu Ala Ala Thr
1               5                   10                  15

Leu Ser Ala Cys Asn Gly Asn Asn Thr Ser Glu Thr Gln Gly Asp Arg
            20                  25                  30

Thr Glu Gln Ala Glu Thr Val Gln Ala Asp Leu Phe Ser Ala Asp Ser
        35                  40                  45

Ala Tyr Thr Phe Val Gln Arg Gln Val Asn Phe Gly Pro Arg Ile Pro
    50                  55                  60

Gly Thr Ala Pro His Arg Ala Cys Gly Asp Trp Leu Val Ala Thr Leu
65                  70                  75                  80

Arg Ser Phe Gly Ala Ala Val Gln Glu Gln Thr Ala Glu Ile Lys Ala
```

```
            85                  90                  95
His Asp Gly Thr Met Leu Pro Met Arg Asn Ile Ile Ala Ser Tyr Arg
            100                 105                 110

Pro Glu Ala Thr Gly Arg Met Leu Leu Met Ala His Trp Asp Thr Arg
            115                 120                 125

Pro Val Cys Asp Gln Asp Ala Asn Pro Ala Met His Thr Glu Thr Phe
            130                 135                 140

Asp Gly Ala Asp Gly Gly Ser Gly Val Gly Val Leu Leu Glu Ile
145                 150                 155                 160

Ala Arg Tyr Leu Gly Gln Gln Lys Asp Leu Gly Met Gly Ile Asp Ile
            165                 170                 175

Val Phe Phe Asp Thr Glu Asp Tyr Gly Ser Tyr Gly Asp Asp Glu Ser
            180                 185                 190

Trp Cys Leu Gly Ser Gln Tyr Trp Ser Arg Asn Pro His Val Ala Gly
            195                 200                 205

Tyr Lys Ala Glu Ala Gly Ile Leu Leu Asp Met Val Gly Ala Lys Gly
            210                 215                 220

Ala Thr Phe Tyr Trp Glu Tyr Phe Ser Lys Ser Tyr Ala Pro Gly Leu
225                 230                 235                 240

Ile Ser Ala Val Trp Gln Thr Ala Ala Leu Gly Tyr Gly Asn Tyr
            245                 250                 255

Phe Ile Gln Ala Asp Gly Gly Ala Leu Thr Asp Asp His Val Pro Val
            260                 265                 270

Ile Lys Asn Leu Gly Ile Pro Cys Ile Asp Ile Asn Tyr Ser Ser
            275                 280                 285

Lys Asn Glu His Gly Phe Gly Asp His Trp His Thr Gln Arg Asp Asn
            290                 295                 300

Met Gln Ile Ile Asp Lys Asn Val Leu Asp Ala Val Gly Glu Thr Val
305                 310                 315                 320

Ile Arg Tyr Leu Asp Glu Gln Val Lys Ala Ala Ser His
            325                 330

<210> SEQ ID NO 2
<211> LENGTH: 333
<212> TYPE: PRT
<213> ORGANISM: Tannerella forsythia
<220> FEATURE:
<223> OTHER INFORMATION: TfQC

<400> SEQUENCE: 2

Met Asp Arg Met Ile Asn Lys Tyr Ala Gly Val Leu Leu Gly Ser Leu
1               5                   10                  15

Ile Leu Ser Cys Cys Gly Gln Lys Asn Thr Thr Lys Glu Glu Thr Thr
            20                  25                  30

Glu Pro Ala Asp Thr Asp Lys Arg Ile Glu Ala Pro Thr Phe Asn Ala
            35                  40                  45

Asp Ser Ala Tyr Ala Tyr Ile Glu Arg Gln Val Ala Phe Gly Pro Arg
    50                  55                  60

Val Pro Asn Thr Glu Ala His Gln Arg Cys Ala Asp Tyr Leu Ala Gly
65                  70                  75                  80

Glu Leu Asp Arg His Gly Ala Lys Val Tyr Val Gln Glu Ala Val Leu
            85                  90                  95

Thr Ala Tyr Asn Gly Glu Lys Leu Lys Ala Gln Asn Ile Val Gly Ala
            100                 105                 110

Phe Gln Pro Glu Lys Ser Arg Arg Val Leu Leu Phe Ala His Trp Asp
```

```
            115                 120                 125
Ser Arg Pro Tyr Ala Asp His Asp Thr Asp Glu Ala Asn His Arg Lys
    130                 135                 140

Pro Ile Asp Gly Ala Asp Asp Gly Gly Ser Gly Val Gly Ile Leu Leu
145                 150                 155                 160

Glu Ile Ala Arg Gln Ile Gln Ala Lys Ala Pro Ala Ile Gly Ile Asp
                165                 170                 175

Ile Val Phe Phe Asp Ala Glu Asp Tyr Gly Thr Pro Glu Phe Val Asp
            180                 185                 190

Glu Tyr Lys Pro Asp Thr Trp Cys Leu Gly Ser Gln Phe Trp Ala Lys
        195                 200                 205

Asn Pro His Val Pro Asn Tyr Lys Ala Glu Phe Gly Ile Leu Leu Asp
    210                 215                 220

Met Val Gly Ser Arg Gly Ala Thr Phe Tyr Lys Glu Ser Thr Ser Val
225                 230                 235                 240

Gln Tyr Ala Ala Arg Tyr Val Glu Lys Val Trp Thr Ala Ala Arg Glu
                245                 250                 255

Leu Gly Tyr Gly Lys Tyr Phe Ile Asn Ala Gln Gly Gly Ala Ile Val
            260                 265                 270

Asp Asp His Gln Tyr Val Ile Gln Gly Leu Arg Thr Pro Cys Leu Asp
        275                 280                 285

Ile Ile Asn Tyr Asp Pro Asp Thr Gln Ser Gly Phe Gly Pro Tyr Trp
    290                 295                 300

His Thr Gln Asn Asp Thr Met Glu Asn Ile Asp Arg Glu Thr Leu Lys
305                 310                 315                 320

Ala Val Gly Glu Thr Ile Leu Asn Val Ile Tyr Asn His
                325                 330

<210> SEQ ID NO 3
<211> LENGTH: 363
<212> TYPE: PRT
<213> ORGANISM: Prevotella intermedia
<220> FEATURE:
<223> OTHER INFORMATION: PiQC

<400> SEQUENCE: 3

Met Gly Arg Gln Leu Ala Ala Arg Tyr Gly Thr Asp Thr Gly Cys Gln
1               5                   10                  15

Thr Lys Ile Lys Arg Thr Thr Met Asn Gly Lys Ile Lys Phe Leu Cys
                20                  25                  30

Ser Gly Met Ala Val Leu Leu Leu Ala Ala Phe Ala Phe Ser Cys Lys
            35                  40                  45

Gly Lys Ser Ser Asn Asn Ser Thr Glu Asp Gly Asp Thr Val Ala Thr
        50                  55                  60

Ala Lys Pro Val Gly Pro Thr Phe Asn Pro Asp Ser Ala Phe Ala Tyr
65                  70                  75                  80

Thr Ala Ala Gln Cys Asp Phe Gly Pro Arg Thr Met Asn Ser Ser Ala
                85                  90                  95

His Asp Lys Cys Glu Gln Trp Ile Ile Ser Lys Phe Lys Gln Tyr Gly
            100                 105                 110

Cys Glu Val Gln Thr Gln Lys Ala Asp Leu Lys Ala Tyr Asp Gly Thr
        115                 120                 125

Ile Leu Lys Ser Thr Asn Ile Ile Ala Arg Thr Asn Pro Asn Ala Gln
    130                 135                 140

Arg Arg Ile Leu Leu Cys Ala His Trp Asp Ser Arg Pro Trp Ala Asp
```

```
                    145                 150                 155                 160
Asn Asp Pro Asp Ser Thr Asn His Lys Lys Pro Val Met Ala Ala Asn
                165                 170                 175

Asp Gly Ala Ser Gly Val Gly Val Met Ile Glu Leu Ala Arg Gln Leu
            180                 185                 190

Gln Ala Asp Ser Thr Leu Asn Val Gly Val Asp Phe Val Cys Phe Asp
            195                 200                 205

Ala Glu Asp Trp Gly Val Pro Gln Trp Glu Thr Asn Tyr Gln Glu Gln
    210                 215                 220

Ser Gly Asp Ser Trp Ala Leu Gly Ser Asn Tyr Phe Ala Lys Asn Leu
225                 230                 235                 240

Pro Leu Thr Val Arg Pro Glu Phe Gly Ile Leu Leu Asp Met Val Gly
                245                 250                 255

Gly Glu Gly Ala Gln Phe Tyr Lys Glu Gly Ile Ser Leu Gln Tyr Ala
            260                 265                 270

Pro Asp Ile Val Asp Arg Val Trp Glu Ala Ala Lys Ser Ala Gly Phe
            275                 280                 285

Glu Ala Tyr Phe Pro Thr Thr Arg Gly Gly Met Val Thr Asp Asp His
    290                 295                 300

Tyr Pro Leu Asn Lys Ile Ala Ala Ile Pro Thr Ile Asp Ile Ile Pro
305                 310                 315                 320

His Tyr Pro Asp Cys Ala Gln Ser Thr Phe Gly Pro Thr Trp His Thr
                325                 330                 335

Val Asn Asp Thr Met Glu His Ile Asp Arg Thr Thr Leu Gln Ala Val
            340                 345                 350

Gly Gln Thr Leu Ile Gln Val Leu Tyr Ser Met
            355                 360

<210> SEQ ID NO 4
<211> LENGTH: 361
<212> TYPE: PRT
<213> ORGANISM: Homo sapiens
<220> FEATURE:
<223> OTHER INFORMATION: hQC

<400> SEQUENCE: 4

Met Ala Gly Gly Arg His Arg Arg Val Val Gly Thr Leu His Leu Leu
1               5                   10                  15

Leu Leu Val Ala Ala Leu Pro Trp Ala Ser Arg Gly Val Ser Pro Ser
                20                  25                  30

Ala Ser Ala Trp Pro Glu Glu Lys Asn Tyr His Gln Pro Ala Ile Leu
            35                  40                  45

Asn Ser Ser Ala Leu Arg Gln Ile Ala Glu Gly Thr Ser Ile Ser Glu
        50                  55                  60

Met Trp Gln Asn Asp Leu Gln Pro Leu Leu Ile Glu Arg Tyr Pro Gly
65                  70                  75                  80

Ser Pro Gly Ser Tyr Ala Ala Arg Gln His Ile Met Gln Arg Ile Gln
                85                  90                  95

Arg Leu Gln Ala Asp Trp Val Leu Glu Ile Asp Thr Phe Leu Ser Gln
            100                 105                 110

Thr Pro Tyr Gly Tyr Arg Ser Phe Ser Asn Ile Ile Ser Thr Leu Asn
            115                 120                 125

Pro Thr Ala Lys Arg His Leu Val Leu Ala Cys His Tyr Asp Ser Lys
        130                 135                 140

Tyr Phe Ser His Trp Asn Asn Arg Val Phe Val Gly Ala Thr Asp Ser
```

```
            145                 150                 155                 160
Ala Val Pro Cys Ala Met Met Leu Glu Leu Ala Arg Ala Leu Asp Lys
                165                 170                 175

Lys Leu Leu Ser Leu Lys Thr Val Ser Asp Ser Lys Pro Asp Leu Ser
                180                 185                 190

Leu Gln Leu Ile Phe Phe Asp Gly Glu Glu Ala Phe Leu His Trp Ser
                195                 200                 205

Pro Gln Asp Ser Leu Tyr Gly Ser Arg His Leu Ala Ala Lys Met Ala
            210                 215                 220

Ser Thr Pro His Pro Pro Gly Ala Arg Gly Thr Ser Gln Leu His Gly
225                 230                 235                 240

Met Asp Leu Leu Val Leu Leu Asp Leu Ile Gly Ala Pro Asn Pro Thr
                245                 250                 255

Phe Pro Asn Phe Phe Pro Asn Ser Ala Arg Trp Phe Glu Arg Leu Gln
                260                 265                 270

Ala Ile Glu His Glu Leu His Glu Leu Gly Leu Leu Lys Asp His Ser
                275                 280                 285

Leu Glu Gly Arg Tyr Phe Gln Asn Tyr Ser Tyr Gly Gly Val Ile Gln
            290                 295                 300

Asp Asp His Ile Pro Phe Leu Arg Arg Gly Val Pro Val Leu His Leu
305                 310                 315                 320

Ile Pro Ser Pro Phe Pro Glu Val Trp His Thr Met Asp Asp Asn Glu
                325                 330                 335

Glu Asn Leu Asp Glu Ser Thr Ile Asp Asn Leu Asn Lys Ile Leu Gln
                340                 345                 350

Val Phe Val Leu Glu Tyr Leu His Leu
                355                 360

<210> SEQ ID NO 5
<211> LENGTH: 30
<212> TYPE: DNA
<213> ORGANISM: Artificial Sequence
<220> FEATURE:
<223> OTHER INFORMATION: pgQC NdeI forward

<400> SEQUENCE: 5
aaacatatga acggcaataa cacaagtgaa                                        30

<210> SEQ ID NO 6
<211> LENGTH: 27
<212> TYPE: DNA
<213> ORGANISM: Artificial Sequence
<220> FEATURE:
<223> OTHER INFORMATION: pgQC NheI reverse

<400> SEQUENCE: 6
tttgctagct cagtgtgaag cggcttt                                           27

<210> SEQ ID NO 7
<211> LENGTH: 27
<212> TYPE: DNA
<213> ORGANISM: Artificial Sequence
<220> FEATURE:
<223> OTHER INFORMATION: piQC NdeI forward

<400> SEQUENCE: 7
tttcatatga aaggaaaatc gtctaac                                           27

<210> SEQ ID NO 8
```

```
<211> LENGTH: 26
<212> TYPE: DNA
<213> ORGANISM: Artificial Sequence
<220> FEATURE:
<223> OTHER INFORMATION: piQC NheI reverse

<400> SEQUENCE: 8
atgctagctt acatgctgta aagcac                                          26

<210> SEQ ID NO 9
<211> LENGTH: 27
<212> TYPE: DNA
<213> ORGANISM: Artificial Sequence
<220> FEATURE:
<223> OTHER INFORMATION: tfQC NdeI forward

<400> SEQUENCE: 9
tcacatatgg gtcagaaaaa tacgaca                                         27

<210> SEQ ID NO 10
<211> LENGTH: 29
<212> TYPE: DNA
<213> ORGANISM: Artificial Sequence
<220> FEATURE:
<223> OTHER INFORMATION: tfQC NheI reverse

<400> SEQUENCE: 10
atgctagctt atttctcatt ataaatcac                                       29

<210> SEQ ID NO 11
<211> LENGTH: 90
<212> TYPE: DNA
<213> ORGANISM: Artificial Sequence
<220> FEATURE:
<223> OTHER INFORMATION: seq pgQC NdeI forward

<400> SEQUENCE: 11
aaacatatga aaagactgat aacaacagga gcagcctttc tactggctgc tacactctct     60
gcctgcaacg gcaataacac aagtgaaacg                                      90

<210> SEQ ID NO 12
<211> LENGTH: 27
<212> TYPE: DNA
<213> ORGANISM: Artificial Sequence
<220> FEATURE:
<223> OTHER INFORMATION: seq pgQC XhoI reverse

<400> SEQUENCE: 12
tttctcgagg tgtgaagcgg ctttcac                                         27

<210> SEQ ID NO 13
<211> LENGTH: 21
<212> TYPE: DNA
<213> ORGANISM: Artificial Sequence
<220> FEATURE:
<223> OTHER INFORMATION: seq pgQC RBS NotI forward

<400> SEQUENCE: 13
tggcggccgc taagaaggag a                                               21

<210> SEQ ID NO 14
<211> LENGTH: 27
<212> TYPE: DNA
<213> ORGANISM: Artificial Sequence
<220> FEATURE:
<223> OTHER INFORMATION: seq pgQC XbaI reverse
```

```
<400> SEQUENCE: 14
ttttctagag tgtgaagcgg ctttcac                                          27
```